(12) United States Patent
Lu et al.

(10) Patent No.: US 9,580,480 B2
(45) Date of Patent: Feb. 28, 2017

(54) CELL-DIRECTED SYNTHESIS OF MULTIFUNCTIONAL NANOPATTERNS AND NANOMATERIALS

(75) Inventors: Timothy Kuan-Ta Lu, Charlestown, MA (US); Allen Yuyin Chen, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 482 days.

(21) Appl. No.: 14/119,319

(22) PCT Filed: May 31, 2012

(86) PCT No.: PCT/US2012/040191
§ 371 (c)(1),
(2), (4) Date: Dec. 5, 2014

(87) PCT Pub. No.: WO2012/166906

PCT Pub. Date: Dec. 6, 2012

(65) Prior Publication Data
US 2015/0118712 A1    Apr. 30, 2015

Related U.S. Application Data

(60) Provisional application No. 61/491,697, filed on May 31, 2011.

(51) Int. Cl.
*C07K 14/245* (2006.01)
*B82Y 5/00* (2011.01)
*B82Y 40/00* (2011.01)
*C07K 14/47* (2006.01)

(52) U.S. Cl.
CPC .............. *C07K 14/245* (2013.01); *B82Y 5/00* (2013.01); *B82Y 40/00* (2013.01); *C07K 14/4711* (2013.01); *C07K 2319/00* (2013.01); *C07K 2319/20* (2013.01); *C07K 2319/21* (2013.01); *C07K 2319/24* (2013.01); *C07K 2319/43* (2013.01); *C07K 2319/60* (2013.01); *C07K 2319/735* (2013.01)

(58) Field of Classification Search
None
See application file for complete search history.

(56) References Cited

U.S. PATENT DOCUMENTS 6,585,980 B1 *   7/2003   Chan ................... C07K 14/205
                                                               424/184.1

OTHER PUBLICATIONS

Barnhart et al., Curli biogenesis and function. Annu Rev Microbiol. 2006;60:131-47.
Gardner et al., Construction of a genetic toggle switch in *Escherichia coli*. Nature. Jan. 20, 2000;403(6767):339-42.
Kasotakis et al., Design of metal-binding sites onto self-assembled peptide fibrils. Biopolymers. 2009;92(3):164-72. doi: 10.1002/bip.21163.
Kolodkin-Gal et al., D-amino acids trigger biofilm disassembly. Science. Apr. 30, 2010;328(5978):627-9. doi:10.1126/science.1188628.
Lee et al., Fabricating genetically engineered high-power lithium-ion batteries using multiple virus genes. Science. May 22, 2009;324(5930):1051-5. doi: 10.1126/science.1171541. Epub Apr. 2, 2009.
Nam et al., Virus-enabled synthesis and assembly of nanowires for lithium ion battery electrodes. Science. May 12, 2006;312(5775):885-8. Epub Apr. 6, 2006.
Scheibel et al., Conducting nanowires built by controlled self-assembly of amyloid fibers and selective metal deposition. Proc Natl Acad Sci U S A. Apr. 15, 2003;100(8):4527-32. Epub Apr. 2, 2003.
Shewmaker et al., The functional curli amyloid is not based on in-register parallel beta-sheet structure. J Biol Chem. Sep. 11, 2009;284(37):25065-76. doi: 10.1074/jbc.M109.007054. Epub Jul. 1, 2009.
Tamerler et al., Molecular biomimetics: utilizing nature's molecular ways in practical engineering. Acta Biomater. May 2007;3(3):289-99. Epub Jan. 25, 2007.
Baldwin et al., Cytochrome display on amyloid fibrils. J Am Chem Soc. Feb. 22, 2006;128(7):2162-3.
Basu et al., A synthetic multicellular system for programmed pattern formation. Nature. Apr. 28, 2005;434(7037):1130-4.
Baxa et al., Mechanism of inactivation on prion conversion of the Saccharomyces cerevisiae Ure2 protein. Proc Natl Acad Sci U S A. Apr. 16, 2002;99(8):5253-60.
Bian et al., Nucleator function of CsgB for the assembly of adhesive surface organelles in *Escherichia coli*. EMBO J. Oct. 1, 1997;16(19):5827-36.
Catterall, Structure and function of voltage-sensitive ion channels. Science. Oct. 7, 1988;242(4875):50-61.
Cherny et al., The formation of *Escherichia coli* curli amyloid fibrils is mediated by prion-like peptide repeats. J Mol Biol. Sep. 16, 2005;352(2):245-52.
Darwin et al., Molecular basis of the interaction of *Salmonella* with the intestinal mucosa. Clin Microbiol Rev. Jul. 1999;12(3):405-28.
Dickerson et al., Protein- and peptide-directed syntheses of inorganic materials. Chem Rev. Nov. 2008;108(11):4935-78. doi: 10.1021/cr8002328. Epub Oct. 31, 2008.
Dueholm et al., Functional amyloid in Pseudomonas. Mol Microbiol. Jun. 21, 2010.
Elowitz et al., A synthetic oscillatory network of transcriptional regulators. Nature. Jan. 20, 2000;403(6767):335-8.
Faivre et al., Magnetotactic bacteria and magnetosomes. Chem Rev. Nov. 2008;108(11):4875-98. doi: 10.1021/cr078258w. Epub Oct. 15, 2008.
Flemming et al., The biofilm matrix. Nat Rev Microbiol. Sep. 2010;8(9):623-33. doi: 10.1038/nrmicro2415. Epub Aug. 2, 2010.
Friedland et al., Synthetic gene networks that count. Science. May 29, 2009;324(5931):1199-202. doi:10.1126/science.1172005.
Gorby et al., Electrically conductive bacterial nanowires produced by Shewanella oneidensis strain MR-1 and other microorganisms. Proc Natl Acad Sci U S A. Jul. 25, 2006;103(30):11358-63. Epub Jul. 18, 2006.
Jensen et al., Engineering of a synthetic electron conduit in living cells. Proc Natl Acad Sci U S A. Nov. 9, 2010;107(45):19213-8. doi: 10.1073/pnas.1009645107. Epub Oct. 18, 2010.

(Continued)

*Primary Examiner* — Anand Desai
(74) *Attorney, Agent, or Firm* — Wolf, Greenfield & Sacks, P.C.

(57) ABSTRACT

Aspects of the invention relate to the engineering of biological nanostructures and materials.

21 Claims, 45 Drawing Sheets

(56) References Cited

OTHER PUBLICATIONS

Kobayashi et al., Programmable cells: interfacing natural and engineered gene networks. Proc Natl Acad Sci U S A. Jun. 1, 2004;101(22):8414-9. Epub May 24, 2004.

Lee et al., Ordering of quantum dots using genetically engineered viruses. Science. May 3, 2002;296(5569):892-5.

Levskaya et al., Synthetic biology:engineering *Escherichia coli* to see light. Nature. Nov. 24, 2005;438(7067):441-2.

Long et al., Three-dimensional battery architectures. Chem Rev. Oct. 2004;104(10):4463-92.

Lu, Engineering scalable biological systems. Bioengineered Bugs 1(6);2010:378-384.

Lu et al., Next-generation synthetic gene networks. Nat Biotechnol. Dec. 2009;27(12):1139-50. doi: 10.1038/nbt.1591.

Maeda et al., Magnetically sensitive light-induced reactions in cryptochrome are consistent with its proposed role as a magnetoreceptor. Proc Natl Acad Sci U S A. Mar. 27, 2012;109(13):4774-9. doi: 10.1073/pnas.1118959109. Epub Mar. 14, 2012.

Mao et al., Virus-based toolkit for the directed synthesis of magnetic and semiconducting nanowires. Science. Jan. 9, 2004;303(5655):213-7.

Otoo et al., Candida albicans Als adhesins have conserved amyloid-forming sequences. Eukaryot Cell. May 2008;7(5):776-82. Epub Dec. 14, 2007.

Peelle et al., Design criteria for engineering inorganic material-specific peptides. Langmuir. Jul. 19, 2005;21(15):6929-33.

Pisciotta et al., Light-dependent electrogenic activity of cyanobacteria. PLoS One. May 25, 2010;5(5):e10821. doi:10.1371/journal.pone.0010821.

Ramsook et al., Yeast cell adhesion molecules have functional amyloid-forming sequences. Eukaryot Cell. Mar. 2010;9(3):393-404. doi: 10.1128/EC.00068-09. Epub Dec. 28, 2009.

Reches et al., Casting metal nanowires within discrete self-assembled peptide nanotubes. Science. Apr. 25, 2003;300(5619):625-7.

Reguera et al., Extracellular electron transfer via microbial nanowires. Nature. Jun. 23, 2005;435(7045):1098-101.

Romero et al., Amyloid fibers provide structural integrity to Bacillus subtilis biofilms. Proc Natl Acad Sci U S A. Feb. 2, 2010;107(5):2230-4. doi: 10.1073/pnas.0910560107. Epub Jan. 13, 2010.

Stricker et al., A fast, robust and tunable synthetic gene oscillator. Nature. Nov. 27, 2008;456(7221):516-9. doi: 10.1038/nature07389. Epub Oct. 29, 2008.

Tamsir et al., Robust multicellular computing using genetically encoded NOR gates and chemical 'wires'. Nature. Jan. 13, 2011;469(7329):212-5. doi: 10.1038/nature09565. Epub Dec. 8, 2010.

Teertstra et al., The filament-specific Rep1-1 repellent of the phytopathogen Ustilago maydis forms functional surface-active amyloid-like fibrils. J Biol Chem. Apr. 3, 2009;284(14):9153-9. doi: 10.1074/jbc.M900095200. Epub Jan. 21, 2009.

Wang et al., The molecular basis of functional bacterial amyloid polymerization and nucleation. J Biol Chem. Aug. 1, 2008;283(31):21530-9. doi: 10.1074/jbc.M800466200. Epub May 27, 2008.

\* cited by examiner

Figure 6

A CsgA

```
Sec  M K L L K V A A I A A I V F S G S A L A
N22  G V V P Q Y G G G G N H G G G G N N S G P N
R1   S E L N I Y Q Y G G G N S A L A L Q T D A R N
R2   S D L T I T Q H G G G N G A D V G Q - G S D D
R3   S S I D L T Q R G F G N S A T L D Q W N G K N
R4   S E M T V K Q F G G G N G A A V D Q - T A S N
R5   S S V N V T Q V G F G N N A T A H Q Y
```

B CsgB

```
Sec  M K N K L L F M M L T I L G A P G I A A A
N23  A G Y D L A N S E Y N F A V N E L S K S S F N
R1   Q A A I I G Q A G T N N S A Q L R Q G G S K
R2   L L A V V A Q E G S S N R A K I D Q T G D Y
R3   N L A Y I D Q A G S A N D A S I S Q G A Y G
R4   N T A M I I Q K G S G N K A N I T Q Y G T Q
R5   K T A I V V Q R Q S Q M A I R V T Q R
```

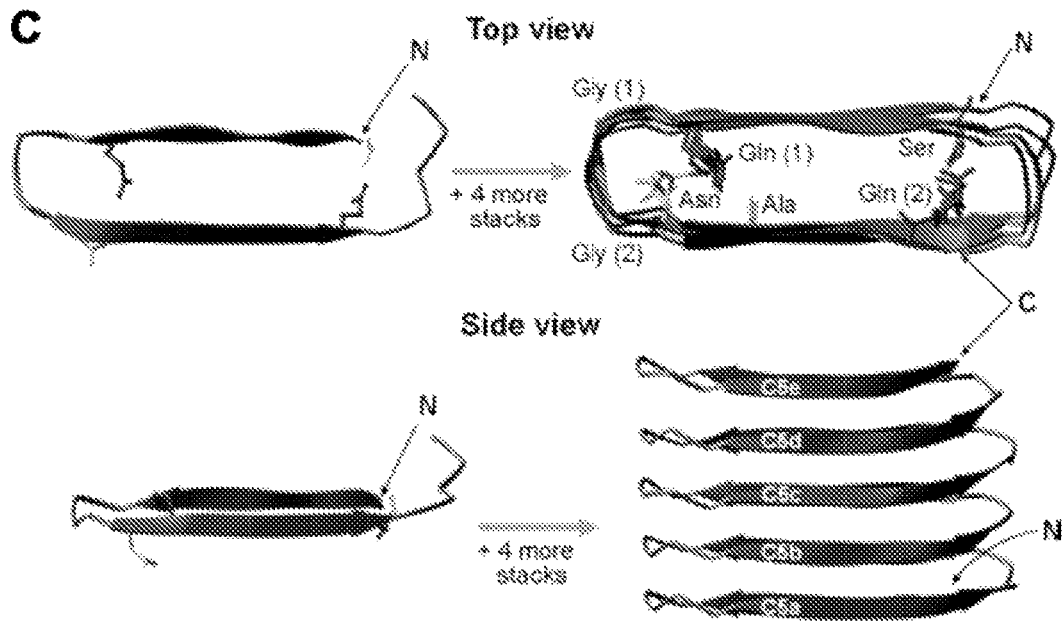

Figure 11
A
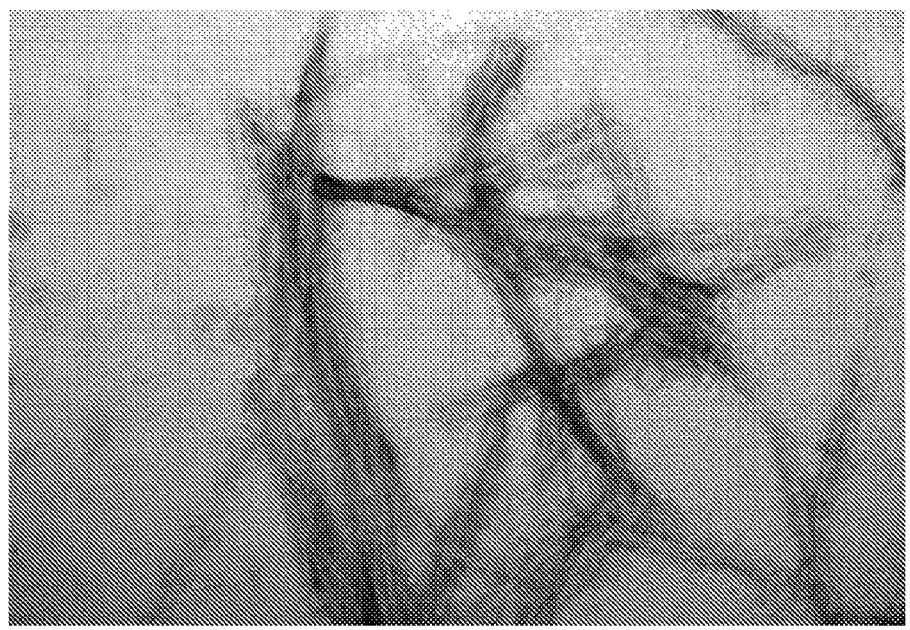
B
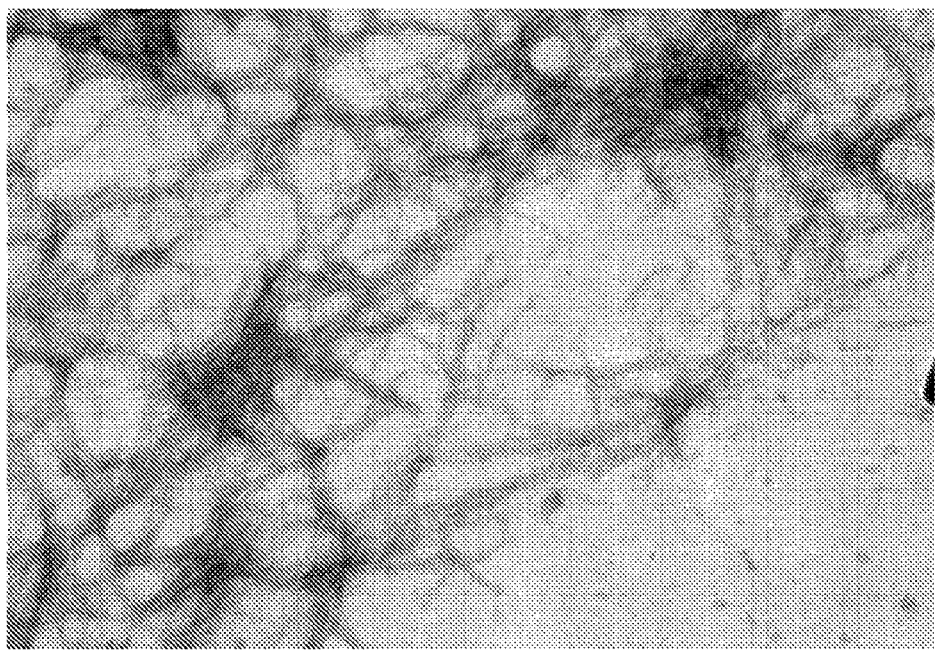

Figure 14
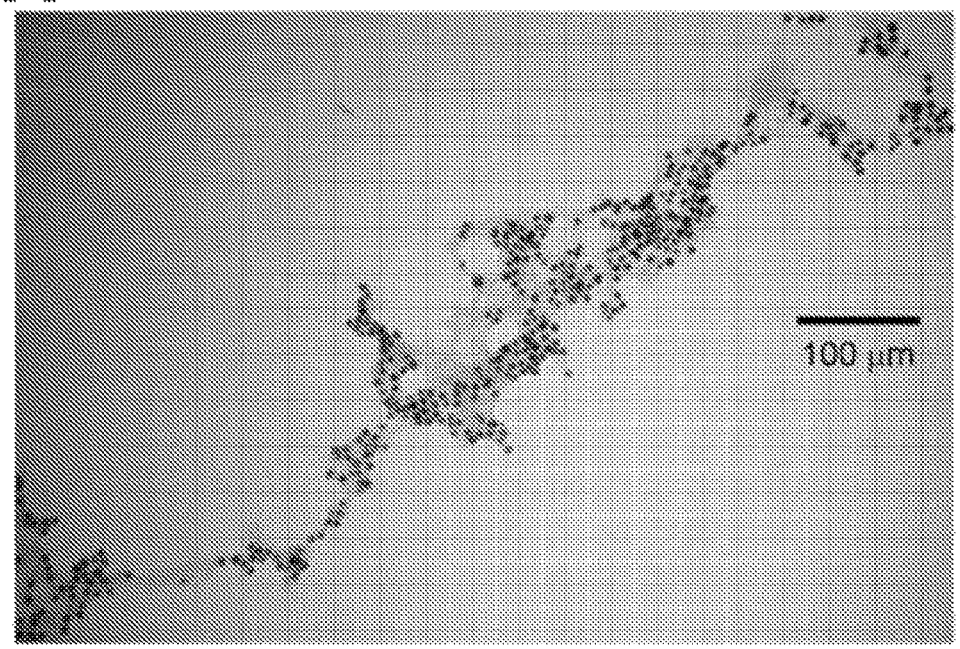
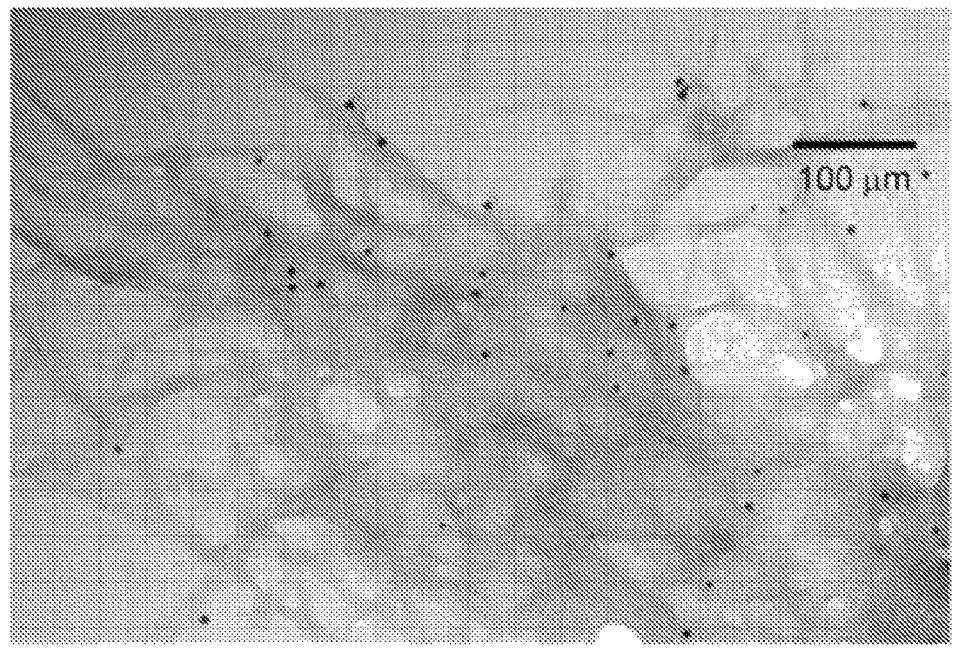

Figure 15
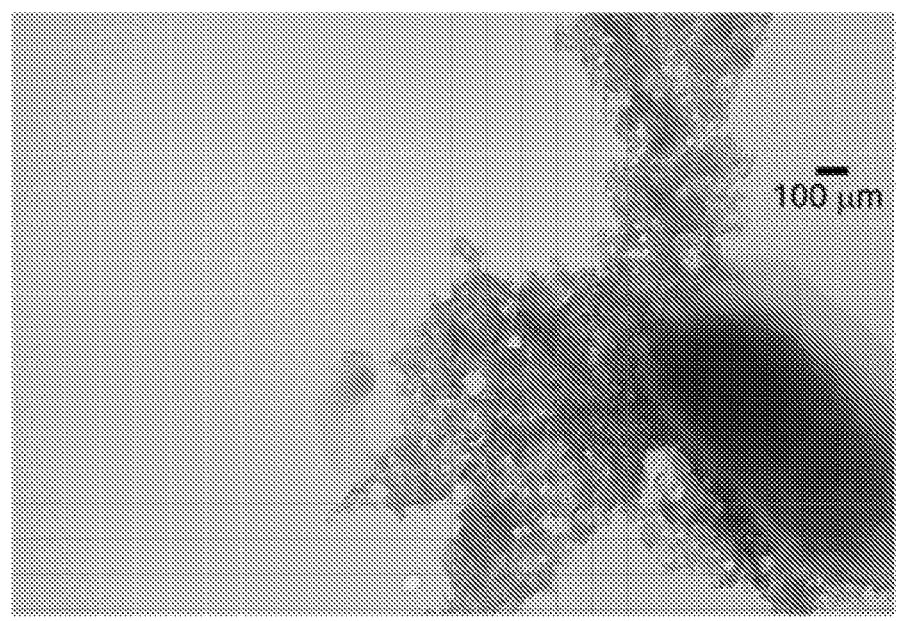
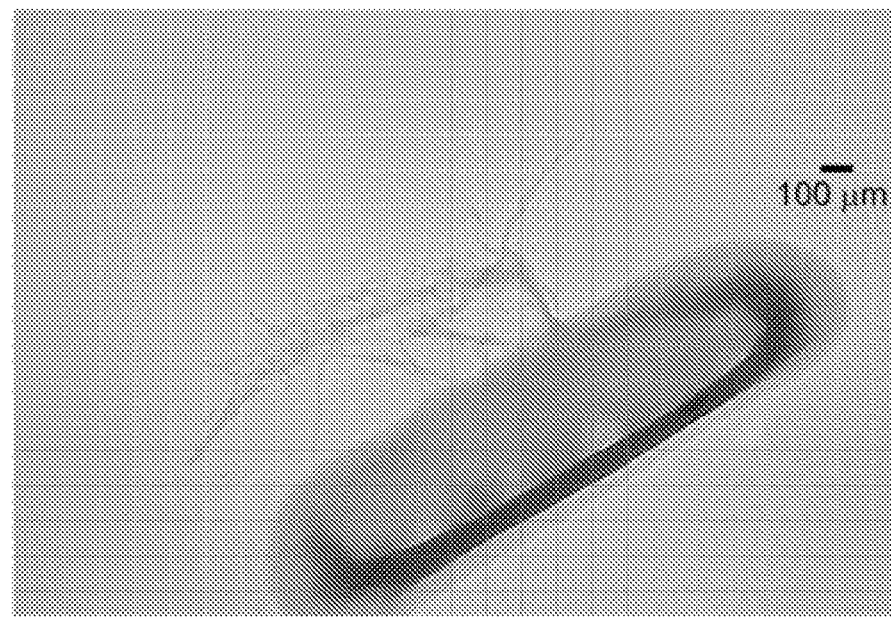

Figure 20

Inserting 7xHis throughout the CsgA structure

| Location of 7xHis | KpnI-PrimerF1 | PrimerR1-7xHis | 7xHis-PrimerF2 | PrimerR2-MluI |
|---|---|---|---|---|
| Between R1 & R2 | same as D1283 aycP41 | part7xHis-CsgA(62)-r (D1364) | part7xHis-CsgA(63)-f (D1363) | MluI-CsgA-r (D1284) |
| Between R2 & R3 | same as D1283 aycP41 | part7xHis-CsgA(85)-r (D1366) | part7xHis-CsgA(86)-f (D1365) | MluI-CsgA-r (D1284) |
| Between R3 & R4 | same as D1283 aycP41 | part7xHis-CsgA(107)-r (D1368) | part7xHis-CsgA(108)-f (D1367) | MluI-CsgA-r (D1284) |
| Between R4 & R5 | same as D1283 aycP41 | part7xHis-CsgA(130)-r (D1370) | part7xHis-CsgA(131)-f (D1369) | MluI-CsgA-r (D1284) |
| Within R1 | same as D1283 aycP41 | part7xHis-CsgA(52)-r (D1372) | part7xHis-CsgA(53)-f (D1371) | MluI-CsgA-r (D1284) |
| Within R2 | same as D1283 aycP41 | part7xHis-CsgA(75)-r (D1374) | part7xHis-CsgA(76)-f (D1373) | MluI-CsgA-r (D1284) |
| Within R3 | same as D1283 aycP41 | part7xHis-CsgA(97)-r (D1376) | part7xHis-CsgA(98)-f (D1375) | MluI-CsgA-r (D1284) |
| Within R4 | same as D1283 aycP41 | part7xHis-CsgA(120)-r (D1378) | part7xHis-CsgA(121)-f (D1377) | MluI-CsgA-r (D1284) |
| Within R5 | same as D1283 aycP41 | part7xHis-CsgA(142)-r (D1380) | part7xHis-CsgA(143)-f (D1379) | MluI-CsgA-r (D1284) |

Figure 25
A
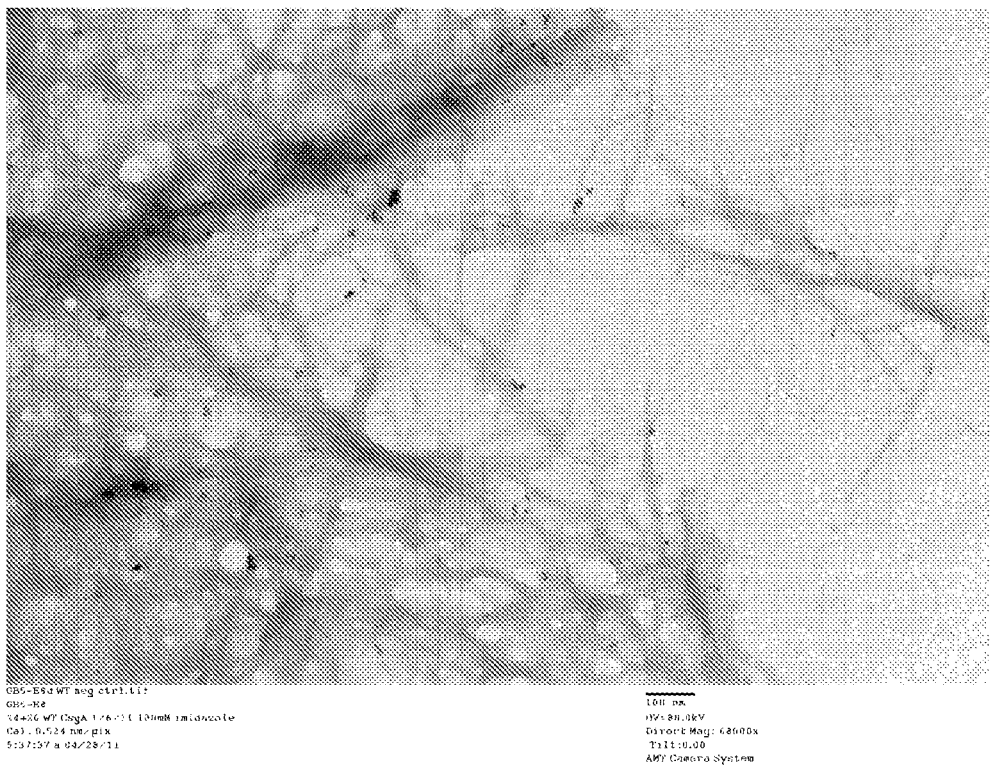
B
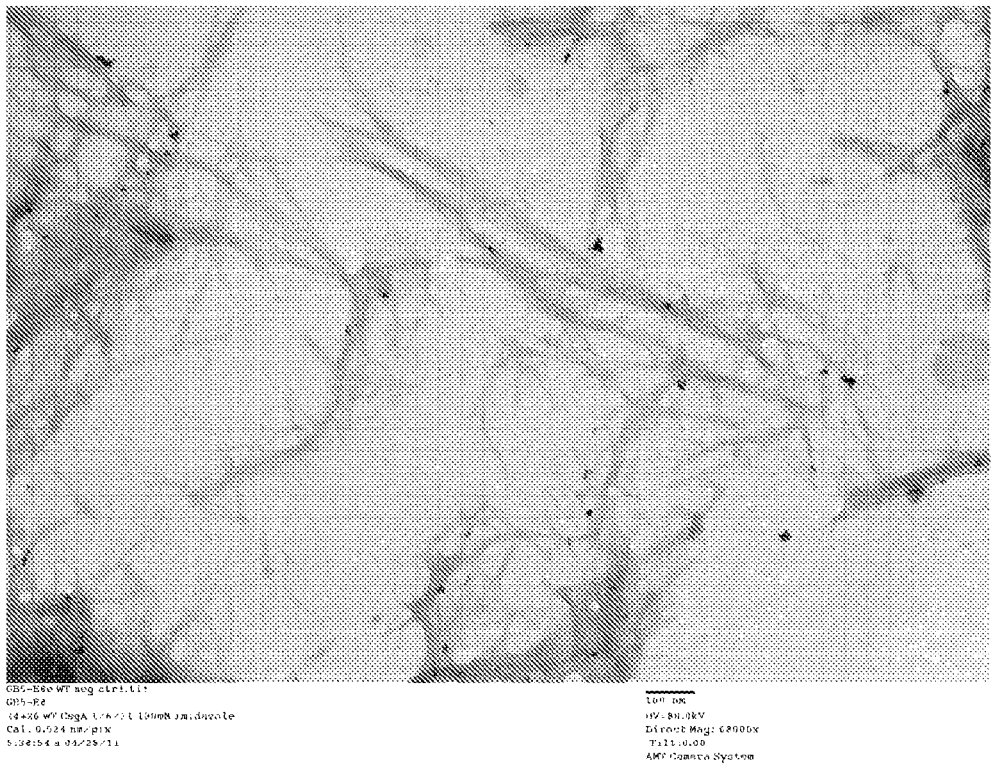

Figure 29
A 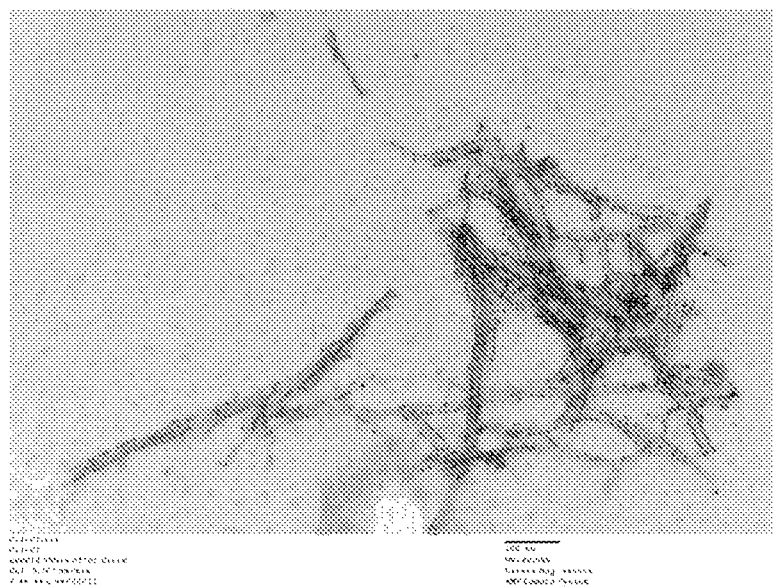
B 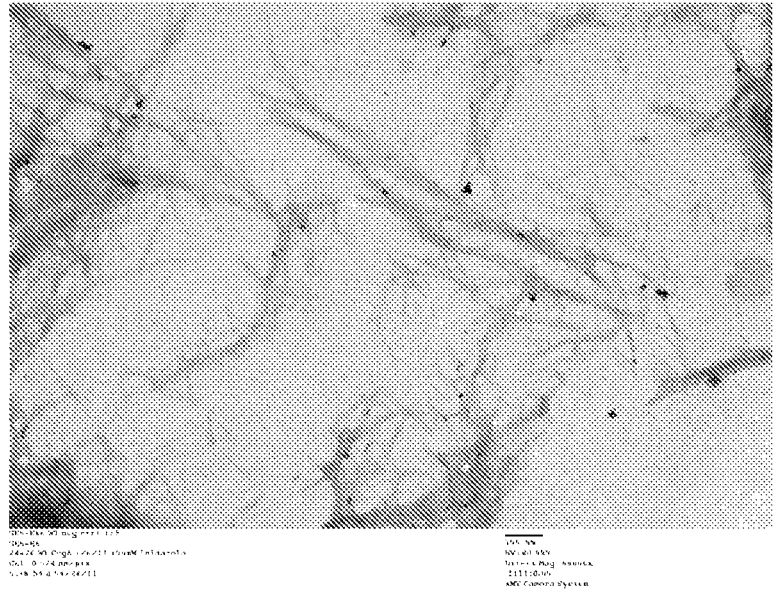

Figure 32
A 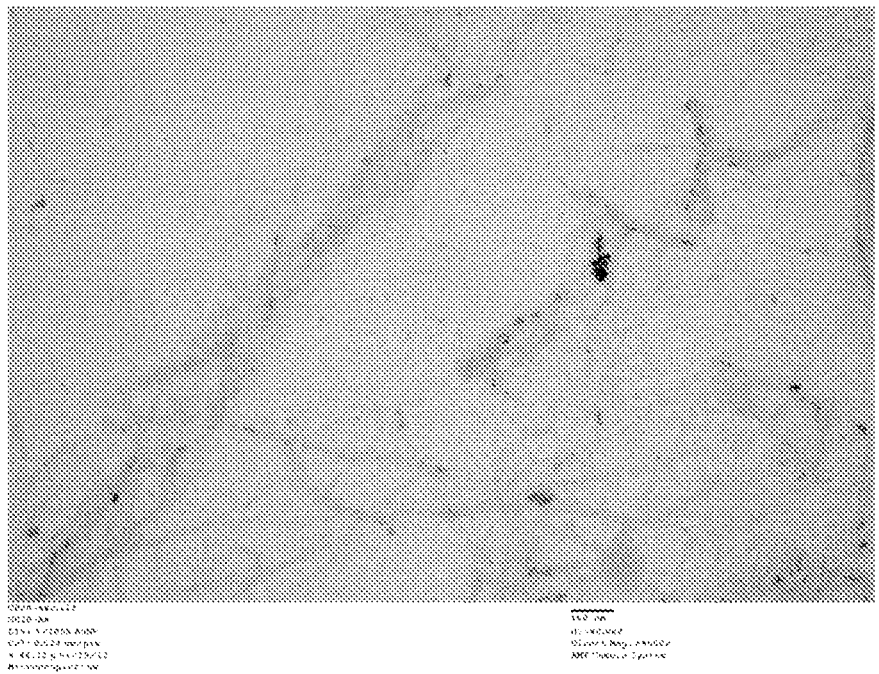
B 

Figure 32

Figure 32

Figure 33
A
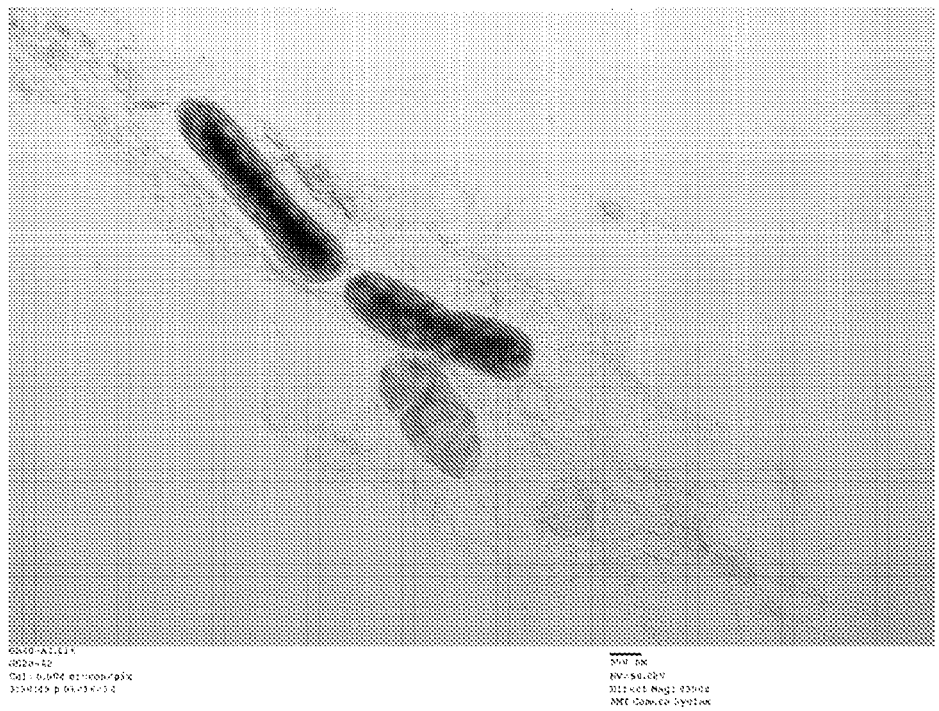
B
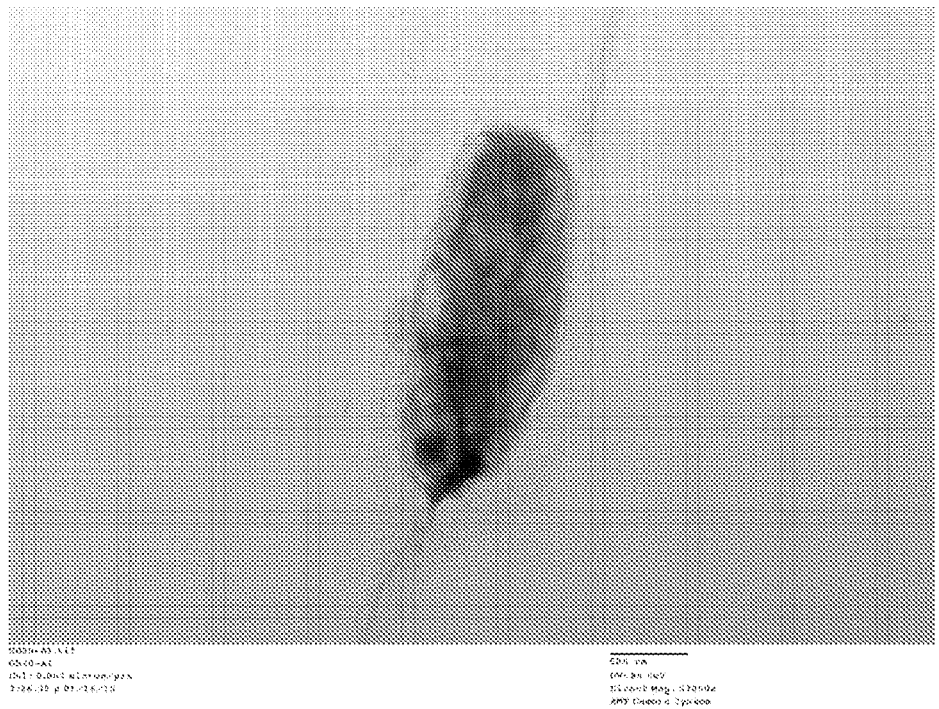

C

D

Figure 34
A 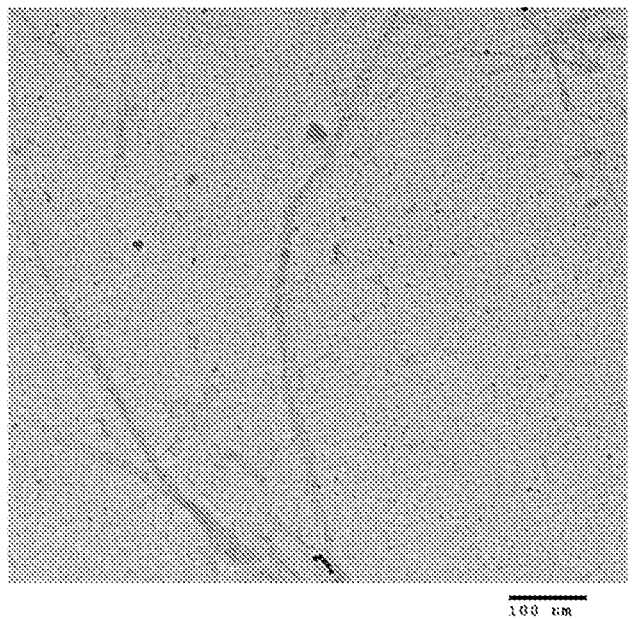
B 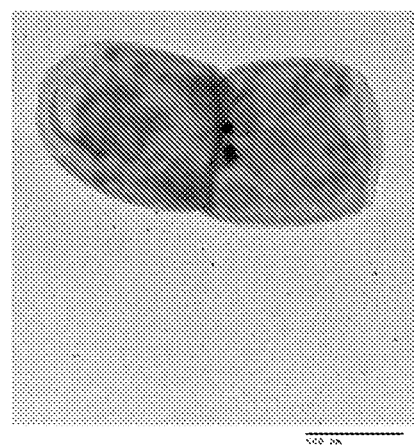

Figure 35
A
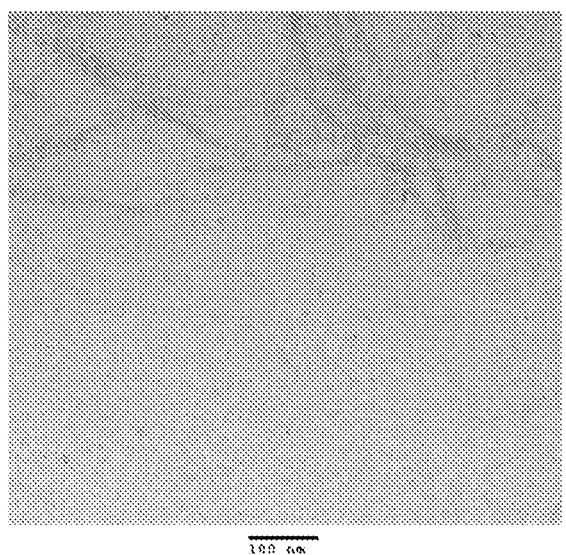
B
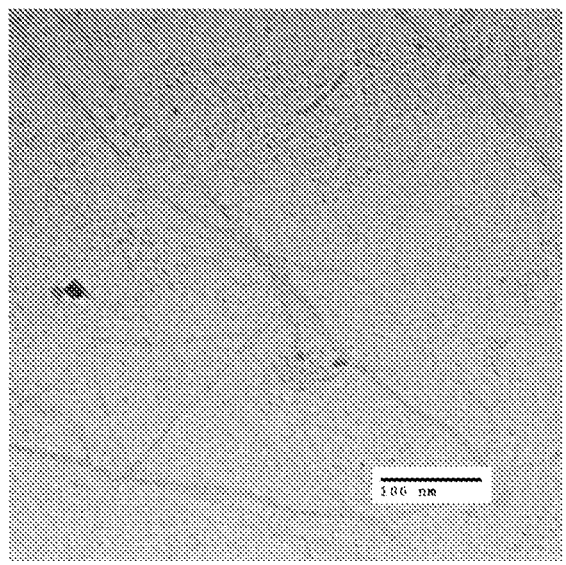

Figure 35
C
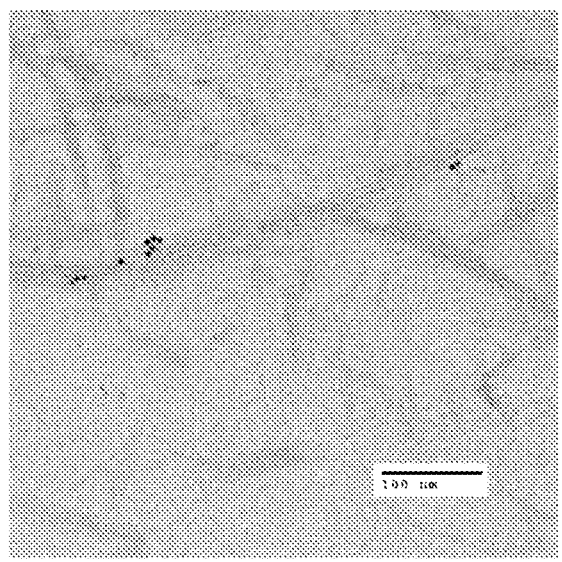
D
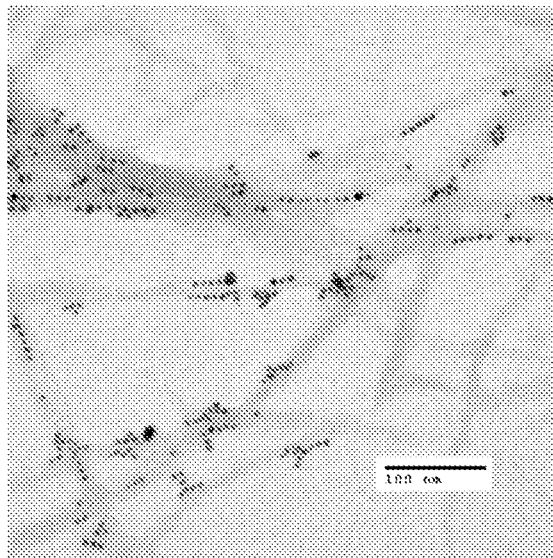

Magnet on L, no IONP      Magnet on L, IONP

Quantum dots templated on amyloid

CELL-DIRECTED SYNTHESIS OF MULTIFUNCTIONAL NANOPATTERNS AND NANOMATERIALS

RELATED APPLICATION

This application is a national stage filing under 35 U.S.C. §371 of international application PCT/US2012/040191, filed May 31, 2012, which was published under PCT Article 21(2) in English, and claims the benefit under 35 U.S.C. §119(e) of U.S. Provisional Application Ser. No. 61/491, 697, entitled "Cell-directed Synthesis of Multifunctional Nanopatterns and Nanomaterials," filed on May 31, 2011, the entire disclosure of each of which is incorporated by reference herein in its entirety.

FEDERALLY SPONSORED RESEARCH

This invention was made with Government support under Grant No. DMR0819762 awarded by the National Science Foundation, under Contract No. N00014-11-1-0687 awarded by the Office of Naval Research, and under Contract No. W911NF-11-1-0281 awarded by the Army Research Office. The Government has certain rights in the invention.

FIELD OF THE INVENTION

The invention relates to engineering of biological nanostructures.

BACKGROUND OF INVENTION

Synthetic biology and nanotechnology are emerging fields that are revolutionizing the materials, energy, devices, and organisms used in all facets of life. Synthetic biology is an engineering discipline for programming biological systems to achieve new functionalities. Nanotechnology takes advantage of the emergent properties of materials as their characteristic dimensions approach the nanometer scale.

Many of the systems designed for interfacing biological and non-biological materials have used filamentous-phage-displayed peptides which bind to inorganic materials. These methods have found important applications, including ordering quantum dots, creating magnetic and semiconducting nanowires, and building electrodes for lithium ion batteries. However, there are several major limitations with the phage-display approach. Filamentous phages can only accommodate short peptides for surface expression, which can significantly limit the extent to which they can be functionalized. Anisotropic patterning along the length of a phage is difficult to achieve since phage coat subunits to which peptides are fused are randomly incorporated into the phage coat structure. Phage-based nanowires are restricted by the inherent dimensions of the phage itself and cannot be easily extended, shortened, widened, or polymerized. Moreover, since phages are not autonomous living organisms, they are incapable of interfacing inorganic materials with synthetic gene circuits within living cells. DNA has also been used as a template for assembling inorganic materials but DNA is unstable at high temperatures and pH levels which may be necessary for metallization processes (Scheibel et al., (2003) *Proc Natl Acad Sci USA* 100:4527). In addition, DNA is not readily exported or displayed extracellularly and so, its ability to link living cells with non-living materials is greatly limited.

SUMMARY OF INVENTION

Despite significant advances in engineering nanomaterials, many challenging hurdles still persist, including anisotropic nanoscale patterning and organizing materials from the nanoscale all the way up to the microscale and the macroscale. These problems are addressed herein using an interdisciplinary approach which combines synthetic biology with nanotechnology. This is a powerful and feasible strategy that is founded upon the ability of natural and engineered organisms to organize organic and inorganic structures with great precision at length scales that vary over many orders of magnitude.

Aspects of the invention relate to a cell that is genetically engineered to express one or more polymer(s) which assembles into a biological nanostructure on the surface of the cell, outside the cell or inside the cell. In some embodiments, one or more of the polymers is modified. In some embodiments, the cell is a bacterial cell, fungal cell (including a yeast cell) or mammalian cell. In some embodiments, the polymer is an amyloid, pili or flagella.

In some embodiments, one or more of the polymers comprises one or more heterologous polypeptide domains. In some embodiments, one or more of the heterologous polypeptide domains binds to one or more inorganic nanomaterials. In some embodiments, the one or more inorganic nanomaterials comprises one or more metals or metal nanoparticles. In certain embodiments, the one or more of the metals or metal nanoparticles includes gold nanoparticles, silver nanoparticles, zinc sulfate, cadmium sulfate, iron oxide, cobalt oxide, cobalt platinum, iron platinum or quantum dots.

In some embodiments, one or more of the heterologous polypeptide domains binds to other polymers or protein structures. In some embodiments, expression of the polymers is under the control of inducible promoters. In some embodiments, the expression and/or composition of polymers, or subunits thereof, is temporally regulated.

In some embodiments, the cell expresses at least two different polymers, and the different polymers, or subunits thereof, are expressed with different heterologous polypeptides. In some embodiments, the cell is a bacterial cell, such as a cell of the *Escherichia, Salmonella, Pseudomonas, Bacillus, Citrobacter, Shigella* or *Enterobacter* genus. In certain embodiments, the cell is an *Escherichia coli* (*E. coli*) cell, a *Pseudomonas aeruginosa* (*P. aeruginosa*) cell or a *Bacillus subtilis* (*B. subtilis*) cell.

In some embodiments, the cell is an *E. coli* cell, and the polymer is an amyloid fiber, such as a curli fiber. In some embodiments, the cell expresses a csgBAC and/or a csgDEFG operon and one or more components of the csgBAC and/or csgDEFG operons is genetically engineered. In some embodiments, one or more components of the csgBAC and/or csgDEFG operons is expressed on a plasmid. In certain embodiments, csgA and/or csgB is expressed on a plasmid under the control of an inducible promoter, such as pLtetO, pLlacO, a LacI riboregulator, a TetR riboregulator or a LuxR riboregulator.

In some embodiments, one or more heterologous polypeptide domains are attached to CsgA. In certain embodiments, the one or more heterologous polypeptide domains are attached to the C-terminus of CsgA. In some embodiments, csgA and/or csgB are genetically engineered to express charged residues, such as glutamic acid. In certain embodiments, CsgA, CsgB and Maltose-binding protein (MBP) are expressed in the cell under independent, inducible control.

In some embodiments, the polymers are genetically engineered to promote release of the polymers from the cell. In some embodiments, exogenous D-amino acids enable the detachment of polymers from the cell surface. In certain embodiments, one or more of the D-amino acids is D-leucine, D-methionine, D-tyrosine or D-tryptophan. In some embodiments, the cells overexpresses a gene encoding for an enzyme that converts L-amino acids to D-amino acids. In certain embodiments, the gene encoding for an enzyme that converts L-amino acids to D-amino acids is selected from the group consisting of ylmE, racX, alr, dadX, murI, yhfX and ygeA.

In some embodiments, one or more inorganic-binding peptides is incorporated into one or more of the curli fibers. In some embodiments, the inorganic is a metal or a semiconductor. In some embodiments, one or more of the metal-binding peptides is a gold-binding peptide (Au-BP). In some embodiments, the Au-BP is fused to CsgA. In certain embodiments, the Au-BP is fused to the C terminus of CsgA. In certain embodiments, the Au-BP comprises the sequence LKAHLPPSRLPS (SEQ ID NO:1).

In some embodiments, one or more of the semiconductor-binding peptides is a ZnS-binding peptide (ZnS-BP) and/or a CdS-binding peptide (CdS-BP). In certain embodiments, the ZnS-BP comprises the sequence CNNPMHQNC (SEQ ID NO:2) and/or the CdS-BP comprises the sequence SLTPLTTSHLRS (SEQ ID NO:3).

In some embodiments, the curli fibers bind to and nucleate inorganic nanomaterials. In certain embodiments, one or more of the inorganic nanomaterials includes gold nanoparticles, silver nanoparticles, zinc sulfate, cadmium sulfate, iron oxide, cobalt oxide, cobalt platinum, iron platinum or quantum dots. In some embodiments, tetra-glutamate peptides are integrated into one or more curli fibers. In some embodiments, a conductive cytochrome is displayed on the surface of one or more curli fibers. In certain embodiments, the conductive cytochrome is cytochrome b562.

In some embodiments, the cell expresses one or more components of the mtrCAB complex. In certain embodiments, the one or more components of the mtrCAB complex is expressed under the control of an inducible promoter.

In some embodiments, the polymers exhibit a nanopattern selected from the group consisting of an interdigitated pattern, a bipartite pattern, a multi-segmented pattern, and a repeating multi-segmented pattern. In certain embodiments, the polymers exhibit an interdigitated pattern through the simultaneous expression of different polymer subunits from inducible promoters. In certain embodiments, the polymers exhibit a bipartite pattern through the expression of different polymer subunits under the control of two inducible promoters which are activated in sequential order or under the control of two outputs of a toggle switch.

In certain embodiments, the polymers exhibit a multi-segmented pattern through the expression of different polymer subunits under the control of more than two inducible promoters which are sequentially activated. In certain embodiments, the polymers exhibit a repeating multi-segmented pattern by coupling the production of the different polymer subunits to genetic oscillators.

In some embodiments, expression of the polymer is regulated by a synthetic genetic circuit. In some embodiments, the synthetic genetic circuit is a synthetic quorum sensing circuit. In certain embodiments, the synthetic genetic circuit is a synthetic light-sensing circuit. In some embodiments, the synthetic genetic circuit is a synthetic magnetic field-sensing circuit. In certain embodiment, the magnetic field-sensing circuit incorporates crytochromes. In some embodiments, the synthetic genetic circuit is a synthetic heat sensing circuit. In certain embodiments, the synthetic heat sensing circuit is a heat sensitive toggle switch. In some embodiments, the synthetic genetic circuit is a synthetic electrical field-sensing circuit. In certain embodiments, the synthetic electrical field-sensing circuit incorporates a voltage-sensitive ion channel.

In some embodiments, expression of the polymers is regulated by UV-inducible toggle switches and/or visible-light-inducible promoters. In some embodiments, the cell expresses a Single Invertase Memory Module (SIMM).

In some embodiments, the biological nanostructure is conductive. In certain embodiments, the biological nanostructure is a component of a conductive biofilm. In some embodiments, the biological nanostructure is a component of an electrical signaling pathway. In some embodiments, the biological nanostructure can sense and respond to magnetic fields, heat and/or light. In some embodiments, the biological nanostructure is a component of a self-healing biomaterial and/or self-healing armor. In some embodiments, the biological nanostructure is used for repair of nanomaterials after trauma. In some embodiments, the biological nanostructure is a component of a microbial fuel cell. In some embodiments, the biological nanostructure is used for drug delivery, computation or energy storage.

Further aspects if the invention relate to methods for producing a biological nanostructure in vivo, the method comprising providing a cell that is genetically engineered to express one or more polymers which assembles into a biological nanostructure on the surface of the cell, outside the cell or inside the cell.

In some embodiments, one or more of the polymers is modified. In some embodiments, the cell is a bacterial cell, fungal cell (including a yeast cell) or a mammalian cell. In some embodiments, the polymer is an amyloid, a pili or a flagella. In some embodiments, one or more of the modified polymers comprises one or more heterologous polypeptide domains. In some embodiments, one or more of the heterologous polypeptide domains binds to one or more inorganic nanomaterials, such as metals or metal nanoparticles. In certain embodiments, the one or more of the metals or metal nanoparticles includes gold nanoparticles, silver nanoparticles, zinc sulfate, cadmium sulfate, iron oxide, cobalt oxide, cobalt platinum, iron platinum or quantum dots.

In some embodiments, one or more of the heterologous polypeptide domains binds to other polymers or protein structures. In some embodiments, expression of the polymers is under the control of inducible promoters. In some embodiments, the expression and/or composition of polymers, or subunits thereof, is temporally regulated. In some embodiments, the cell expresses at least two different polymers, and the different polymers, or subunits thereof, are expressed with different heterologous polypeptides.

In some embodiments, the cell is a bacterial cell. In some embodiments, the cell is of the *Escherichia, Salmonella, Pseudomonas, Bacillus, Citrobacter, Shigella* or *Enterobacter* genus. In certain embodiments, the cell is an *Escherichia coli* (*E. coli*) cell, a *Pseudomonas aeruginosa* (*P. aeruginosa*) cell or a *Bacillus subtilis* (*B. subtilis*) cell. In certain embodiments, the cell is an *E. coli* cell. In certain embodiments, the amyloid fiber is a curli fiber.

In some embodiments, the cell expresses a csgBAC and/or a csgDEFG operon and wherein one or more components of the csgBAC and/or csgDEFG operons is genetically engineered. In some embodiments, one or more components of the csgBAC and/or csgDEFG operons is expressed on a plasmid. In some embodiments, csgA and/or csgB is expressed on a plasmid under the control of an inducible promoter, such as pLtetO or pLlacO, a LacI riboregulator, a TetR riboregulator or a LuxR riboregulator.

In some embodiments, one or more heterologous polypeptide domains are attached to CsgA. In certain embodiments, one or more heterologous polypeptide domains are attached to the C-terminus of CsgA. In some embodiments, csgA and/or csgB are genetically engineered to express charged residues, such as glutamic acid. In some embodiments, CsgA, CsgB and Maltose-binding protein (MBP) are expressed in the cell under the control of an inducible promoter.

In some embodiments, the polymers are genetically engineered to promote release of the polymers from the cell. In some embodiments, exogenous D-amino acids enable the detachment of amyloid fibers from the cell surface. In certain embodiments, one or more of the D-amino acids is D-leucine, D-methionine, D-tyrosine or D-tryptophan. In certain embodiments, the cells overexpresses a gene encoding for an enzyme that converts L-amino acids to D-amino acids. In certain embodiments, the gene encoding for an enzyme that converts L-amino acids to D-amino acids is selected from the group consisting of ylmE, racX, alr, dadX, murI, yhfX and ygeA.

In some embodiments, one or more inorganic-binding peptides is incorporated into one or more of the curli fibers. In certain embodiments, the inorganic is a metal or a semiconductor. In some embodiments, one or more of the metal-binding peptides is a gold-binding peptide (Au-BP). In some embodiments, the Au-BP is fused to CsgA. In certain embodiments, the Au-BP is fused to the C terminus of CsgA. In certain embodiments, the Au-BP comprises the sequence LKAHLPPSRLPS (SEQ ID NO:1). In some embodiments, one or more of the metal-binding peptides is a ZnS-binding peptide (ZnS-BP) and/or a CdS-binding peptide (CdS-BP). In certain embodiments, the ZnS-BP comprises the sequence CNNPMHQNC (SEQ ID NO:2) and/or the CdS-BP comprises the sequence SLTPLTTSHLRS (SEQ ID NO:3).

In some embodiments, the curli fibers bind to and nucleate inorganic nanomaterials. In certain embodiments, one or more of the inorganic nanomaterials includes gold nanoparticles, silver nanoparticles, zinc sulfate, cadmium sulfate, iron oxide, cobalt oxide, cobalt platinum, iron platinum or quantum dots. In some embodiments, tetra-glutamate peptides are integrated into one or more curli fibers. In some embodiments, a conductive cytochrome is displayed on the surface of one or more curli fibers. In some embodiments, the conductive cytochrome is cytochrome b562. In some embodiments, the cell expresses one or more components of the mtrCAB complex. In some embodiments, the one or more components of the mtrCAB complex is expressed under the control of an inducible promoter.

In some embodiments, the surface-displayed polymers exhibit a nanopattern selected from the group consisting of an interdigitated pattern, a bipartite pattern, a multi-segmented pattern, and a repeating multi-segmented pattern. In certain embodiments, the polymers exhibit an interdigitated pattern through the simultaneous expression of different polymer subunits from inducible promoters. In certain embodiments, the polymers exhibit a bipartite pattern through the expression of different polymer subunits under the control of two inducible promoters which are activated in sequential order or under the control of two outputs of a toggle switch.

In certain embodiments, the polymers exhibit a multi-segmented pattern through the expression of different polymer subunits under the control of more than two inducible promoters which are sequentially activated. In certain embodiments, the polymers exhibit a repeating multi-segmented pattern by coupling the production of the different polymer subunits to genetic oscillators.

In some embodiments, expression of the polymer is regulated by a synthetic genetic circuit. In some embodiments, the synthetic genetic circuit is a synthetic quorum sensing circuit. In some embodiments, the synthetic genetic circuit is a synthetic light-sensing circuit and/or a magnetic field-sensing circuit. In certain embodiments, the magnetic field-sensing circuit incorporates cryptochromes. In some embodiments, the synthetic genetic circuit is a synthetic heat-sensing circuit, such as a heat-sensitive toggle switch.

In some embodiments, the synthetic genetic circuit is a synthetic electrical field-sensing circuit. In certain embodiments, the electrical field-sensing circuit incorporates a voltage-sensitive ion channel. In some embodiments, expression of the polymer is regulated by UV-inducible toggle switches and/or visible-light-inducible promoters. In some embodiments, the cell expresses a Single Invertase Memory Module (SIMM).

In some embodiment, the biological nanostructure is conductive. In certain embodiments, the biological nanostructure is a component of a conductive biofilm. In some embodiments, the biological nanostructure is a component of an electrical signaling pathway. In some embodiments, the biological nanostructure can sense and respond to magnetic fields, heat and/or light. In some embodiments, the biological nanostructure is a component of a self-healing biomaterial and/or self-healing armor. In some embodiments, the biological nanostructure is used for repair of nanomaterials after trauma. In some embodiments, the biological nanostructure is a component of a microbial fuel cell. In some embodiments, the biological nanostructure is used for drug delivery, computation or energy storage.

In some embodiments, the expression and/or composition of the polymers, or subunits thereof, changes in response to an environmental cue. In certain embodiments, the environmental cue is a change in cell density.

Further aspects of the invention relate to a combination of two or more of the cells associated with the invention, wherein the cells are spatially patterned. In some embodiments, the cells are spatially patterned through the creation of a standing wave in liquid media.

Each of the features of the invention can encompass various embodiments of the invention. It is, therefore, anticipated that each of the features of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows engineered *E. coli* curli fibers containing synthetic CsgA major curli structural subunits which are nucleated by synthetic CsgB nucleators.

Heterologous polypeptides can be attached to the N-terminal, C-terminal, or internal sites of the engineered amyloid subunits. Expression of these engineered amyloid subunits inside engineered cells enables the establishment of surface-displayed artificial amyloids with nanoscale heterologous polypeptides that can have different functionalities. FIG. 1B shows that simultaneous expression of different amyloid subunits can create synthetic amyloid fibers that have inter-digitated, interspersed, and different functional polypeptide domains. FIG. 1C shows that inducible temporal expression of different amyloid subunits can create linear patterns with varying lengths. FIG. 1D shows that by designing amyloid subunits to have specific binding properties, capped fibers can be created that can no longer extend. FIG. 1E shows that by designing amyloid subunits to have specific binding properties, fibers can be created that are forced to interdigitate in regular, repeating patterns. FIG. 1F shows that heterologous polypeptide domains can be attached N-terminal, C-terminal or internal to the amyloid subunits. Heterologous polypeptide domains can also be attached to internal sites in the amyloid subunits, which can create even more complex nanostructures. FIG. 1G shows that by designing or selecting the heterologous polypeptide domains to have metal-binding affinity, new materials can be created with nanostructured metals.

FIG. 2A shows complex nanostructures surrounding a cell. FIG. 2B shows that multicellular pattern formation with the synthetic amyloid fibers can lead to complex patterns from the nanoscale to the macroscale.

FIG. 6 depicts the structural components of curli in *E. coli*. FIG. 6A shows that CsgA, the major curlin subunit, contains an N-terminal Sec signal sequence, a 22 amino acid (a.a.) segment that mediates secretion (labeled N22), and five imperfect repeating domains that form the amyloid core (labeled R1 to R5) (Barnhart et al., (2006) *Annu Rev Microbiol* 60:131). Conserved residues within the repeats are depicted by boxes. Sequences correspond to SEQ ID NOs:70-76, respectively. FIG. 6B shows that CsgB, the minor curlin subunit, shares a similar design as CsgA. Conserved residues within the repeats are depicted by boxes. Sequences correspond to SEQ ID NOs:124-130, respectively. FIG. 6C shows a structural prediction for the CsgA protein contains five stacked strand-loop-strand motifs which are mediated by conserved residues. Id. C5a, C5b, C5c, Cyd, and C5e in the figure correspond to repeats R1, R2, R3, R4, and R5, respectively. Conserved residues in CsgA include serine, glutamines, glycines, and alanines (adapted from Barnhart et al., (2006) *Annu Rev Microbiol* 60:131).

FIG. 7A shows that peptide arrays were constructed by tiling sequential overlapping 20-mer peptides spanning CsgA and CsgB. FIG. 7B-C reveal that relative fluorescence of Alexa-labeled full-length CsgA bound to peptide arrays show that CsgA nucleation is facilitated by three regions in CsgB which contain hydrophobic residues (underlined). Sequences within FIG. 7C correspond to SEQ ID NOs:131-133. FIG. 7D shows that these peptides, bound to maleimide plates, facilitate in vitro assembly of soluble CsgA into amyloids as monitored by ThT fluorescence. $CsgB_{130-149}$ enhances CsgA assembly (0.1 μM, 0.25 μM, and 0.5 μM shown as lines 3, 4 and 5, respectively) with kinetics similar to seeded assembly (i.e., first order kinetics). CsgA fiber assembly with plate-bound $CsgB_{62-81}$ (line 2) and CsgA alone (line 1) exhibit lag phases even at high concentrations (0.5 μM).

FIG. 10A shows that *E. coli* ΔcsgA::kanR plus plasmids expressing wild-type CsgA or CsgA with a C-terminal fusion to the FLAG tag (CsgA-FLAG) form red colonies (depicted by "R") on YESCA agar plates containing CR indicating amyloid fiber formation. In contrast, *E. coli* ΔcsgA::kanR exhibits a white phenotype. FIG. 10B shows TEM confirming that curli fibers are formed by wild-type CsgA subunits. FIG. 10C shows TEM confirming that curli fibers are formed by CsgA-FLAG subunits. FIG. 10D shows TEM confirming that *E. coli* ΔcsgA::kanR does not produce curli.

FIG. 11 shows TEM images of curli. FIG. 11A shows wild-type curli expressed from *E. coli*. FIG. 11B shows curli fibers expressed from *E. coli* with the FLAG peptide inserted between the N22 and the R1 repeat regions in CsgA.

FIG. 14 shows TEM of gold-binding bacterial curli nanowires. FIG. 14A shows that fibers displaying a gold-binding peptide (Au-BP) at the C-terminal of CsgA are lined with 5 nm gold nanoparticles. FIG. 14B shows that fibers displaying the FLAG affinity peptide do not bind to 5 nm gold nanoparticles in great numbers.

FIG. 15 shows TEM of bacterial curli nanowires that nucleate and bind to zinc sulfate (ZnS). FIG. 15A shows that fibers displaying a ZnS-binding peptide (ZnS-BP) at the C-terminal of CsgA can nucleate ZnS formation that coats the curli amyloids. FIG. 15B shows that wild-type curli fibers do not nucleate ZnS formation.

FIG. 17A shows that for interdigitated nanowires, two different types of CsgA subunits (shown in light and intermediate grey) can be simultaneously expressed. FIG. 17B shows that for bipartite nanowires, two different types of CsgA subunits (shown in light and intermediate grey) can be sequentially expressed to create nanowires that have one type of subunit at one end and another type of subunit at the opposite end. This can be achieved by coupling the expression of different curli subunits to synthetic inducible promoters or to the distinct outputs of genetic toggle switches (Gardner et al., (2000) *Nature* 403:339). FIG. 17C shows that for multi-segmented nanowires, multiple types of CsgA subunits (shown in light, intermediate and dark grey) can be sequentially expressed. FIG. 17D shows that by connecting the temporal expression of different CsgA subunits to oscillatory gene circuits, autonomously generated repeating nanowire patterns can be generated.

FIG. 18A shows the use of quorum-sensing circuits that enable bacteria to self-organize to produce bacterial nanowires in spatially segregated regions. FIG. 18B shows the connection of synthetic circuits, such as toggle switches and recombinase-based switches, which are responsive to visible or UV light, to the expression of curli subunits. This will enable the use of external masks to define desirable material patterns.

FIG. 20 presents a table summarizing primers used to insert 7xHis tags throughout the CsgA protein.

FIG. 25 presents electron microscopy images. FIG. 25A shows a wild type CsgA negative control and FIG. 25B shows a wild type CsgA negative control.

FIG. 29A presents histidine tagged curli fibers which bind NiNTA-conjugated gold nanoparticles in a binding buffer consisting of 0.5M NaCl, 100 mM imidazole and 0.2 v/v % Tween 20; FIG. 29B presents wildtype unmodified curli fibers which do not bind NiNTA-conjugated gold nanoparticles in a binding buffer consisting of 0.5M NaCl, 100 mM imidazole and 0.2 v/v % Tween 20.

FIG. 32 presents results of a patterning experiment. FIG. 32C and FIG. 32F show that copolymers contain some segments which bind NiNTA-conjugated gold nanoparticles via histidine tags, and some segments which do not. This is in contrast to polymers consisting of only CsgA, which do not bind NiNTA-conjugated gold nanoparticles to a significant degree (FIG. 32A, D) and polymers consisting of only CsgA-7xHis, which bind the particles uniformly along their length (FIG. 32B, E).

FIG. 33A shows that aTc induced riboregulators allow curli fiber formation in the presence of aTc, while FIG. 33B shows that aTc induced riboregulators do not allow curli fiber formation in the absence of aTc. Similarly, AHL induced riboregulators allow curli fiber formation in the presence of AHL (FIG. 33C), but not in its absence (FIG. 33D).

FIG. 34 presents data on regulated curli fiber formation in systems comprising multiple cell types. In FIG. 34A, Cell 1 (containing an aTc riboregulated CsgA (CmR) plasmid and an aTc induced luxI (AmpR) plasmid) was grown in Carb and induced with aTc, which drives CsgA expression from aTc ribo CsgA (CmR) and AHL production via aTc induced luxI (AmpR). The number of cells bearing CmR does not increase significantly with time since there is no selection for CmR, so the CmR plasmid is not propagated in most cell division events. By contrast, the number of cells with AmpR plasmid grew exponentially and the AHL concentration rapidly increased. After 26 h, some curli fibers are visible, and they do not bind NiNTA gold particles (FIG. 34A). In FIG. 34B, Cell 2 (containing an AHL ribo CsgA-7xHis (AmpR) plasmid) was grown in Carb and induced with aTc.

The number of cell bearing AHL ribo CsgA7×His (AmpR) plasmid grew exponentially, but no curli was produced since there was no AHL present. After 26 h, no curli fibers were seen (FIG. 34B).

FIG. 35 presents data on regulated curli fiber formation in systems comprising multiple cell types. In FIG. 35A, Cell 1 (containing an aTc ribo CsgA (CmR) plasmid and an aTc induced luxI (AmpR)) is co-cultured with Cell 2 (containing an AHL ribo CsgA-7×His (AmpR) plasmid) in Carb and induced with aTc. Early on, there is CsgA curli production from aTc ribo CsgA (CmR), but not enough AHL has been made via aTc induced luxI (AmpR) to drive CsgA7×His curli production from AHL ribo CsgA7×His (AmpR)—the curli formed early on at 8 hour and 12 hour timepoints do not bind NiNTA gold particles (FIG. 35A, B). Later, since there is selection for AmpR but not for CmR, the number of AHL ribo CsgA7×His (AmpR) overwhelm aTc ribo CsgA (CmR). At the same time AHL concentration has also reached high levels, allowing induction of CsgA7×His from AHL ribo CsgA7×His (AmpR) at 16 hour and 24 hour timepoints (FIG. 35C, D). At this time, the majority of subunits available to form fibers is CsgA-7×His.

Figure 36:
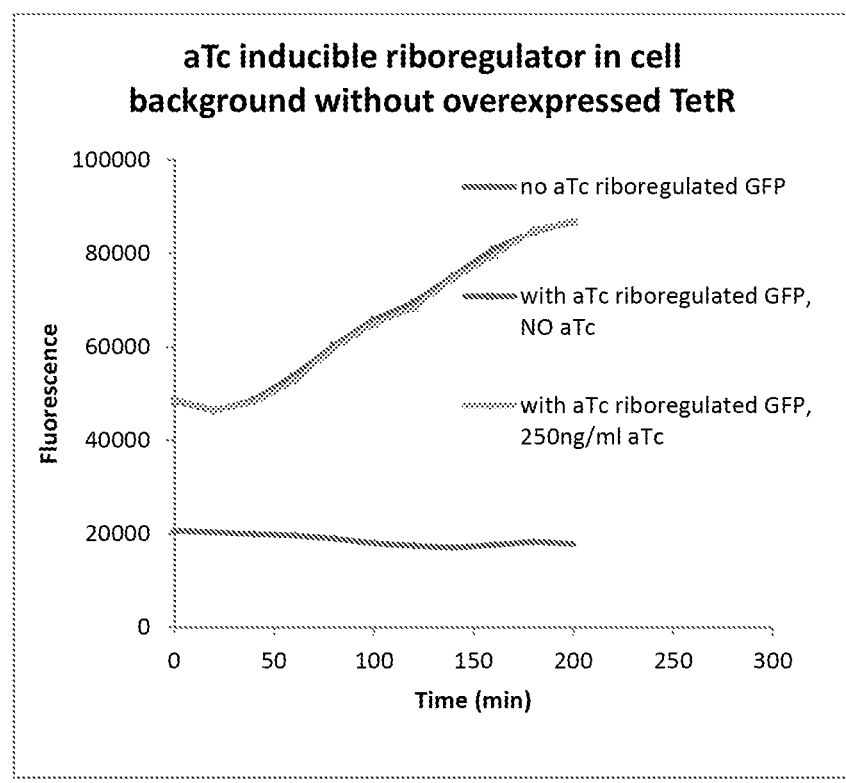

FIG. 36 presents data showing that without overexpressed TetR repressor, the aTc induced riboregulator can be leaky. GFP under the control of this riboregulator was expressed whether or not aTc inducer was present.

Figure 37:
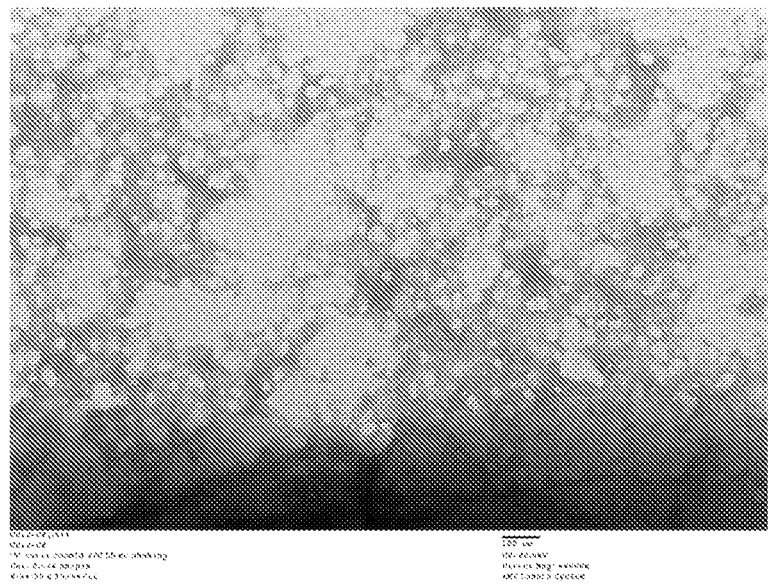

FIG. 37 presents data showing that cell strains which do not have the OmpR234 mutation, even ones with modifications such as overexpression of the entire curli operon (Cherny et al. (2005) *Journal of Molecular Biology* 352: 245), do not form distinct fibers in liquid media (FIG. 37).

Figure 38:
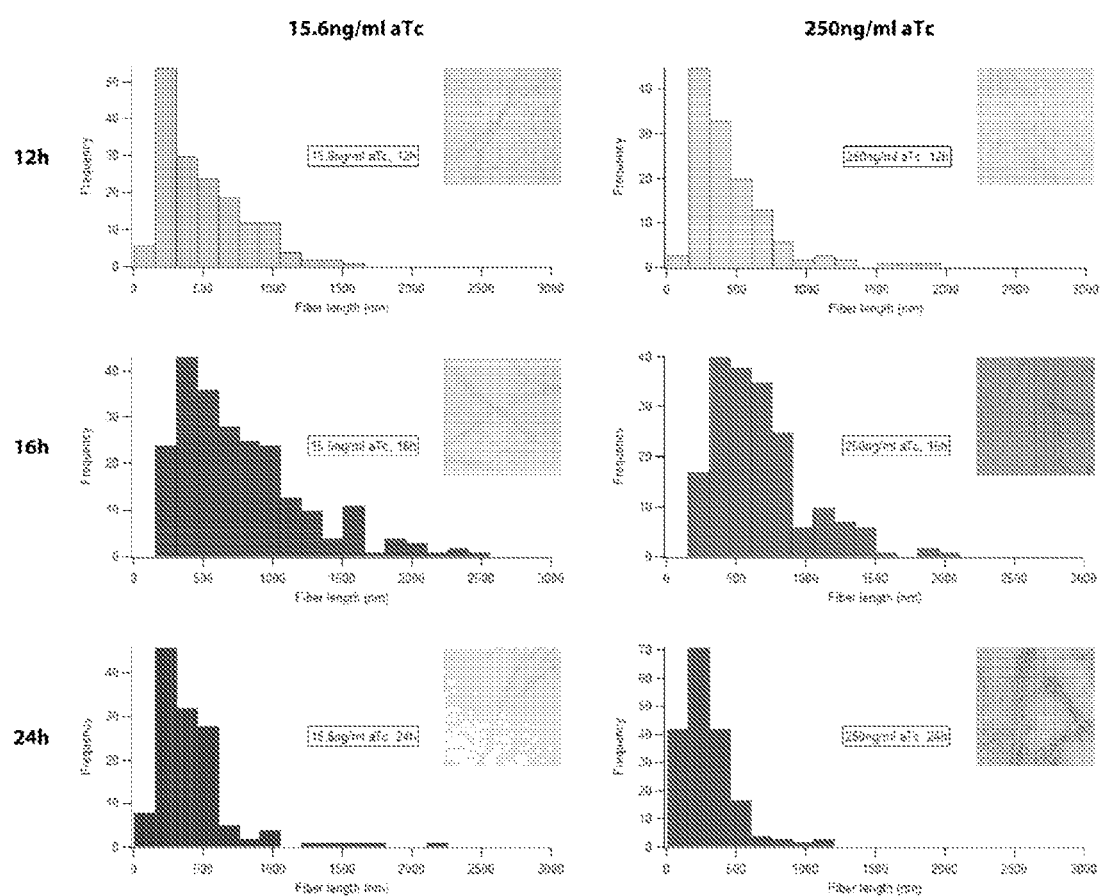

FIG. 38 presents data from mapping the distribution of curli fiber segment lengths as a function of inducer concentration and growth time. In some embodiments, the distribution of curli fiber lengths was more strongly dependent on growth time than on inducer concentration. As cells were grown with inducer for increasing time, the fibers got longer and also became more heterogeneous in length; when allowed to grow even longer, the fibers underwent structural change and their average length decreased.

Figure 39:
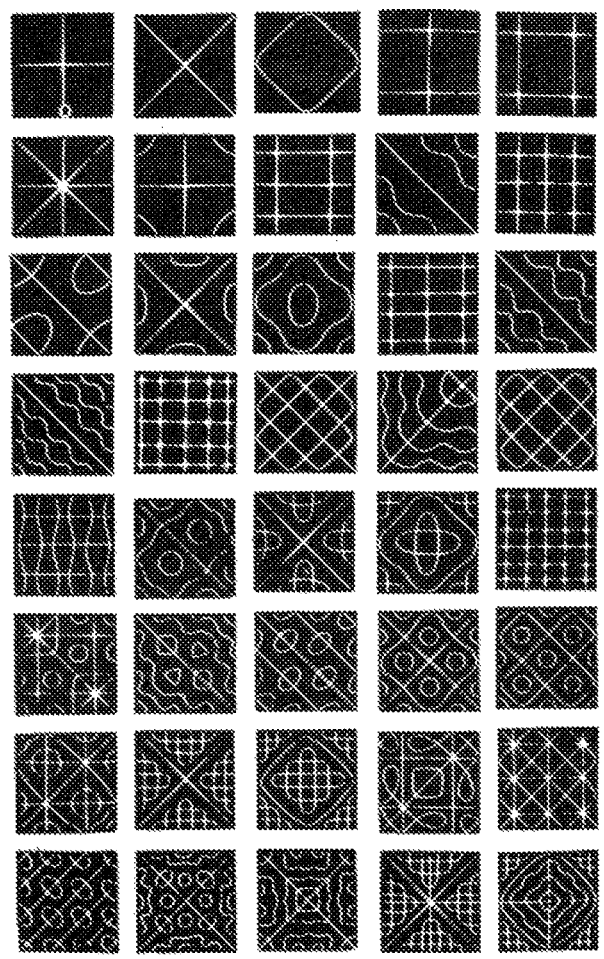

FIG. 39 presents non-limiting examples of patterns possible with spatial patterning techniques based on creation of standing waves in a container with rectangular boundary conditions. Such waves create cell-accumulating pressure nodes and antinodes in intricate patterns. This Figure was reproduced from: physics.ucla.edu/demoweb/demomanual/acoustics/effects_of_sound/chladniarray.jpg.

Figure 40:
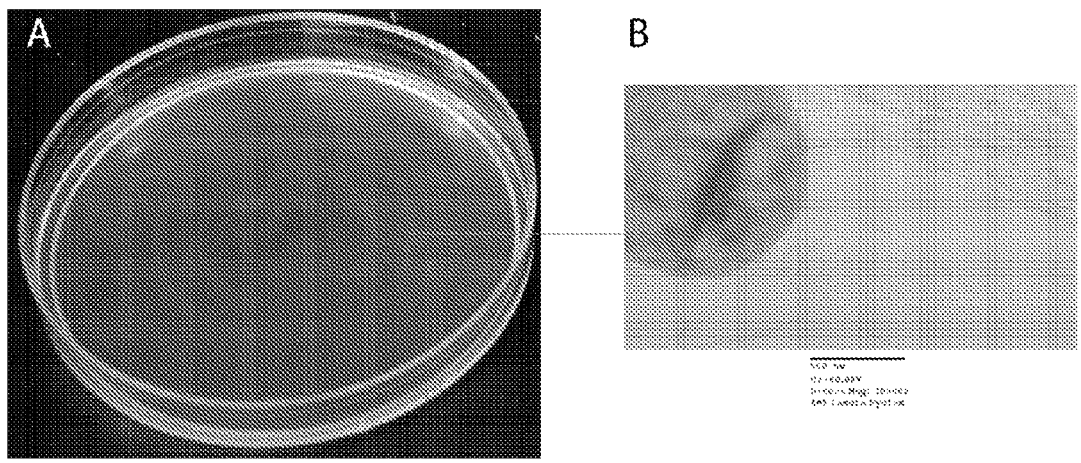

FIG. 40 presents data demonstrating pattern formation. 15 ml of M63 minimal media was placed with $5 \times 10^7$/ml OmpR234 *E. coli* cells in a 100 mm Petri dish, then incubated at 30° C. for 28 h on the top self of a VWR 1585 Shaking Incubator set at 300 rpm. The shaking action created concentric ring standing waves in the Petri dish with a wavelength ~1.67 cm, and such waves created concentric ring pattern deposits of cells at a spacing of ~0.83 cm (FIG. 40A). Examination of the material in the rings under TEM revealed curli fiber formation (FIG. 40B).

Figure 41:
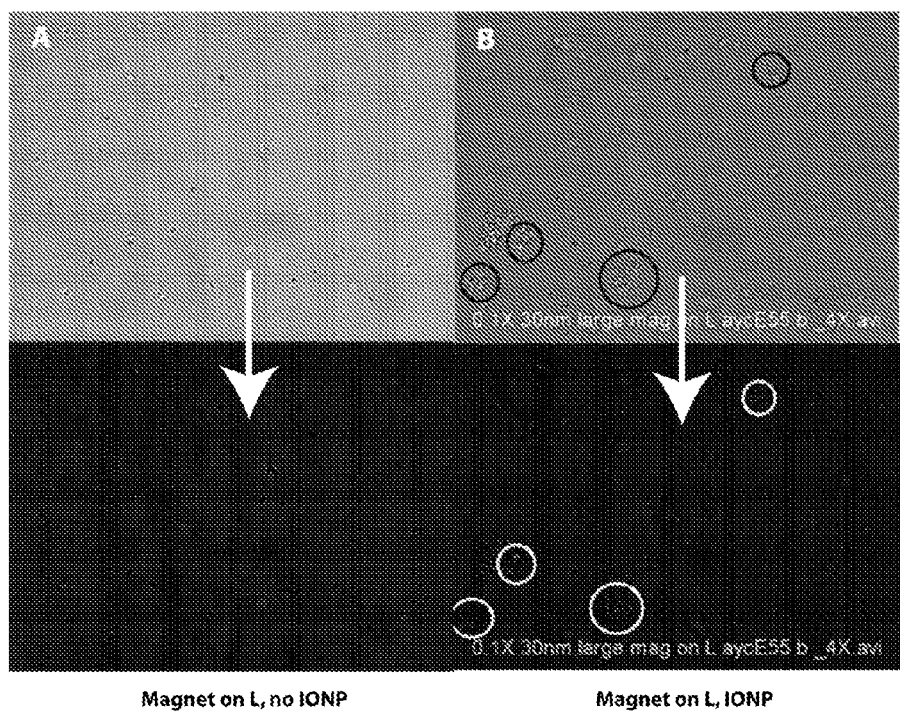

FIG. 41 presents data showing that surface-attached fibers with affinity tags or natural affinity for biomaterials can be used to bind paramagnetic nanoparticles, allowing cells to interface with magnetic fields. Curli fiber-displaying cells were incubated with 10 nM 30 nm iron oxide nanoparticles (IONPs) for at least 1 hour, allowing the cells to move toward an N42 neodynium magnet as observed under a microscope (FIG. 41B, FIG. 42B). Negative control cells (CsgA KO), which do not express fibers, when incubated for at least 1 hour with 10 nM 30 nm IONPs did not move (FIG. 41A, FIG. 42A).

Figure 42:
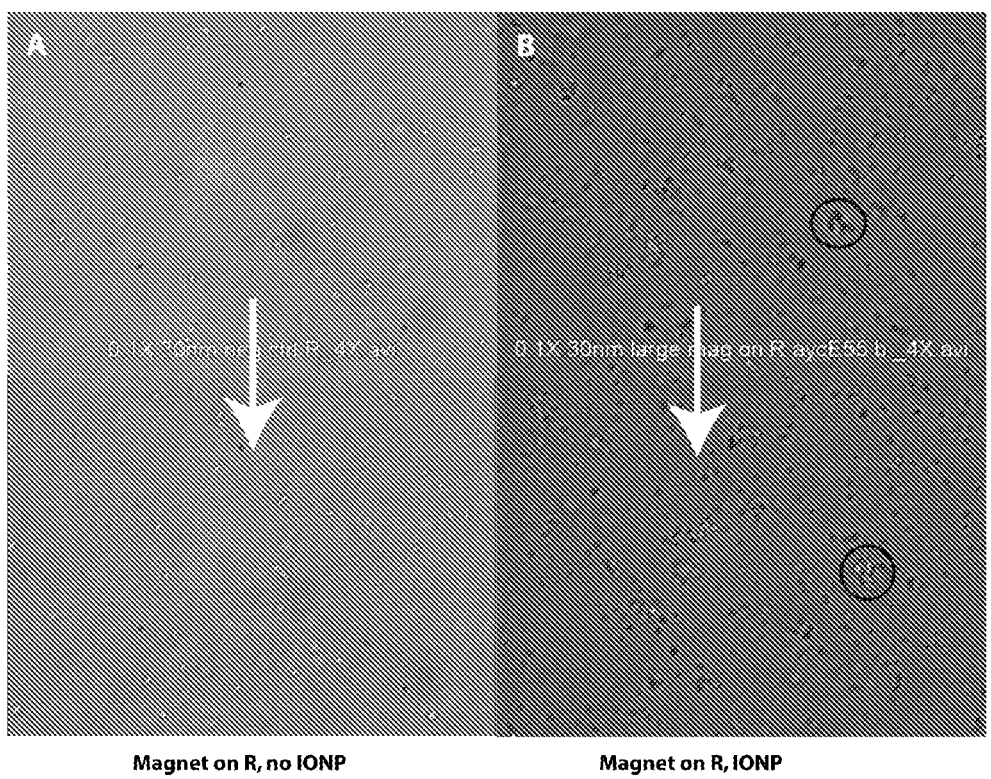

FIG. 42 demonstrates that surface-attached fibers with affinity tags or natural affinity for biomaterials can be used to bind paramagnetic nanoparticles, allowing cells to interface with magnetic fields. Curli fiber-displaying cells were incubated with 10 nM 30 nm iron oxide nanoparticles (IONPs) for at least 1 hour, allowing the cells to move toward an N42 neodynium magnet as observed under a microscope (FIG. 41B, FIG. 42B). Negative control cells (CsgA KO), which do not express fibers, when incubated for at least 1 hour with 10 nM 30 nm IONPs did not move (FIG. 41A, FIG. 42A).

Figure 43:
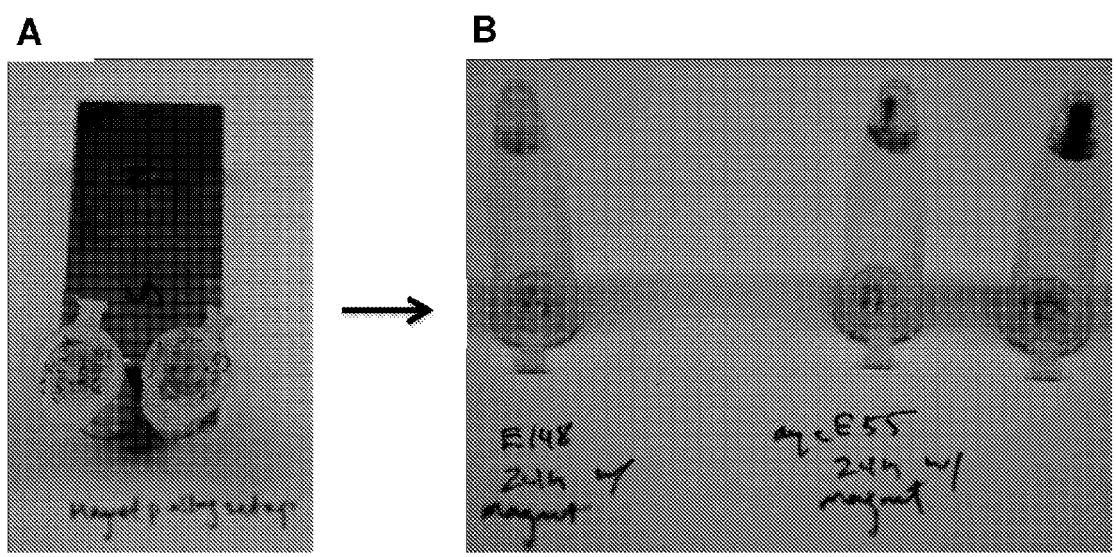

FIG. 43 presents data from a magnetic separation experiment. FIG. 43A depicts contact with the magnet. FIG. 43B shows that at the macroscale, incubating fiber-displaying cells with IONP allowed magnetic separation of cells to a pellet, leaving the supernatant clear. Samples of cells not displaying fibers incubated with IONP did not separate and the supernatant remained cloudy.

Figure 44:
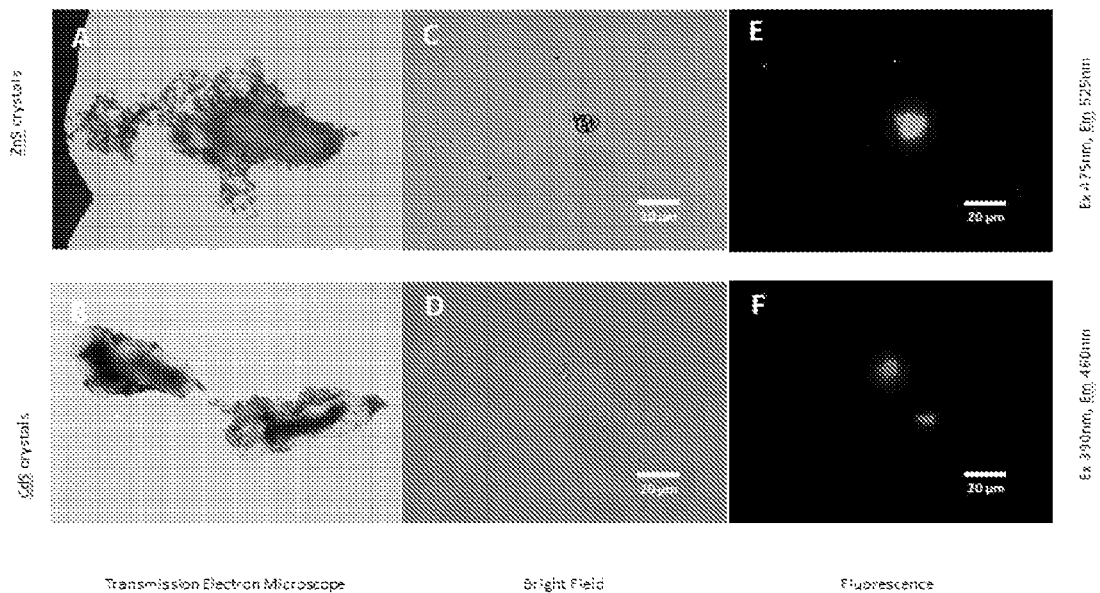

FIG. 44 presents electron microscope (A, B), transmission light microscope (C, D), and fluorescence light microscope (E, F) images of CdS and ZnS grown on fibers displayed on cells.

DETAILED DESCRIPTION

Provided herein is an innovative and broad platform for engineering multifunctional biological nanowires that can be interfaced with non-living materials and patterned at the nanoscale, microscale, and macroscale by coupling nanowire synthesis with synthetic gene circuits. Biological nanowires described herein are based on biologically synthesizable polymers, such as functional amyloid fibers, produced by cells. These polymers optionally are functionalized with surface-displayed peptides to bind and nucleate inorganic materials and to achieve novel properties such as conductivity. Self-assembly of these polymers, such as amyloid nanowires, is based on amino-acid interactions between individual subunits that are programmable via the underlying genetic code. By connecting the expression of polymer subunits, such as amyloid subunits, to synthetic gene circuits and engineering the primary sequence of these subunits, these nanostructures can be functionalized and patterned to a degree that is unprecedented compared with other strategies. This synthetic-biology-based platform will enable practical applications including conductive biofilms for enhanced power density from microbial fuel cells, conductive bacteria with electrical signaling pathways, bacterial sensors that detect magnetic fields, and biomaterials with self-healing capabilities.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Aspects of the invention relate to recombinant cells. As used herein, "recombinant cell," "genetically engineered cell," and "synthetic cell" are used interchangeably to refer to a cell that has been genetically altered to express one or more nucleic acid sequences. The cell may or may not also endogenously express the same nucleic acid sequences.

Aspects of the invention relate to cells that express biologically synthesizable polymers. As used herein, "biologically synthesizable polymer" and "polymer" are used interchangeably to refer to a molecule that is composed of repeating structural units and that can be synthesized by a cell. Several non-limiting examples of polymers that are compatible with aspects of the invention are amyloids, pili and flagella. As used herein, an "amyloid" refers to an aggregate of proteins or peptides with cross-beta structure and fibrillar morphology. Amyloid fiber structure consists of β-strands which are perpendicular to the fiber axis and β-sheets which stack parallel to the fiber axis.

Aspects of the invention involve regulation of expression of modified polymers, such as amyloid fibers. Expression of a modified polymer, such as an amyloid fiber, can be placed under the control of a constitutive promoter or an inducible promoter. It should be appreciated that a wide variety of constitutive and inducible promoters are compatible with aspects of the invention and the selection of a suitable promoter would be guided by factors such as the cell type and the desired level of induction of expression. Non-limiting examples of promoters are available at the Registry of Standard Biological Parts (http://partsregistry.org/Promoters/Catalog). In some embodiments, expression of a modified polymer, or subunit thereof, such as an amyloid fiber, or subunit thereof, is temporally regulated. In some embodiments, expression of a modified polymer, or subunit thereof, such as an amyloid fiber, or subunit of, is spatially regulated within a cell.

According to aspects of the invention, recombinant cell(s) that express one or more polymers, such as amyloid fibers, including surface-displayed amyloid fibers, and the use of such cells in producing nanowires, are provided. It should be appreciated that any kind of polymer expressed by a cell can be compatible with aspects of the invention. In some non-limiting embodiments, the cell is a bacterial cell, a fungal cell (including yeast cells), or a mammalian cell.

Figure 5:
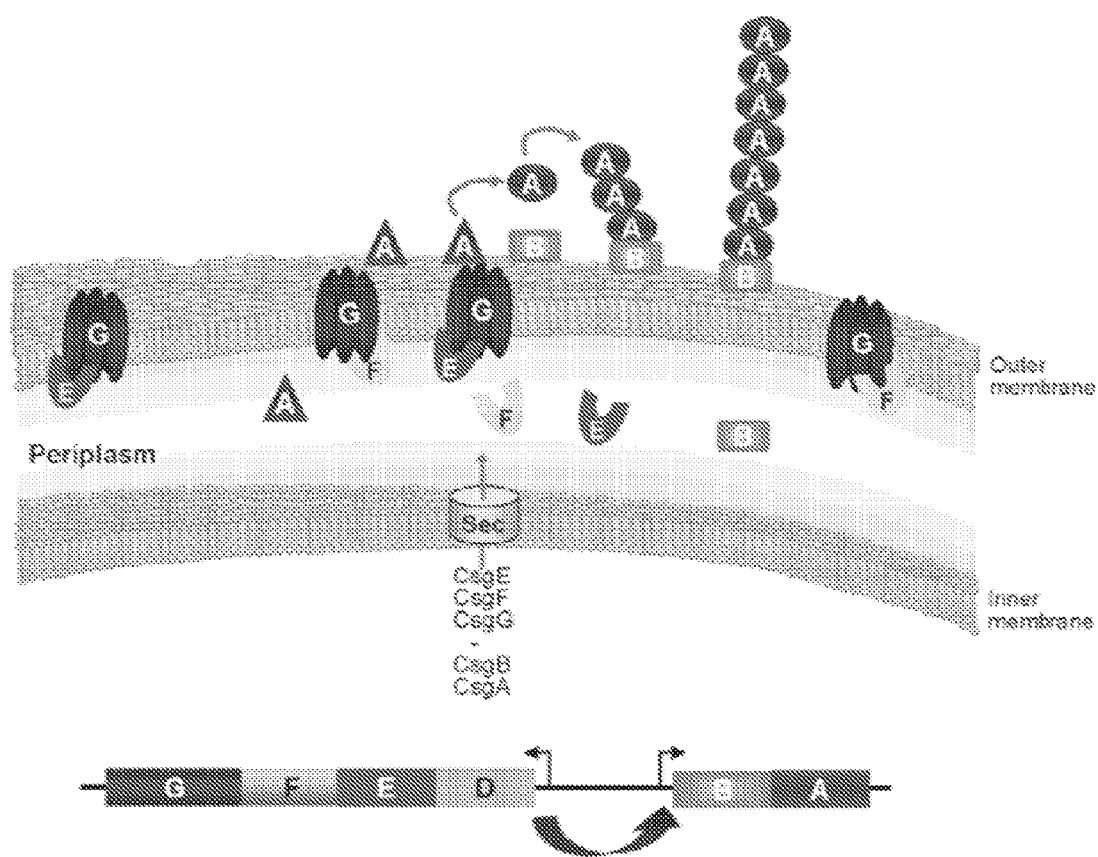
FIG. 5 presents a model for curli expression and fiber formation in *E. coli* (adapted from Barnhart and Chapman (2006) *Annu Rev Microbiol* 60:131). CsgB serves as a cell-associated nucleator that polymerizes curli fibers principally composed of CsgA subunits. CsgG forms an outer-membrane complex with the chaperone-like CsgE and CsgF proteins to export CsgA and CsgB to the cell surface. CsgD positively regulates the expression of CsgB and CsgA.

In certain embodiments, the cell is an *E. coli* cell and the amyloid fiber is a curli fiber. Curli amyloid assembly is depicted in FIG. 5. In some embodiments, curli fibers are optimally expressed naturally in conditions that include temperatures below 30° C., low osmolarity, nutrient limitation, stationary phase, and a microaerophilic environment (Barnhart et al., (2006) *Annu Rev Microbiol* 60:131).

The *E. coli* curli operon comprises csgBAC and csgDEFG. The csgBAC transcriptional unit is positively regulated by CsgD and negatively regulated by the CpxA/CpxR system and Rcs, both of which are responsive to membrane stress. Id. Positive regulators of the csgDEFG transcriptional unit include the OmpR/EnvZ system, RpoS, Crl, MlrA, and IHF while negative regulators include the CpxA/CpxR system and the Rcs system. Id.

CsgA, which is the major curlin subunit, is secreted as a soluble protein. CsgA is polymerized into fibrils by CsgB, which is the minor curlin subunit and is an outer-membrane-associated protein. As shown in FIG. 6, CsgA and CsgB share sequence homology and form a cross-0 sheet complex with five repeating strand-loop-strand structures. Both CsgA and CsgB can form amyloid fibrils on their own (Shewmaker et al., (2009) *J Biol Chem* 284:25065; Barnhart et al., (2006) *Annu Rev Microbiol* 60:131).

CsgD is a positive regulator of csgBAC expression. CsgE is a chaperone-like protein thought to be involved in the stability of CsgA and CsgB. CsgF is a chaperone-like protein which is secreted to the cell surface and is involved in associating CsgB with the cell surface helping CsgB nucleate curli fiber formation (Nenninger et al., (2009) *Proc Natl Acad Sci USA* 106:900). CsgG is a lipoprotein which participates in the secretion of CsgA, CsgB, and CsgF (Id.; Epstein et al., (2009) *J Bacteriol* 191:608). CsgG interacts with the N22 domain of CsgA (FIG. 6A) to mediate secretion to the cell surface (Chapman et al., (2002) *Science* 295:851).

It should be appreciated that the genes encoding for the amyloid fibers associated with the invention can be obtained from a variety of sources. For example, a non-limiting example of a homologous operon to the *E. coli* Csg operons includes the agf operon in *Salmonella* (Darwin et al. (1999) *Clin Microbiol Rev* 12:405-428). Related operons have also been identified in *Pseudomonas* (Dueholm et al. (2010) *Mol Microbiol* Epub June 21) and in *Bacillus subtilis* (Romero et al., (2010) *Proc Natl Acad Sci USA* 107:2230-2234), comprising the fap and Tas operons, respectively.

Functional amyloids have also been identified in yeast. For example, in *Candida albicans*, the Als Adhesins have been demonstrated to form amyloid-like fibers (Otoo et al., (2008) *Eukaryotic Cell* 7:776-782). Amyloid formation has also been demonstrated for adhesion proteins in *Saccharomyces cerevisiae* (Ramsook et al. (2010) *Eukaryotic Cell* 9:393-404). Rep1-1 to Rep1-11 peptides have also been shown to form surface-active amyloid fibrils in fungi (Teertstra et al., (2009) *J Biol Chem* 284:9153-9159).

Aspects of the invention relate to functionalization of polymers, such as curli fibers, to create interfaces between organic fibers and inorganic materials, and to connect the synthesis of functionalized polymer subunits, such as curli subunits, to synthetic gene networks.

In some embodiments, csgBAC and/or csgDEFG is expressed in a cell on a plasmid under the control of an inducible promoter. It should be appreciated that a cell that expresses such plasmids may also express endogenous copies of csgBAC and/or csgDEFG. In some embodiments, the endogenous copies of csgBAC and/or csgDEFG are mutated or deleted. A variety of inducible promoters can be compatible with expression of csgBAC and/or csgDEFG. In certain non-limiting embodiments, inducible synthetic promoters such as pLtetO, which is induced by anhydrotetracycline (aTc), or pLlacO, which is induced by isopropyl β-D-1-thiogalactopyranoside (IPTG) (Lutz et al., (1997) *Nucleic Acids Res* 25:1203) is used. In certain embodiments, inducible synthetic promoters are regulated using non-transcription based regulators of gene expression. In certain embodiments, the non-transcription based regulators of gene expression are riboregulators, such as LacI riboregulators, TetR riboregulators or LuxR riboregulators.

Cells described herein can endogenously express wild type polymers, such as amyloid fibers, and can also be engineered to express modified polymers, such as amyloid fibers. As described herein, a modified polymer expressed by a cell refers to a polymer that is different from a wild type polymer. In some embodiments, a modified polymer has at least one nucleotide difference in its nucleic acid sequence than a wild type polymer. In some embodiments, a modified polymer has at least one amino acid difference in its protein sequence than a wild type polymer. In other embodiments, a modified polymer does not have any amino acid differences from a wild typepolymer. In some embodiments, a modified polymer has a different three-dimensional structure than a wild typepolymer.

Figure 1:
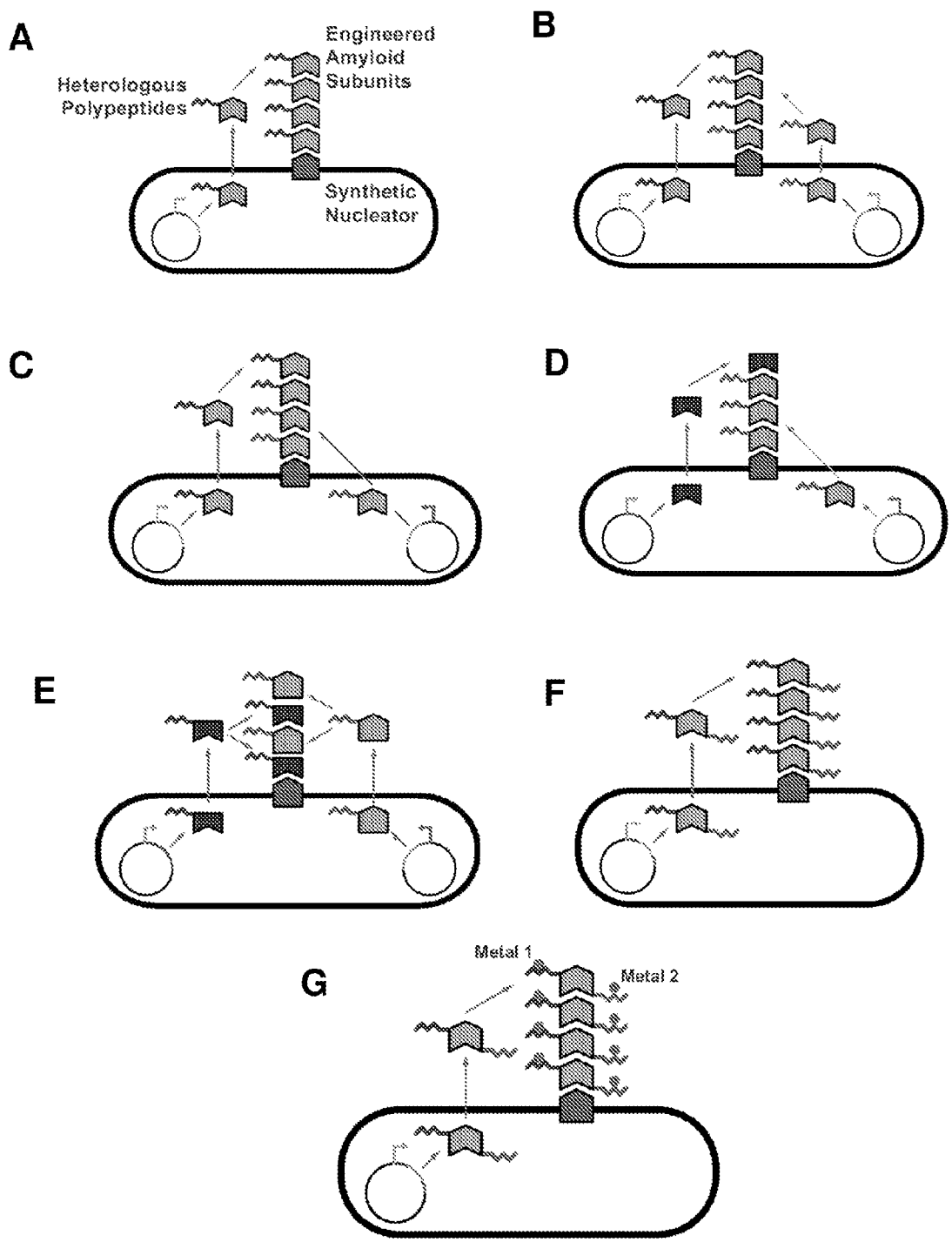
FIG. 1 provides several schematics depicting *E. coli* amyloid production.
Figure 2:
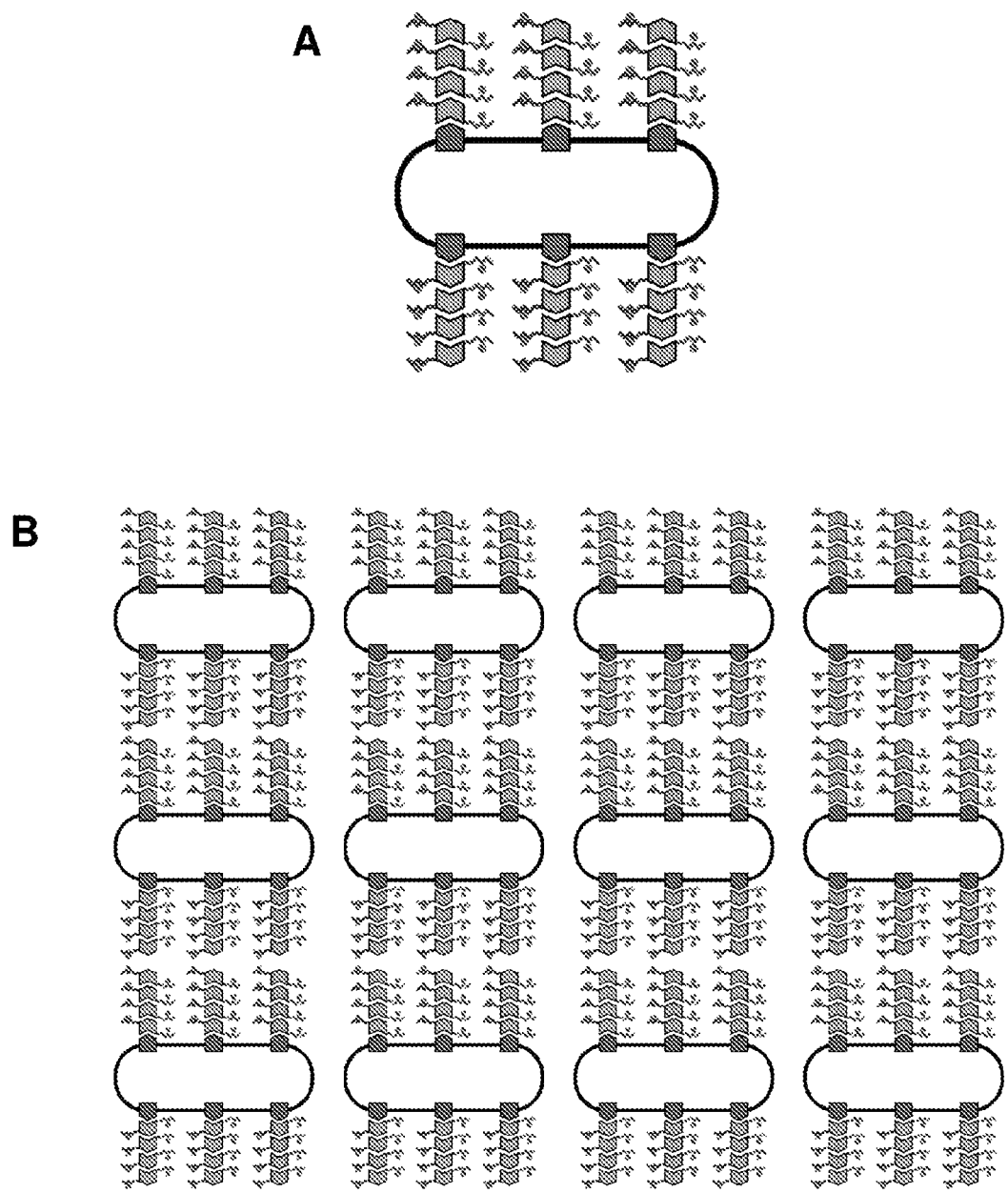
FIG. 2 presents schematics depicting nanostructures.
Figure 3:
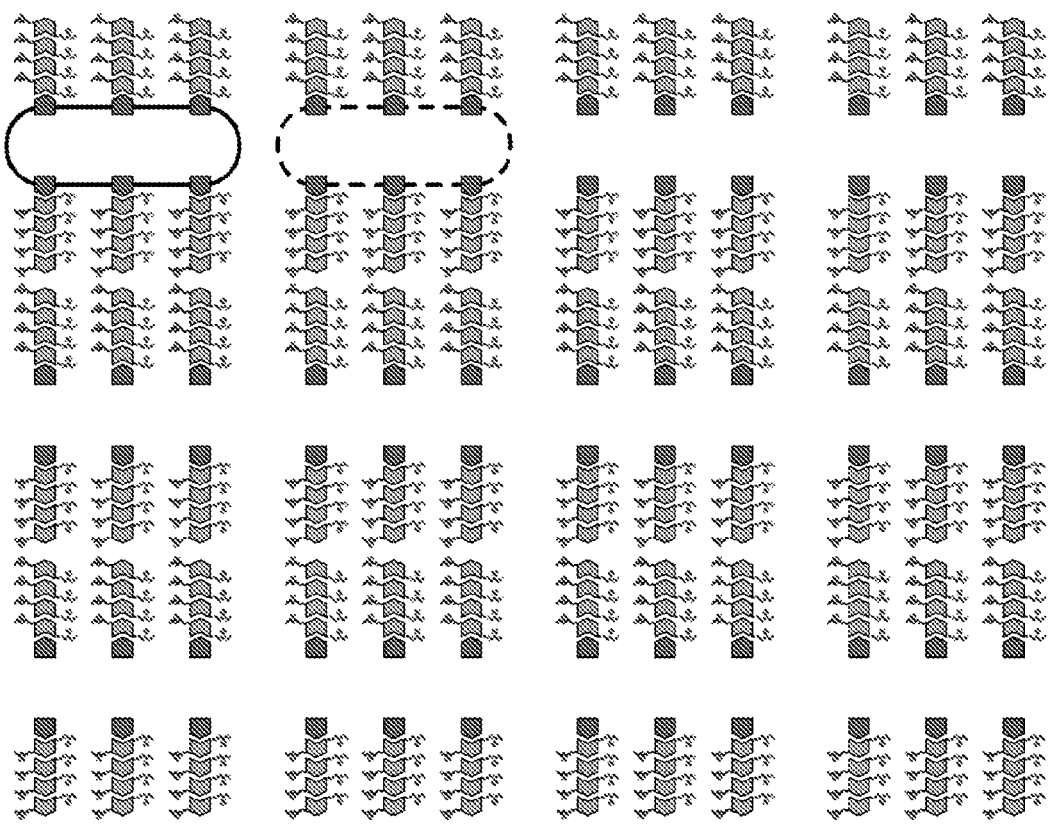
FIG. 3 presents a schematic showing that when the engineered cells are destroyed, the amyloid fibers and complex materials patterns are left behind. Amyloid fibers can survive the harsh treatments applied to destroy the cells due to their inherently stable nature.
Figure 17:
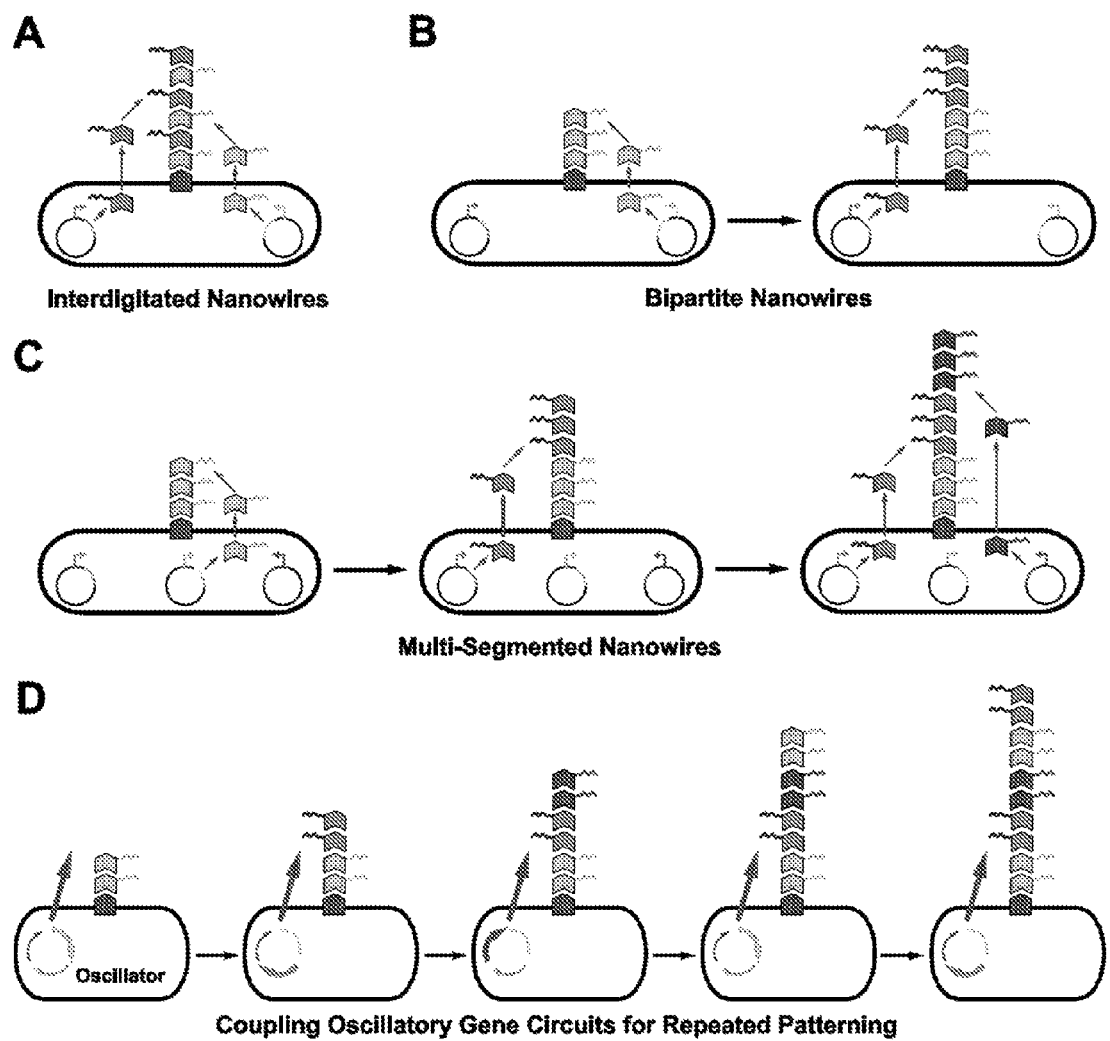
FIG. 17 depicts detailed nanoscale patterning of bacterial nanowires by the temporal expression of amyloid fiber subunits, CsgA, with synthetic promoters and gene circuits.

Modified polymers, such as amyloid fibers, can be genetically engineered to contain heterologous polypeptide domains. As used herein, a heterologous polypeptide domain within a polymer, such as an amyloid fiber, refers to a polypeptide domain within a polymer, such as an amyloid fiber, that is not normally expressed in the wild type polymer, such as an amyloid fiber. A heterologous polypeptide domain can be added at the N-terminus, C-terminus and/or internally within a polymer, such as an amyloid fiber. A polymer, such as an amyloid fiber, can contain one or more heterologous polypeptide domains, which can be the same or different. In some embodiments, a polymer, such as an amyloid fiber, contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more than 50 heterologous polypeptide domains. In some embodiments, the one or more heterologous polypeptide domains within a polymer, such as an amyloid fiber, are the same, while in other embodiments the one or more heterologous polypeptide domains within a polymer, such as an amyloid fiber, are different. For example, FIG. 1B shows that simultaneous expression of different amyloid subunits can create modified amyloid fibers that have interdigitated, interspersed, and different functional polypeptide domains. FIG. 1F shows that heterologous polypeptide domains can be attached N-terminal, C-terminal or internal to the amyloid subunits. Heterologous polypeptide domains can also be attached to internal sites in the amyloid subunits. FIG. 17 depicts multiple examples of nanoscale patterning of bacterial nanowires through expression of amyloid fibers with heterologous polypeptide domains.

In some embodiments, the genetic sequence of a polymer, such as an amyloid fiber, can be modified such that it contains nucleic acid sequences encoding for one or more heterologous polypeptide domains. In some embodiments, one or more affinity domains is introduced into the polymer, such as an amyloid fiber. For example, one or more SRC Homology 3 Domains (SH3 domains) and/or leucine zipper domains can be introduced into the polymer, such as an amyloid fiber.

In other embodiments, a polypeptide is expressed in the cell independently from the polymer, such as an amyloid fiber, is secreted from the cell, and then interacts with the polymer, such as an amyloid fiber, on the cell surface. In some embodiments, the polypeptide contains one or more affinity domains. For example, the polypeptide can contain one or more SRC Homology 3 Domains (SH3 domains) and/or leucine zipper domains.

A polymer, such as an amyloid fiber, can be functionalized through the expression of one or more heterologous polypeptide domains. As used herein, functionalization means that the introduction of one or more heterologous polypeptide domains into a polymer, such as an amyloid fiber, can confer one or more new properties on the polymer, such as an amyloid fiber and/or can modify an existing property of the polymer, such as an amyloid fiber. For example, the introduction of a heterologous polypeptide domain into a polymer, such as an amyloid fiber, can confer on the polymer, such as an amyloid fiber, a new or strengthened binding affinity.

In some embodiments, the new or strengthened binding affinity conferred on the polymer, such as an amyloid fiber, by the heterologous polypeptide domain is an affinity for inorganic nanomaterials. As used herein, a nanomaterial refers to a material that has structured components with at least one dimension less than 100 nm. As used herein, an inorganic nanomaterial refers to a nanomaterial that relates to compounds not containing hydrocarbon groups. In some embodiments, a wild type polymer, such as an amyloid fiber, without heterologous polypeptide domains, is also able to bind to an inorganic nanomaterial.

An inorganic nanomaterial can comprise a metal or metal nanoparticle. Several non-limiting examples of metals include alkali metals such as lithium, sodium, potassium, rubidium, caesium and francium, alkaline earth metals such as beryllium, magnesium, calcium, strontium, barium and radium, transition metals such as zinc, molybdenum, cadmium, scandium, titanium, vanadium, chromium, manganese, iron, cobalt, nickel, copper, yttrium, zirconium, niobium, technetium, ruthenium, rhodium, palladium, silver, hafnium, tantalum, tungsten, rhenium, osmium, iridium, platinum, gold, mercury, rutherfordium, dubnium, seaborgium, bohrium, hassium, meitnerium, darmstadtium, roentgenium and copernicium, post-transition metals such as aluminium, gallium, indium, tin, thallium, lead, bismuth, ununtrium, ununquadium, ununpentium and ununhexium, lanthanoids such as lanthanum, cerium, praseodymium, neodymium, promethium, samarium, europium, gadolinium, terbium, dysprosium, holmium, erbium, thulium, ytterbium and lutetium, and actinoids such as actinium, thorium, protactinium, uranium, neptunium, plutonium, americium, curium, berkelium, californium, einsteinium, fermium, mendelevium, nobelium and lawrencium.

It should be appreciated that any metal or metal nanoparticle can be compatible with aspects of the invention. In some embodiments, the metal or metal nanoparticle is a gold nanoparticle, a silver nanoparticles, zinc sulfate, cadmium sulfate, iron oxide, cobalt oxide, cobalt platinum, iron platinum or a quantum dot.

In some embodiments, the inorganic nanomaterial is a semiconductor. In certain embodiments, the semiconductor is zinc sulfide or cadmium sulfide.

In other embodiments, the new or strengthened binding affinity conferred on the polymer, such as an amyloid fiber, by the heterologous polypeptide domain is an affinity for other polymers, such as amyloid fibers, or protein structures.

Aspects of the invention involve introduction of heterologous polypeptide domains into polymers, such as amyloid fibers, including as curli fibers. As discussed in Example 1, and shown in FIG. 7, nucleator regions within CsgB were identified using peptide arrays. Structure prediction algorithms were also used to determine which sequences within CsgA interact with the CsgB nucleators. CsgA can form curli fibers even when regions of the protein are deleted and even when a foreign peptide is attached to the protein (FIG. 10C), indicating that this protein is amenable to engineering. As shown in Example 5, standard experimentation can be used to test various insertion sites within the CsgA protein for the introduction of heterologous peptide domains without disrupting curli fiber formation.

Thus, non-limiting embodiments of the invention relate to the introduction of heterologous polypeptide domains into the CsgA and/or the CsgB protein. In some embodiments, one or more heterologous polypeptide domains is introduced at the N-terminus, the C-terminus and/or internal to the CsgA protein and/or the CsgB protein. In some embodiments, heterologous polypeptide domains are added to CsgA, such as within or between one or more of the repeat regions of the protein, to increase the fiber diameter. In other embodiments, one or more deletions within CsgA are created to shorten the fiber diameter. For example, in certain embodiments, deletion of repeat 3 (R3) or repeat 4 (R4) of CsgA results in shortened amyloid fibers (Wang et al., (2008) *J Biol Chem* 283:21530).

In some instances, it is desired that the polymers, such as amyloid fibers, including curli fibers, laterally associate to form a thick bundle or mat on the surface of the cell, rather than individual fibers. This bundle or mat formation is preferable in applications where dense materials are needed, such as in the formation of materials that are resistant to puncturing or projectiles, such as armor. Thus, in some embodiments, polymers, such as amyloid fibers, including curli fibers can be modified in such a way as to promote lateral association, such as through the introduction of one or more heterologous polypeptide domains that promote interaction with other polymers, such as amyloid fibers, including curli fibers.

In other instances, it is desired that lateral association between polymers, such as amyloid fibers, be reduced or minimized and distinct polymers, such as amyloid fibers, are preferred. For example, reduction in lateral association may be preferable for applications such as wiring of electrical devices together in electronic chips and organizing nanoparticles for drug delivery. In some embodiments, reduction in lateral association is achieved by expressing charged residues, such as glutamic acid, in the polymer, such as the amyloid fiber, to increase electrostatic repulsion between polymers, such as amyloid fibers including curli fibers. Charged residues can be inserted anywhere within the polymer, such as an amyloid fiber. In some embodiments, charged residues are inserted into the CsgA protein. In some embodiments, sonication of polymers, such as amyloid fibers, including curli fiber samples, is used to separate associated fibers into individual fibrils.

In some instances, straight or curved polymers, such as amyloid fibers, including curli fibers, are preferred. In some embodiments, short and straight polymers, such as amyloid fibers, including curli fibers, are achieved by overexpressing CsgB and by reducing or eliminating expression of CsgA, such that the curli fibers comprise polymers of CsgB. In other embodiments, thick (~10-15 nm) and curved fibers are achieved by expressing CsgB as a fusion, such as a fusion with maltose-binding protein (MBP) in the presence of reduced or eliminated endogenous expression of CsgB. In some embodiments, CsgA, CsgB and/or protein fusions containing one or both of these proteins are expressed under inducible control and their expression levels are optimized for the production of fibers with preferred thickness and curvature.

Some aspects of the invention relate to expression of polymers, such as amyloid fibers, including curli fibers, on the cell surface. In some embodiments, the expression of one or more polymers, such as amyloid fibers is localized to a specific region of the cell surface. For example, in certain embodiments, one or more polymers, such as amyloid fibers, is localized to one or both poles of the cell. In certain embodiments, amyloid fibers are localized to the poles through expression of a CsgB fusion protein, such as MBP-CsgB in the presence of reduced or absent endogenous CsgB expression. In some embodiments, localization of amyloid fibers to the cellular poles is achieved by fusion of a protein such as CsgA or CsgB with a cell-surface protein that exhibits polar localization. For example, in certain embodiments, CsgA or CsgB is fused to IcsA. In other embodiments, one or more polymers, such as amyloid fibers, is localized along the length of the cell, rather than at the poles.

Figure 12:
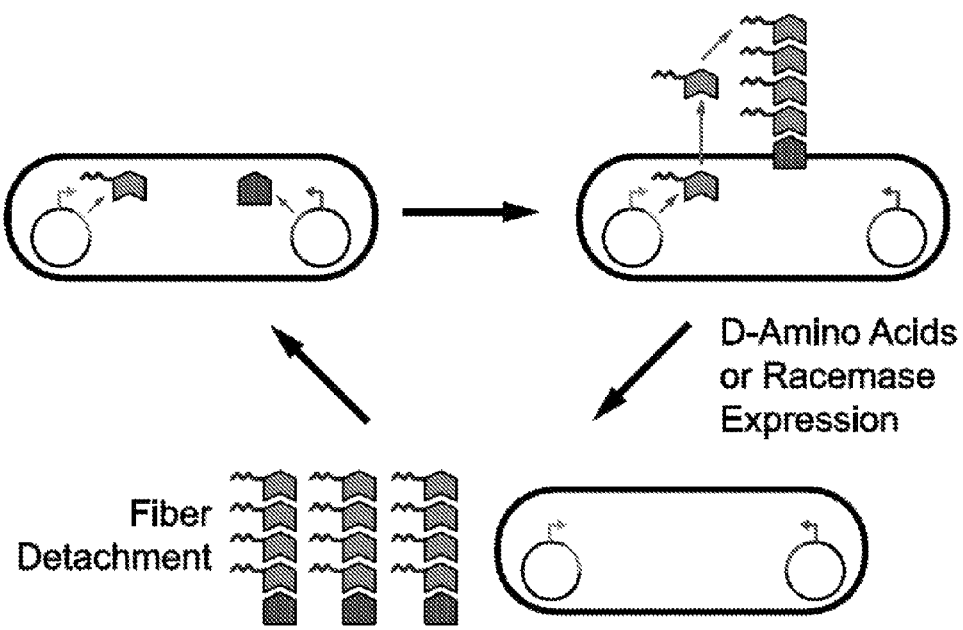
FIG. 12 shows that the proposed continuous curli fiber production cycle involves the controlled synthesis of CsgA subunits (shown in light grey) and CsgB nucleators (shown in dark grey), fiber nucleation and assembly, and the addition of D-amino acids or expression of racemases to detach fibers. This production cycle is meant to produce individual nanowires that can be incorporated into downstream applications where cellular attachment is not necessary.

Some aspects of the invention relate to the release of polymers, such as amyloid fibers, once they have assembled on the surface of a cell, allowing for their collection and purification. As shown in FIG. 12, in some embodiments, the addition of exogenous D-amino acids is used to trigger detachment of amyloid fibers. Any D-amino acid or combination of two or more D-amino acid can be compatible with aspects of the invention. For example, in certain embodiments, one or more of D-leucine, D-methionine, D-tyrosine, and D-tryptophan is used. In some embodiments, expression of a gene that encodes for an enzyme that converts L-amino acids to D-amino acids is overexpressed in the cell. For example, a racemase enzyme can be overexpressed in the cell. In certain embodiments, one or more of B. subtilis ylmE and racX and E. coli alr, dadX, mud, yhfX, and ygeA are overexpressed in the cell.

In some embodiments, continuous polymer production, such as fiber production, is achieved by incubating engineered cells in a device such as a microfluidic chip, inducing polymer production, such as fiber production, for example, by providing a chemical input, and adding exogenous D-amino acids to trigger release of the polymers, such as amyloid fibers.

In other embodiments, the polymer assembles inside the cell or outside the cell, rather than at the cell surface.

Aspects of the invention relate to engineering of nanowires that interface organic and inorganic materials. As used herein, a nanowire refers to a nanostructure with a diameter on the order of a nanometer. For example, polymers, such as curli amyloid fibers, are engineered to display peptides which can bind and nucleate inorganic nanomaterials, such as gold, quantum dots, and iron oxide. These peptides are inserted into surface-exposed regions of the polymers, such as curli fibers. In some embodiments, a recombinant polymer, such as a curli fiber, is expressed in the cell, wherein the recombinant polymer, such as a curli fiber sequence contains regions of DNA encoding for one or more heterologous peptides. When the polymer, such as a curli fiber is translated, the protein sequence contains the one or more heterologous peptide domains. By controlling the density and spacing of the peptides, and displaying the peptides at multiple locations along the polymer, such as curli amyloid structure, inter-peptide distances on the order of nanometers to sub-nanometers can be achieved.

In some embodiments, polymers, such as curli fibers, are modified to express antibodies or fragments thereof. For example, the polymer, such as a curli fiber, can be modified to express single antigen-binding domains, comprising small antigen-binding fragments of antibodies (e.g., based on $V_H$, $V_L$ or $V_{HH}$ fragments, or derivatives or fragments thereof), ranging from 11 kDa to 15 kDa, and which are collectively referred to herein as "single domain antibodies". The term "single domain antibodies" as used herein includes NANOBODIES® (Ablynx N.V., Ghent, Belgium), which include variable domains of heavy chain antibodies of camelid species, humanized variants thereof and heavy chain variable domains of other species in which "camelizing" alterations to amino acid sequence have been made. Another type of single domain antibodies are Domain Antibodies or "dAb's" (Domantis Inc., Waltham, Mass., USA).

Exemplary patents and applications describing various aspects of NANOBODIES® include: U.S. Pat. Nos. 5,759,808, 5,800,988, 5,840,526, 5,874,541, 6,005,079, 6,015,695, 6,765,087, and 6,838,254; US published patent applications 2003/0088074, 2004/0248201, 2004/0253638, 2005/0214857, 2005/0037358, 2005/0048060, 2005/0054001, 2005/0130266 and 2006/0034845; and PCT published applications WO 97/49805, WO 03/035694, WO 03/054016, WO 03/055527, WO 2004/062551, WO 2004/041867, WO 2004/041865, WO 2004/041863, WO 2004/041862, WO 2004/041867, and WO 2005/044858.

Exemplary patents and applications describing various aspects of Domain Antibodies include: US published patent applications 2004/0058400, 2004/0110941, 2004/0127688, 2004/0192897, 2004/0219643, 2006/0063921 and 2006/0002935; and PCT published patent applications WO 03/002609, WO 2004/003019, WO 2004/058821, WO 2004/058822, and WO 2005/118642).

In some embodiments, in order to further improve the avidity (i.e., for a desired antigen) of polypeptides that comprise single domain antibodies, and/or to provide constructs that can bind to two or more different antigens, two or more single domain fragments can be combined in a single polypeptide construct, resulting in a multivalent and/or multispecific polypeptide construct. The antibody domains can be coupled to each other directly (e.g., as a fusion protein) or using polypeptide or non-polypeptide linkers. Single domain antibodies (or multivalent and/or multispecific polypeptide constructs) can also be coupled to polypeptides other than antibodies. Single domain antibodies (or multivalent and/or multispecific polypeptide constructs) can also be coupled to a non-polypeptide group, such as a toxic agent or a tracer.

In some embodiments, a polymer subunit, such as a curlin subunit, including CsgA can be engineered to comprise one or more heterologous metal-binding peptides. In some embodiments, the metal-binding peptide is a gold-binding peptide (Au-BP), a zinc-binding peptide (ZnS-BP), a cadmium-binding peptide (CdS-BP), an iron oxide-binding peptide ($Fe_3O_4$-BP), an iron-platinum-binding peptide (FePt-BP) or a cobalt-platinum-binding peptide (CoPt). In certain embodiments, the sequence of the Au-BP comprises or consists of SEQ ID NO:1 (LKAHLPPSRLPS), the sequence of the ZnS-BP comprises or consists of SEQ ID NO:2 (CNNPMHQNC), the sequence of the CdS-BP comprises or consists of SEQ ID NO:3 (SLTPLTTSHLRS), the sequence of the $Fe_3O_4$-BP comprises or consists of SEQ ID NO:30 (CDSPHRHSC), the sequence of the FePt-BP comprises or consists of SEQ ID NO:38 (HNKHLPSTQPLA) and the sequence of the CoPt-BP comprises or consists of SEQ ID NO:45 (CNAGDHANC).

In some embodiments, one or more metal-binding peptides is introduced at the N-terminus, C-terminus or internal to the polymer subunit, such as the CsgA protein, optionally using a linker sequence such as GGGS. As discussed in Example 2, and as shown in FIG. 14A, gold particles were found to bind to CsgA-Au-BP fibers, indicating the effectiveness of the insertion of metal-binding peptides into this curli protein. Curli nanowires composed of CsgA-ZnS-BP were also found to nucleate zinc sulfate formation (FIG. 15) and CsgA-CdS-BP was also found to achieve CdS nucleation.

It should be appreciated that polymers, such as amyloid fibers, including curli fibers can be engineered to bind to and nucleate a variety of materials through the integration of heterologous peptides. In certain non-limiting embodiments, the material is iron oxide, silver nanoparticles, cobalt oxide, cobalt platinum or iron platinum. Routine experimentation can be used to optimize conditions for metal binding and nucleation. For example, temperature, pH and incubation time are non-limiting examples of parameters that can be varied to optimize metal binding and nucleation.

In some embodiments, non-specific binding of polymers, such as amyloid fibers, including curli fibers, to certain materials is reduced or eliminated by displaying peptides on the polymers, such as amyloid fibers, including curli fibers, that block non-specific binding. For example, tetra-glutamate peptides can be used to block non-specific binding of gold nanoparticles.

Further aspects of the invention relate to the production of conductive nanowires. In some embodiments, conductive nanowires are used to enhance electron transport in biofilms. Anode-respiring bacteria (ARBs) can be used to produce electrical current for microbial fuel cells by oxidizing organic substrates and transferring extracellular electrons to anodes (Tones et al., (2005) FEMS Microbiol Rev 34:3). Electrical conduction through biofilms enables distant bacteria to transfer electrons to anodes and limit potential losses. Id. Biofilm conduction in ARB monocultures is thought to be due to microbial nanowires synthesized by the ARBs themselves (Tones et al., (2005) FEMS Microbiol Rev 34:3; Reguera et al., (2005) Nature 435:1098; Gorby et al., (2006) Proc Natl Acad Sci USA 103:11358). A mixed biofilm, comprising cells that are engineered for enhanced production of conductive nanowires, can result in increased efficiency of nanowire production. In some embodiments, mixed biofilms are created that are composed of conductive bacteria plus cyanobacteria that exhibit light-dependent electrogenic activity, thereby attaining direct sunlight to electricity conversion (Pisciotta et al., (2010) PLoS One 5:e10821).

In some embodiments, conductive biofilms are created by engineering cells such as E. coli cells to express conductive polymers such as curli nanowires. Cells can be engineered to express metal-binding peptides on the surface of polymers such as curli to nucleate conductive materials and/or to display conductive cytochromes on the surface of polymers such as curli. For example, in some embodiments, gold-binding and silver-binding peptides are expressed in high density along polymers such as curli fibers (Scheibel et al., (2003) Proc Natl Acad Sci USA 100:4527). In other embodiments, bacterial cytochromes (such as cytochrome $b_{562}$) are fused to surface-exposed locations in polymer subunits such as CsgA (Baldwin et al., (2006) J Am Chem Soc 128:2162). In some embodiments, multiple cytochrome units are fused within the polymer subunit, such as CsgA subunit, at sites that can accept foreign inserts. In certain embodiments, one or more cytochrome units are fused to the N-terminus and/or the C-terminus of the polymer subunit, such as the CsgA subunit. In certain embodiments, one or more cytochrome units are inserted internally within the polymer sequence, such as the CsgA sequence, such as between the N22 and the R1 repeat regions in CsgA. In certain embodiments, deletions are made in CsgA that still preserve curli formation, in order to decrease total complex size and improve secretion.

Figure 16:
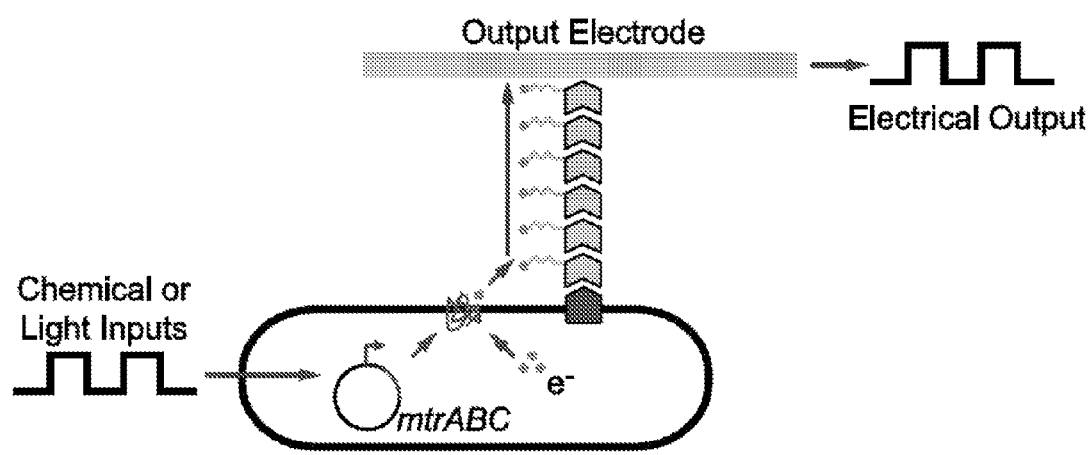
FIG. 16 shows that chemical or light inputs into engineered cells control the expression of electron exporting systems, thus driving electrical signaling through long-range conductive nanowires to output electrodes.

Aspects of the invention relate to the use of conductive nanowires in electronic signaling pathways. Conductive nanowires described herein can be used to transmit electrical signals to non-living devices. Expression of the mtrCAB cluster from Shewanella oneidensis MR-1 in E. coli has been shown to enable the transport of intracellular electrons to the extracellular space (Jensen et al., (2010) Proc Natl Acad Sci USA 107:19213). Thus, in some embodiments, the mtrCAB system is integrated into E. coli that display conductive nanowires to enable long-range electrical signaling (FIG. 16). By modulating mtrCAB expression with inducible synthetic promoters, time-varying chemical inputs are converted into long-range electrical outputs that can be detected by external electrodes and electronics. In some embodiments, electrical outputs are designed that can be modulated on shorter time scales using synthetic gene circuits which are triggered by light, heat, magnetism, electrical fields, or changes in protein phosphorylation. In some embodiments, biological nanostructures sense and respond to light, heat, electrical fields and/or magnetic fields.

Aspects of the invention relate to programming of synthetic gene circuits for nanoscale, patterning. Polymers, such as curli fibers can be constructed in a variety of nanopatterns. FIG. 17 presents several non-limiting examples of nanopatterns. FIG. 17A shows an example of interdigitated patterning, wherein different curli subunits are expressed simultaneously from different inducible promoters. FIG. 17B shows an example of bipartite patterning, whereby different curli subunits are expressed under the control of inducible promoters activated sequentially or to two outputs of a genetic toggle switch. FIG. 17C provides an example of a multi-segmented design, whereby bipartite patterning is extended to more than two inducible promoters that are sequentially activated. FIG. 17D provides an example of a repeating pattern whereby the production of different curli subunits is coupled to genetic oscillators.

Further aspects of the invention relate to programming of synthetic gene circuits for microscale and macroscale patterning. As used herein, nanopatterning or nanoscale patterning refers to spatial control in the 1-1000 nm range, micropatterning or microscale patterning refers to spatial control in the 1-1000 μm range and macropatterning or macroscale patterning refers to spatial control in the >1 mm range. It should be appreciated that nanopatterning, micropatterning and macropatterning are not mutually exclusive, but rather, can be used simultaneously to produce materials that have structures on multiple scales. FIG. 39 presents non-limiting examples of spatial patterning techniques based on the creation of standing waves. FIG. 40 presents data demonstrating pattern formation.

Figure 18:
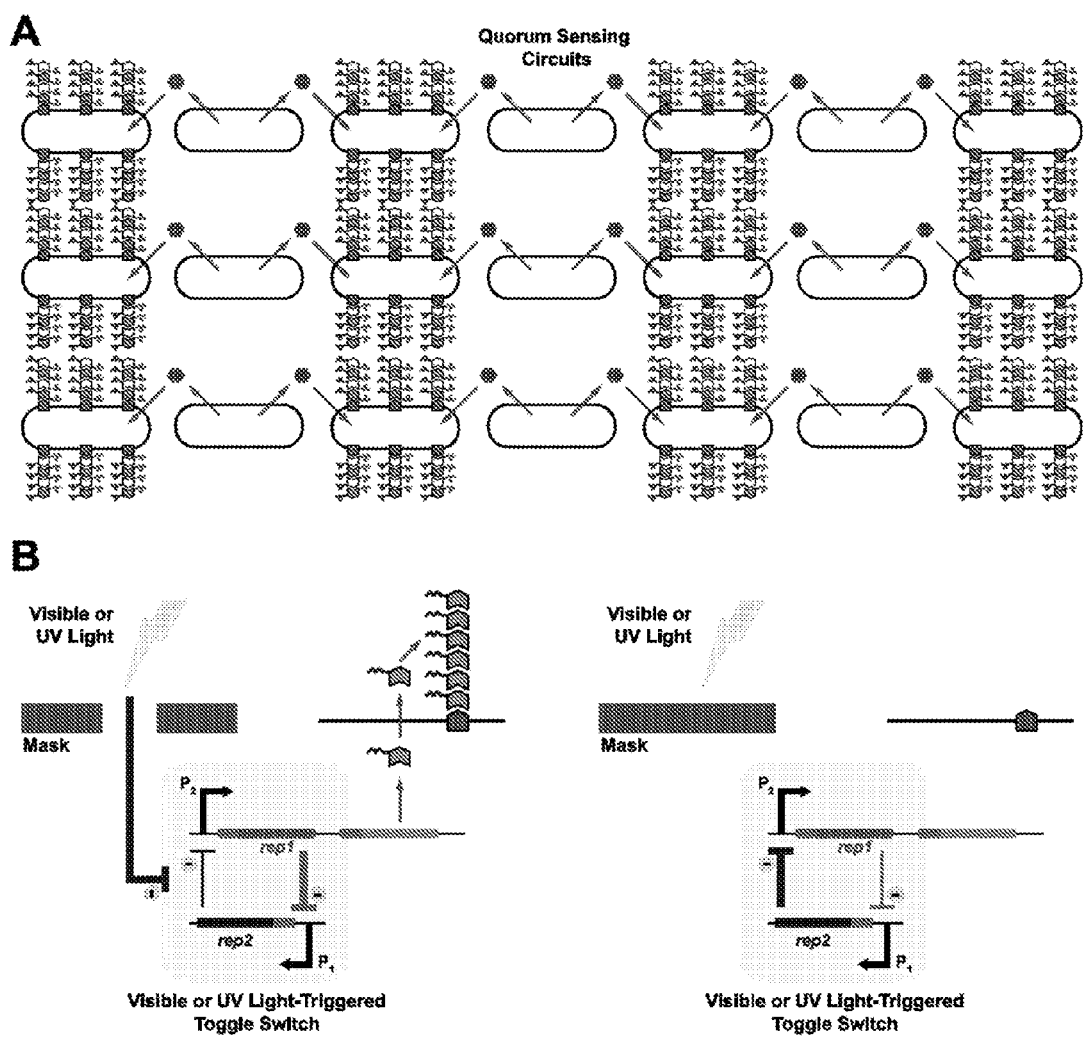
FIG. 18 shows that coupling the activation of curli-expressing circuits to synthetic gene circuits enables microscale and macroscale patterning.

Polymer-expressing circuits, such as curli-expressing circuits, can be connected to a quorum-sensing circuit. As used herein, a gene circuit refers to a collection of recombinant genetic components that responds to one or more inputs and performs a specific function, such as the regulation of the expression of one or more genes. A quorum-sensing circuit refers to a gene circuit that responds to a quorum sensing molecule as an input. As used herein, quorum sensing refers to the use of population density to coordinate certain cellular behaviors. A quorum sensing molecule refers to a molecule produced by a cell that can signal population density of the population of cells containing that cell. In some embodiments, a quorum sensing molecule is an oligopeptide, an N-Acyl homoserine lactone (AHL), an autoinducer or a pheromone. Quorum-sensing circuits allow engineering of self-organizing bacteria. Previous work, using fluorescent proteins, has shown that bacteria can self-organize into specific patterns in a quorum-sensing system. Herein, the output of the quorum-sensing system is transcriptional regulation of curli fiber production. An example of a quorum sensing circuit is depicted in FIG. 18A.

Polymer-expressing circuits, such as curli-expressing circuits, can also be connected to a light-sensing circuit. As used herein, a light-sensing circuit refers to a gene circuit that responds to light as an input. As shown in FIG. 18B, UV-inducible toggle switches, visible-light-inducible promoters, and optical masks can be used to control the expression of curli and to define different areas of curli production. In some embodiments, visible-light-inducible promoters are connected to toggle switches or recombinase-based switches. In certain embodiments, a Single Invertase Memory Module (SIMM) is used. As used herein, a Single Invertase Memory Module refers to a heritable, stable, and interoperable memory device comprising a recombinase that can invert DNA between two oppositely-oriented cognate recognition sites.

Polymer-expressing circuits, such as curli-expressing circuits, can also be magnetic-field sensing circuits. In some embodiments, the magnetic-field sensing circuit incorporates cryptochromes, as described further in, and incorporated by reference from Maeda et al. (2012) *Proc Natl Acad Sci USA* 109:4774.

Polymer-expressing circuits, such as curli-expressing circuits, can also be heat-sensing circuits. In some embodiments, the heat-sensing circuit is a heat-sensitive toggle switch as described further in, and incorporated by reference from, Gardner et al. (2000) *Nature* 403:339.

Polymer-expressing circuits, such as curli-expressing circuits, can also be electrical field-sensing circuits. In some embodiments, the electrical field-sensing circuit incorporates a voltage-sensitive ion channel, as described further in, and incorporated by reference from, Catterall (1988) *Science* 242:50.

Some aspects if the invention relate to systems containing more than one different cell type. As used herein different cell types refer to cells that have different polymer production capacity and/or regulation. In some embodiments, two or more different cell types are used for polymer production, a non-limiting example of which is described in Example 9.

Modified polymer fibers, such as amyloid fibers, described herein have widespread applications. A platform is established for engineering novel biomaterials that can be integrated with inorganic materials and can be patterned at length scales spanning many orders of magnitudes. This platform can enable many future applications such as self-healing biomaterials, magneto-responsive bacteria, drug delivery (e.g., nanoparticles with one domain for targeting and another domain for carrying payloads), high-performance computation (e.g., nanowires composed of multiple types of materials), and energy storage (e.g., capacitors and batteries built by organizing conductive and non-conductive nanowires (Long et al., (2004) *Chem Rev* 104:4463).

By designing engineered cells, such as bacterial cells, to synthesize and deliver fresh subunits to damaged sites, healable biomaterials can be developed. Since polymers, such as amyloid fibers, are capable of self-polymerization, damaged fibers can be reassembled with the addition of new subunits. This property is useful for the design of materials that can be repaired by engineered cells such as bacterial cells. These materials enable the healing of conductive nanowires in microbial fuel cells or provide scaffolding for the repair of non-living materials such as armor. Moreover, the successful design of a healable bacterial biomaterial would provide insights into analogous biological systems, such as wound healing.

By designing polymers, such as curli nanowires, that can nucleate and bind to magnetic materials such as paramagnetic iron oxide, cells, such as bacterial cells, can be designed that can sense and respond to magnetic fields. By localizing these nanowires to the poles, magnetic nanowires can be used as a rudder to orient cells swimming along with magnetic fields. This system can be used to design autonomously navigating cells, such as bacterial cells or bacterial biosensors that can detect cracks or distortions in ship hulls. The synthetic system is expected to be more engineerable and controllable compared with natural magnetotactic bacteria for which molecular techniques are underdeveloped (Faivre et al., (2008) *Chem Rev* 108:4875). FIGS. 41 and 42 demonstrate surface-attached materials with affinity tags that can be used to bind paramagnetic nanoparticles, allowing cells to interface with magnetic fields.

Further applications of systems described herein include the creation of batteries with multiple materials and the creation of complex solar panels. Nanomaterials described herein can also be used to develop high performance nanostructures for the electronics industry, for example, high-performance interconnects or new devices for performing logic.

Further applications of the cells described herein include cell-surface display systems. For example, similar to phage display, polymers, such as curli or other amyloid fibers can be used to display a range of peptides on the surface of a cell, outside a cell or inside a cell. Peptides displayed on the polymers, such as on amyloid fibers, can be modified by modifying their underlying genetic sequences. In some embodiments, the genetic sequence is modified through random mutagenesis. In some embodiments, the genetic sequence is modified through directed mutagenesis such as high-throughput rational engineering via synthetic biology.

As one of ordinary skill in the art would be aware, homologous genes to the genes described herein can be obtained from other species and can be identified by homology searches, for example through a protein BLAST search, available at the National Center for Biotechnology Information (NCBI) internet site (ncbi.nlm.nih.gov). Genes associated with the invention can be cloned, for example by PCR amplification and/or restriction digestion, from DNA from any source of DNA which contains the given gene. In some embodiments, a gene associated with the invention is synthetic. Any means of obtaining a gene encoding a protein associated with the invention is compatible with the instant invention.

Some aspects of the invention include strategies to optimize expression of surface-displayed polymers, such as amyloid fibers in a cell. In some embodiments, optimized expression of surface-displayed polymers, such as amyloid fibers, in a cell refers to producing a higher amount of a surface-displayed polymer, such as an amyloid fiber, in a cell following pursuit of an optimization strategy than would be achieved in the absence of such a strategy. In other embodiments, optimized expression of polymers, such as surface-displayed amyloid fibers, in a cell refers to achieving improved regulation of expression of one or more polymers, such as surface-displayed amyloid fibers, in a cell, relative to regulation achieved in the absence of an optimization strategy. Optimization of production of a polymer, such as an amyloid fiber, can involve modifying a gene encoding for a protein involved in polymer production, such as amyloid production, before it is recombinantly expressed in a cell. In some embodiments, such a modification involves codon optimization for expression in a bacterial cell. Codon usages for a variety of organisms can be accessed in the Codon Usage Database (kazusa.or.jp/codon/). Codon optimization, including identification of optimal codons for a variety of organisms, and methods for achieving codon optimization, are familiar to one of ordinary skill in the art, and can be achieved using standard methods.

In some embodiments, modifying a gene encoding for a protein before it is recombinantly expressed in a cell involves making one or more mutations in the gene encoding for the protein before it is recombinantly expressed in a cell. For example, a mutation can involve a substitution or deletion of a single nucleotide or multiple nucleotides. In some embodiments, a mutation of one or more nucleotides in a gene encoding for an enzyme will result in a mutation in the protein, such as a substitution or deletion of one or more amino acids.

In some embodiments "rational design" is involved in constructing specific mutations in proteins. As used herein, "rational design" refers to incorporating knowledge of the protein, or related proteins, such as its three dimensional structure, its active site(s), its substrate(s) and/or the interaction between the protein and other proteins, into the design of the specific mutation. In some embodiments, random mutagenesis is used for constructing specific mutations in gene encoding for proteins. Mutations generated by rational design or random mutagenesis can be created and screened for increased production or regulation of amyloid fibers.

In some embodiments, it may be advantageous to use a cell that has been optimized for polymer production, such as amyloid production, such as a cell in which proteins that regulate components of polymers, such as amyloid fibers, are upregulated or overexpressed. Overexpression can be achieved using any standard method. Increased expression levels of one or more genes associated with the invention can be achieved through selection of appropriate promoters and ribosome binding sites. In some embodiments, this may include the selection of high-copy number plasmids, or low or medium-copy number plasmids. The step of transcription termination can also be targeted for regulation of gene expression, through the introduction or elimination of structures such as stem-loops.

The invention also relates to the expression of heterologous polypeptide domains in polymers, such as amyloid fibers. As used herein, the terms "protein" and "polypeptide" are used interchangeably and thus the term polypeptide may be used to refer to a full-length polypeptide and may also be used to refer to a fragment of a full-length polypeptide.

As used herein with respect to polymers, such as amyloid fibers, or fragments thereof, "isolated" means separated from its native environment and present in sufficient quantity to permit its identification or use. Isolated polymers, such as amyloid fibers, may be, but need not be, substantially pure. The term "substantially pure" means that the polymers, such as amyloid fibers, are essentially free of other substances with which they may be found in production, nature, or in vivo systems to an extent practical and appropriate for their intended use. Substantially pure polymers, such as amyloid fibers, may be obtained naturally or produced using methods described herein and may be purified with techniques well known in the art. Because a polymer, such as an amyloid fiber, may be admixed with other components in a preparation, the polymer, such as an amyloid fiber may comprise only a small percentage by weight of the preparation. The polymer, such as an amyloid fiber, is nonetheless isolated in that it has been separated from the substances with which it may be associated in living systems.

The invention encompasses any type of cell that expresses polymers, such as amyloid fibers, associated with the invention, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Preferably the yeast strain is a *S. cerevisiae* strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, a plant cell, an insect cell, a rodent cell or a mammalian cell, such as a human cell.

The invention also encompasses nucleic acids that encode for any of the polypeptides described herein, libraries that contain any of the nucleic acids and/or polypeptides described herein, and compositions that contain any of the nucleic acids and/or polypeptides described herein. It should be appreciated that libraries containing nucleic acids or proteins can be generated using methods known in the art. A library containing nucleic acids can contain fragments of genes and/or full-length genes and can contain wild-type sequences and mutated sequences. A library containing proteins can contain fragments of proteins and/or full length proteins and can contain wild-type sequences and mutated sequences. It should be appreciated that the invention encompasses codon-optimized forms of any of the nucleic acid and protein sequences described herein.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. For example, heterologous expression of genes associated with the invention, for production of modified surface-displayed amyloid fibers in *E. coli*, is demonstrated herein. Modified amyloid fibers can also be expressed in other bacterial cells, fungal cells (including yeast cells), plant cells, rodent cells, mammalian cells etc.

A nucleic acid molecule associated with the invention can be introduced into a cell or cells using methods and techniques that are standard in the art. For example, nucleic acid molecules can be introduced by standard protocols such as transformation including chemical transformation and electroporation, transduction, particle bombardment, etc.

Expressing the nucleic acid molecule may also be accomplished by integrating the nucleic acid molecule into the genome.

In some embodiments one or more genes associated with the invention is expressed recombinantly in a bacterial cell. Bacterial cells according to the invention can be cultured in media of any type (rich or minimal) and any composition. As would be understood by one of ordinary skill in the art, a variety of types of media can be compatible with aspects of the invention. The selected medium can be supplemented with various additional components. Some non-limiting examples of supplemental components include glucose, antibiotics, IPTG for gene induction, ATCC Trace Mineral Supplement, and glycolate. Similarly, other aspects of the medium, and growth conditions of the cells of the invention may be optimized through routine experimentation. For example, pH and temperature are non-limiting examples of factors which can be optimized. In some embodiments, factors such as choice of media, media supplements, and temperature can influence production levels of amyloid fibers. In some embodiments the concentration and amount of a supplemental component may be optimized. In some embodiments, how often the media is supplemented with one or more supplemental components, and the amount of time that the media is cultured before production of an amyloid fiber, is optimized.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, particularly for the teachings referenced herein.

EXAMPLES

Example 1

Exploring, Functionalizing, and Controlling Bacterial Nanowires

Introduction

Synthetic *E. coli* are engineered herein to act as bacterial micro-robots (BMRs) that synthesize and organize amyloid biomaterials. There are many extracellular amyloid or amyloid-like fibers in various types of bacteria, including *Escherichia coli, Salmonella, Pseudomonas, Bacillus subtilis, Citrobacter, Shigella*, and *Enterobacter* (Dueholm et al., (2010) *Mol Microbiol* 77:1009). Herein, curli fibers are engineered in *E. coli*. Curli fibers are surface-expressed functional amyloids that mediate biofilm formation and mammalian cell invasion by *E. coli* (Barnhart et al. (2006) *Annu Rev Microbiol* 60:131). Individual curli fibrils are ~3-4 nm in diameter, can grow to many microns in length and can laterally associate to form larger bundles (Shewmaker et al., (2009) *J Biol Chem* 284:25065).

This broad synthetic-biology-based platform can direct the organized assembly of organic and inorganic materials and establish useful interfaces between living cells and non-living devices. The platform utilizes bacterial micro-robots to produce bacterial nanowires for at least two distinct applications: 1) to synthesize biomaterials and inorganic materials with well-controlled and detailed nanoscale, microscale, and macroscale patterning; and 2) to interface living bacteria with inorganic materials and non-living devices via modalities such as electricity and magnetism.

Coupling the synthesis of amyloid subunits to synthetic gene circuits enables nanoscale patterning. Microscale patterning can be achieved by programming synthetic bacteria (with μm-level dimensions) to self-organize and produce nanostructures based on cellular position and state. Directed microscale and macroscale patterning can be performed by the optical triggering of biological circuits within cells. Finally, interfaces between bacterial nanowires and non-living materials can be established by functionalizing the nanowires with material-binding peptides or other active biomolecules.

Engineering synthetic bacteria to produce multifunctional and multipatterned nanowires using the curli amyloid system has several major advantages over previous technologies for creating biomaterials and/or nanomaterials (Dickerson et al., (2008) *Chem Rev* 108:4935):

1. Efficient assembly of amyloid nanostructures: Almost all of the studies to date that have used amyloid fibers for self-assembling nanostructures have heterologously expressed and purified amyloid subunits followed by long-term incubation (i.e., multiple days) for fibril assembly. However, the expression and purification of many amyloids can be difficult due to their propensity for aggregation. Long incubation times are due to the significant lag phase that can precede the assembly phase. In contrast, bacterial amyloid systems have evolved to express and export soluble subunits without intracellular aggregation followed by efficient nucleation and assembly into insoluble fibers on cell surfaces. Thus, functional amyloids in bacteria constitute a scalable platform for producing and engineering biological nanomaterials using BMRs.

2. Encoding multiple functional domains: By genetically engineering the structural subunits that polymerize into amyloid fibers to display functional peptides and proteins, biomaterial scaffolds with active properties can be created. As curli subunit proteins are quite robust to mutations, insertions, and deletions, multiple peptides and biomolecules can be engineered into single subunits, resulting in high density and multifunctionality.

3. Bidirectional interfaces between living and non-living devices: Since curli are naturally linked to cell surfaces, they can be used to create novel interfaces between living cells with non-living materials and devices via modalities such as electricity and magnetism.

4. Nanoscale anisotropic patterning: Bacterial curli amyloids are anchored in the outer membrane and thus, curli subunits are polymerized into fibers that extend away from the cell surface. This directional assembly allows for complex anisotropic patterning by linking the expression of different functionalized amyloid fiber subunits to synthetic gene circuits. The temporal expression of different curli subunits by these synthetic gene circuits can then be translated into unique spatial patterns in the curli fibers.

5. Nano-, micro-, and macro-level patterning of biomaterials: By connecting synthetic gene circuits which control curli fiber expression and assembly to quorum-sensing circuits or light-sensing circuits in bacteria, autonomous or user-defined control of nanowire production and patterning can be achieved at the nanoscale, microscale, and macroscale.

6. Designing nanostructures using synthetic biology and evolution: Curli fibers are attached to bacterial cell surfaces and are therefore linked with the underlying DNA that encodes their protein sequences. Thus, curli can be used as a cell-surface display system referred to herein as curli display. Similar to phage-display and other cell-display systems, curli amyloids and the peptides displayed on curli fibers can be modified using evolutionary methods and high-throughput rational engineering via synthetic biology.
7. Attractive mechanical properties: Amyloids are a strong, stable, and thus promising class of biomaterials. Amyloid fibrils can exhibit impressive strength (0.6±0.4 GPa), which is comparable to steel (0.6-1.8 GPa), mechanical stiffness (Young's modulus 3.3±0.4 GPa), which is comparable to silk (1-10 GPa) (Smith et al., (2006) *Proc Natl Acad Sci* 103:15806), and large aspect ratios due to nanometer-scale diameters and micrometer-scale lengths. The assembly of amyloid fibers is due to self-polymerization and is relatively simple compared with other biomaterials such as silk.
8. Self-repairing nanomaterials: By engineering cells to express fresh amyloid subunits that are incorporated into damaged fibrils, bacterial micro-robots (BMRs) can be developed that can repair nanomaterials after trauma. Amyloid fibrils are formed by the polymerization of protein subunits at fibril ends where soluble subunits are converted into insoluble forms. Exogenous damage to amyloids expose broken fibril ends that can be repaired by the addition of fresh subunits (Smith et al., (2006) *Proc Natl Acad Sci USA* 103:15806). Such materials would be useful for self-healing armor.

A platform is designed herein for engineering new nanomaterials with useful properties such as multifunctionality, self-organization, and the ability to heal. Furthermore, this work enables the close coupling of living organisms with non-living devices to create integrated systems that can sense, process, and translate environmental signals into novel output modalities. Bacterial nanowire systems described herein build upon a rich foundation of structural and molecular studies on functional bacterial amyloids and phage-based interfaces between organic and inorganic materials. These systems represent a significant advancement over previous designs as they enable the design of complex nanopatterns by coupling nanomaterial synthesis with synthetic gene circuits and the interfacing of living cells with other living or non-living devices. This platform may be useful in applications such as microbial fuel cells with enhanced efficiency, advanced energy storage devices, self-healing biomaterials, cells which can communicate with non-living devices via electrical signals, and cells that can sense and respond to magnetic fields for autonomous navigation or for detecting damage in ship hulls.

Curli

The specific bacterial nanostructures engineered herein are extracellular *E. coli* amyloids called curli. Amyloids are aggregates of proteins or peptides with cross-beta structure and fibrillar morphology that assemble via a rate-limiting nucleation step followed by fibril extension (Haass et al., (2007) *Nat Rev Mol Cell Biol* 8:101; Chiti et al., (2003) *Nature* 424:805). Amyloid fiber structure consists of β-strands which are perpendicular to the fiber axis and β-sheets which stack parallel to the fiber axis. Amyloids are highly stable and resistant to protease digestion and 1% sodium dodecyl sulfate (Barnhart et al., (2006) *Annu Rev Microbiol* 60:131). Amyloids also bind to Congo Red dye, causing a red shift, and to Thioflavin T, causing fluorescence (Barnhart et al., (2006) *Annu Rev Microbiol* 60:131).

Curli amyloid assembly by *E. coli* involves multiple components (FIG. 5). The curli operon includes two transcriptional units, csgBAC and csgDEFG. The csgBAC transcriptional unit is positively regulated by CsgD and negatively regulated by the CpxA/CpxR system and Rcs, both of which are responsive to membrane stress. Id. The csgDEFG transcriptional unit is subject to complex regulation. Positive regulators include the OmpR/EnvZ system, RpoS, Crl, MlrA, and IHF while negative regulators include the CpxA/CpxR system and the Rcs system. Id. In natural systems, curli is optimally expressed in conditions that include temperatures below 30° C., low osmolarity, nutrient limitation, stationary phase, and a microaerophilic environment. Id.

The major curlin subunit, CsgA, is secreted as a soluble protein that is efficiently polymerized into fibrils by CsgB, an outer-membrane-associated protein which is also known as the minor curlin subunit. Id. CsgA and CsgB share sequence homology and form a cross-β sheet complex with five repeating strand-loop-strand structures (FIG. 6). Both CsgA and CsgB can form amyloid fibrils on their own (Shewmaker et al., (2009) *J Biol Chem* 284:25065; Barnhart et al., (2006) *Annu Rev Microbiol* 60:131). In vivo, CsgA is the major constituent of curli although CsgB is also found in curli to a lesser degree (Bian et al., (1997) *EMBO J* 16:5827). The function of CsgC is not well understood— mutations in CsgC do not affect curli but do affect the ability of bacteria to autoagglutinate (Hammar et al., (1995) *Mol Microbiol* 18:661).

CsgD is a positive regulator of csgBAC expression but does not regulate its own expression. CsgE is a chaperone-like protein thought to be involved in the stability of CsgA and CsgB; mutations in CsgE can decrease CR binding and lead to the formation of circular curli fibers (Barnhart et al., (2006) *Annu Rev Microbiol* 60:131). Similarly, CsgF is a chaperone-like protein which is secreted to the cell surface and is involved in associating CsgB with the cell surface helping CsgB nucleate curli fiber formation (Nenninger et al., (2009) *Proc Natl Acad Sci USA* 106:900). CsgG is a lipoprotein which is located in the outer membrane, is spatially clustered around curli fibers, and participates in the secretion of CsgA, CsgB, and CsgF (Nenninger et al., (2009) *Proc Natl Acad Sci USA* 106:900; Epstein et al., (2009) *J Bacteriol* 191:608). CsgG interacts with the N22 domain of CsgA (FIG. 6A) to mediate secretion to the cell surface (Chapman et al., (2002) *Science* 295:851). CsgG exists as an outer-membrane complex with CsgE and CsgF.

Figure 7:
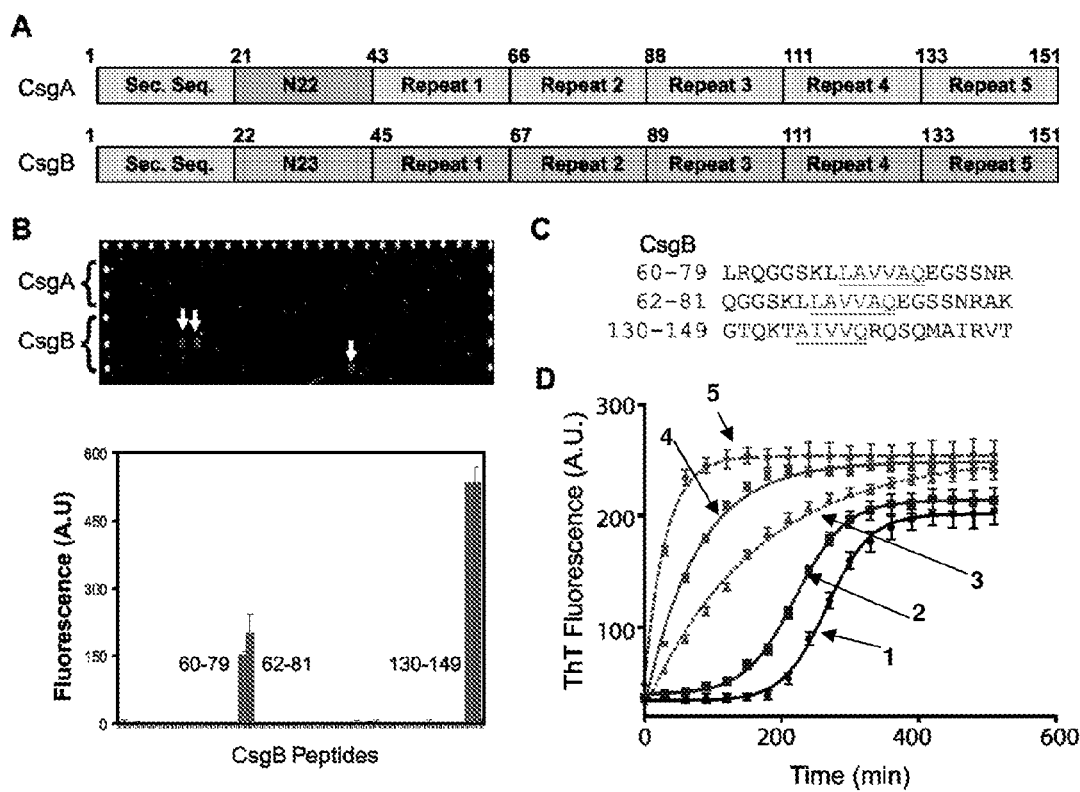
FIG. 7 shows the identification of curli amyloid nucleating sequences in CsgB.

Previously unknown interactions between CsgA and CsgB responsible for the efficient nucleation of CsgA into fibrils by CsgB have been elucidated. To pinpoint sequences that can nucleate curli assembly, 20-mer peptide arrays were created spanning the entire CsgA and CsgB protein sequences to which soluble fluorescently labeled CsgA was added (FIG. 7). The presence of amyloid assembly on the array was detected as increasing fluorescence over time (FIG. 7B). CsgB a.a. 130-149 showed the strongest signal, implicating this region as a strong nucleator. Two other CsgB regions, a.a. 60-79 and 62-81, had moderate fluorescence, indicating the presence of a weaker nucleator. These sites were validated as nucleators based on their ability to shorten and abrogate the lag time for in vitro CsgA amyloid assembly monitored by Thioflavin T (ThT) fluorescence (FIG. 7D). A structure prediction algorithm was also used to determine which sequences within CsgA (a.a. 43-50, 54-61, and 132-140) interact with the CsgB nucleators.

Expertise in synthetic biology and amyloid biology is applied herein to develop the curli system into a novel platform for multifunctional and multipatterned bacterial nanowires. There is substantial flexibility in CsgA, CsgB, and their interactions that is amenable to engineering with high-throughput and well-controlled synthetic biology tools. For example, CsgA can form curli fibers even with the deletion of entire repeats from its sequence (Wang et al., (2008) *J Biol Chem* 283:21530). The homolog of *E. coli* CsgA in *Salmonella* (AgfA) forms amyloid fibers when expressed from *E. coli* even though the amino-acid sequences of AgfA and CsgA are 74% identical (Barnhart et al., (2006) *Annu Rev Microbiol* 60:131; Collinson et al., (1999) *J Mol Biol* 290:741). Moreover, *Salmonella* AgfA is capable of accepting 16-residue peptide substitutions within its core structure while maintaining fiber formation (White et al., (2000) *J Mol Biol* 296:361). In addition, foreign peptides have been attached to CsgA without disrupting in vivo amyloid assembly (FIG. 10C).

Other Functionalized Biomaterials

Many of the systems designed for interfacing biological and non-biological materials have used filamentous-phage-displayed peptides which bind to inorganic materials. However, there are several major limitations with the phage-display approach.

The curli-based nanowire system described herein builds upon previous phage-based systems with several additional advantages (Lee et al., (2002) *Science* 296:892; Mao et al., (2004) *Science* 303:213; Nam et al., (2006) *Science* 312:885). For example, curli are polymerized by the addition of new subunits and therefore, curli properties such as diameter and length can be modulated by engineering the protein subunits. The curli-based system has the potential to enable complex and anisotropic nanopatterns by controlling directional assembly and curli subunit expression dynamics with synthetic gene circuits. Since curli are attached to bacterial cells, curli expression and operation can be linked to underlying synthetic gene circuits, thereby enabling continuous nanowire production cycles and complex patterning operations. Furthermore, as curli are amyloid fibers, they are resistant to harsh chemical conditions including high temperatures, changes in pH, and treatment with detergents, urea, and proteases (Barnhart et al., (2006) *Annu Rev Microbiol* 60:131; Chapman et al., (2002) *Science* 295:851).

Non-cell-associated in vitro amyloids have been functionalized for a variety of different purposes, including nanowire formation. For example, Scheibel et al. genetically modified the yeast NM prion to include an accessible cysteine residue that was then covalently linked to gold and silver particles (Scheibel et al., (2003) *Proc Natl Acad Sci USA* 100:4527). The resulting nanowires were about 80-200 nm in diameter and had conductive properties. Id. Baxa et al. attached enzymes such as barnase and carbonic anhydrase to yeast prion Ure2 amyloids and showed that enzymatic activity could be maintained (Baxa et al., (2002) *Proc Natl Acad Sci USA* 99:5253). Baldwin et al. successfully displayed cytochrome $b_{562}$ on amyloid fibrils and demonstrated that heme molecules could be efficiently incorporated (Baldwin et al., (2006) *J Am Chem Soc* 128:2162). Reches and Gazit used self-assembled peptides derived from amyloid fibrils to direct the formation of silver nanotubes (Reches et al., (2003) *Science* 300:625). These precedents prove that it is feasible to use amyloids to direct the formation of nanostructures. However, none of these studies have achieved anisotropic formation of complex nanopatterns, linked nanowires to cellular function, or leveraged bacterial microrobots as factories and organizers of nanomaterials. Described herein is the establishment of advanced functionality and interfaces between living and non-living cells.

Technical Approach

The technical approach described herein is built upon coupling self-assembling curli amyloid fibers, controlled by synthetic gene circuits, with non-living materials. New self-assembled and actively patterned materials that are organized at the nanoscale, microscale, and macroscale are created using bacteria engineered with the tools of synthetic biology. These bacteria are programmed to produce multifunctional nanostructures that can organize inorganic molecules such as metals, semiconductors, and magnetic materials. The utility of this approach is validated by making conductive nanowires and biofilms that can potentially enhance the efficiency of microbial fuel cells and enable electrical signaling between cells and electronic devices.

Figure 8:
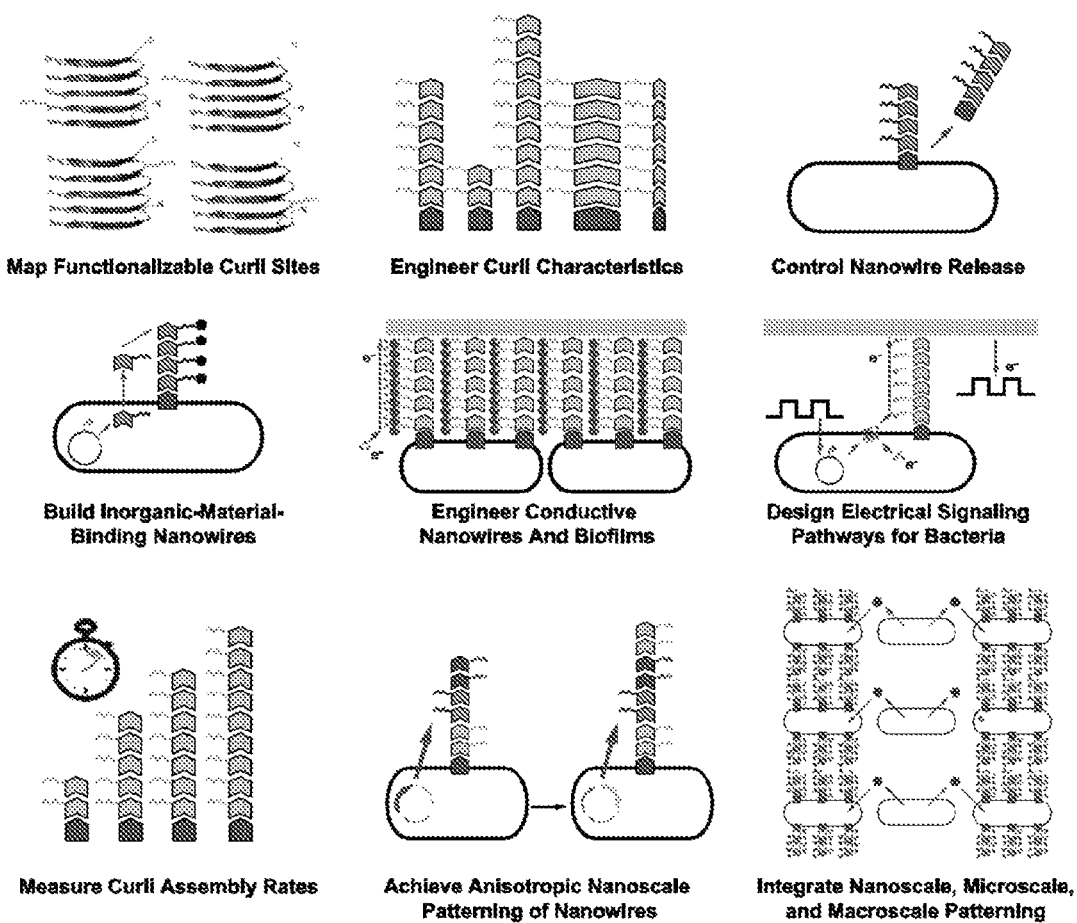
FIG. 8 depicts aspects of the technical approach described herein, involving developing a generalized platform for engineering bacterial nanowires with multifunctional and multipatterning capabilities. This platform has broad applicability to next-generation materials and interfacing living and non-living devices.

Multifunctional and multiscale nanomaterials are constructed by comprehensively probing and modulating the molecular characteristics of bacterial curli fibers, functionalizing curli subunits to create interfaces between organic fibers and inorganic materials, and connecting the synthesis of functionalized curli subunits to synthetic gene networks thereby producing complex patterns at the nanoscale, microscale, and macroscale (FIG. 8). This strategy relies on rapidly modifying the underlying DNA which encodes the structural curli proteins and controlling their expression using the tools of synthetic biology.

Since the two curli transcriptional units, csgBAC and csgDEFG, are normally under complex environmental regulation that may not be conducive to biomaterials applications, these genes are engineered to be expressed from inducible synthetic promoters such as pLtetO, which is induced by anhydrotetracycline (aTc), and pLlacO, which is induced by isopropyl β-D-1-thiogalactopyranoside (IPTG) (Lutz et al., (1997) *Nucleic Acids Res* 25:1203). These inducible systems are located on plasmids transformed into *E. coli* cells with the endogenous curli operons deleted. This enables the achievement of time-varying expression of curli components and the fine-tuning of curli production rates.

As discussed below, sites on curli fibers are mapped which can be functionalized while maintaining fiber formation and achieving control over the morphology, localization, and release of these nanowires. Preliminary studies have shown that foreign peptides can be attached to the C-terminus of CsgA subunits within curli nanowires by engineering the DNA encoding for the nanowires.

Bacterial nanowires are interfaced with inorganic materials and conductive fibers and biofilms are developed for potential applications in microbial fuel cells and electrical signaling. Curli fibers were created and validated that can bind and nucleate gold nanoparticles and ZnS materials. Synthetic gene circuits are then connected with nanowire synthesis to create nanoscale, microscale, and macroscale patterning that can be self-organizing or directed by external sources.

Mapping Candidate Sites in Curli Fibers for Functionalization

Figure 9:
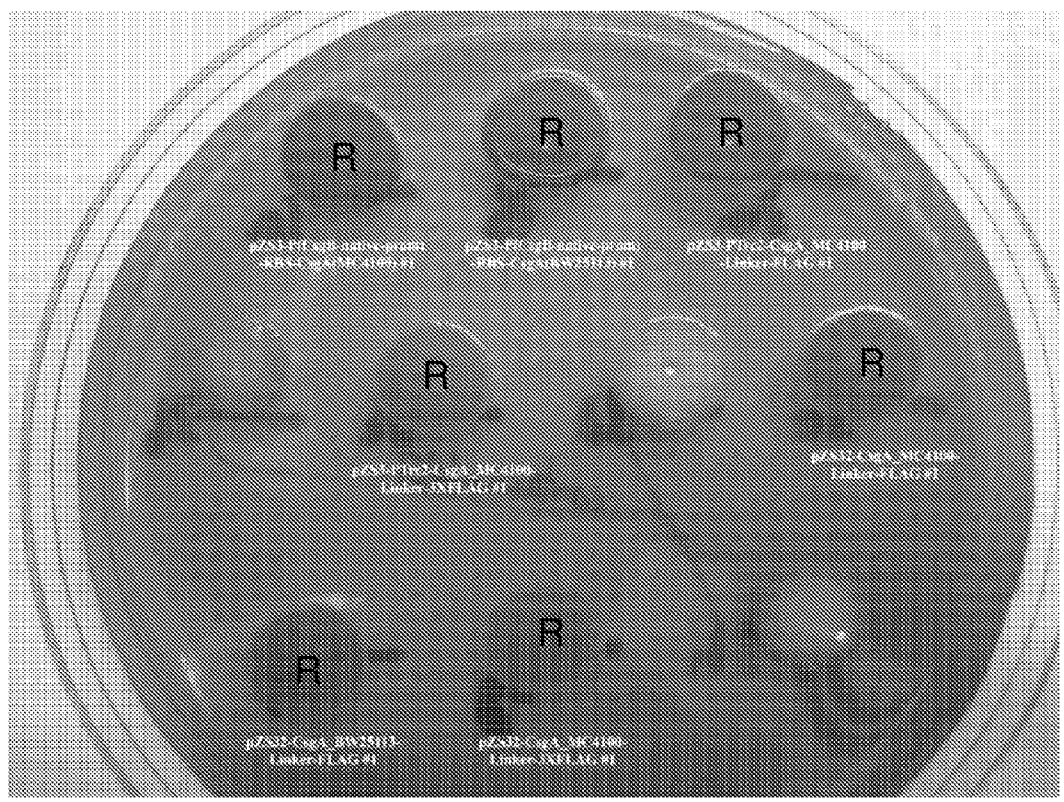
FIG. 9 depicts growth of engineered cells. Cells with CsgA expression plasmids were grown in YESCA media for 48 hours and spotted onto YESCA agar plates with Congo Red. Red color (depicted by the symbol "R") indicates expression of functional amyloid fibers which bind to Congo Red. These results show that CsgA-linker-FLAG allows the formation of functional amyloid fibers. These data also show that CsgA-linker-3×FLAG forms functional amyloid fibers, though these cells are not as red as cells with CsgA alone or CsgA-linker-FLAG. As a result, CsgA can be engineered to display heterologous polypeptides at the C-terminus and still form functional amyloid fibers.
Figure 10:
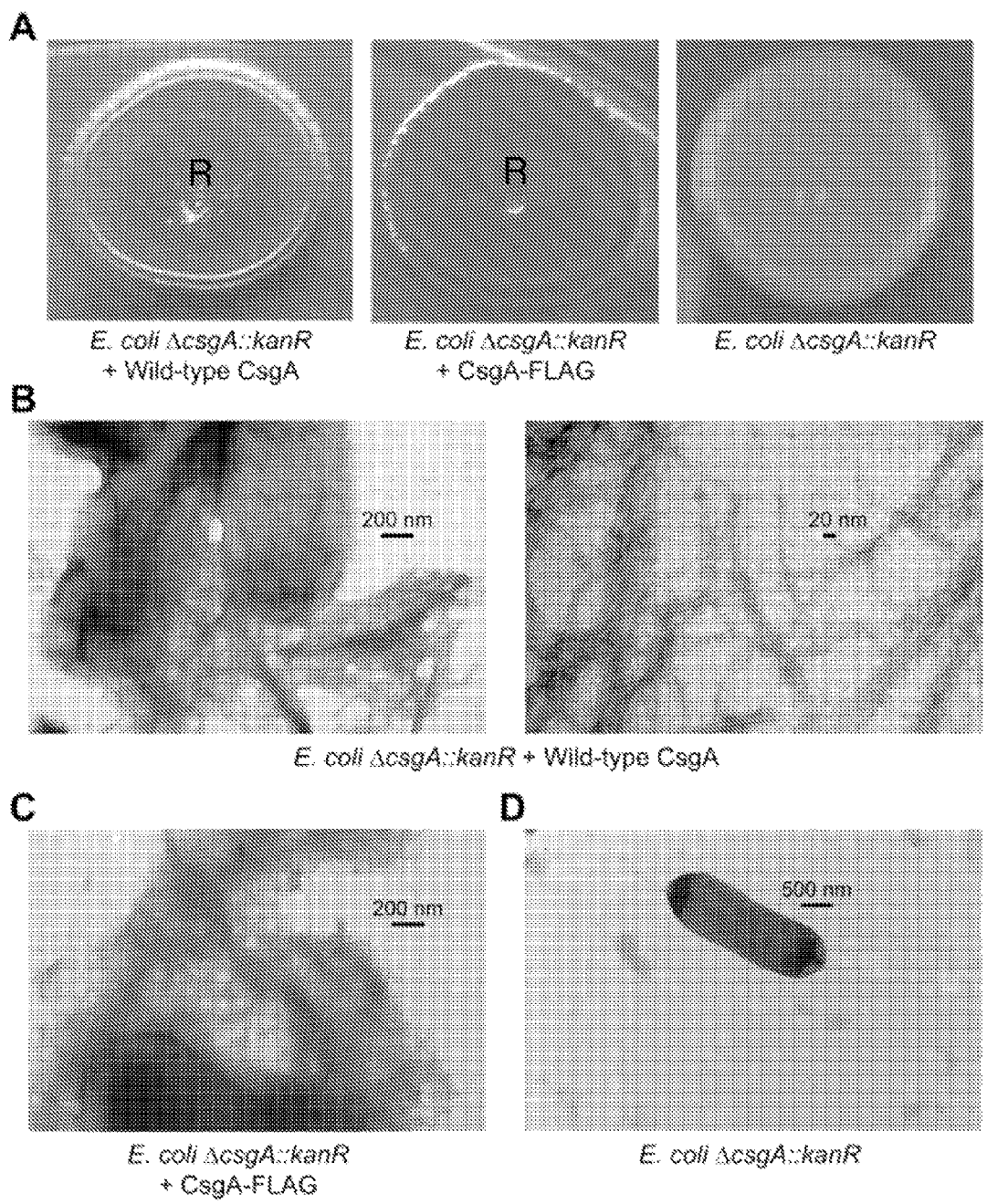
FIG. 10 shows that foreign peptides can be incorporated into curli amyloid fibers by attaching peptides to the C-terminus of the major curlin subunit, CsgA.

In order to interface curli amyloid fibers with living and/or non-living materials, the capability to encode material-binding peptides into the fibers is needed. These peptides should be accessible on fiber surfaces and not sequestered internally. Moreover, these peptides should not disrupt the ability of curli to form amyloid fibers. It is shown herein that short peptides, such as the FLAG tag, can be inserted at the C-terminal of CsgA without disrupting amyloid fiber formation and function (FIGS. 9-10).

To demonstrate that curli can accommodate heterologous polypeptide domains, FLAG and 3×FLAG epitopes were fused to the C terminus of the CsgA major curli subunit. FIG. 9 shows that the heterologous CsgA-FLAG and CsgA-3×FLAG constructs still constitute functional amyloid fibers based on Congo Red staining.

Two assays were used for fiber formation—Congo Red binding and transmission electron microscopy (TEM). Congo Red binding is assayed by spotting cells on YESCA agar with Congo Red (FIGS. 9, 10A) (Chapman et al., (2002) *Science* 295:851). If curli amyloid fibers are present, the resulting colonies are red (FIG. 10A). In addition, Congo Red binding can be quantified by incubating CR (15 µg/mL) with cells, centrifuging the cells at high speed (>13,000 rcf), and measuring the unbound CR in the supernatant using a spectrophotometer at 480 nm (Ishiguro et al., (1985) *J Bacteriol* 164:1233). Cells expressing high levels of curli will have decreased unbound CR and thus decreased absorbance at 480 nm.

FIG. 11 shows EM images of *E. coli* curli. The FLAG peptide was attached after the N22 sequence and before the R1 repeat sequence in the CsgA protein. It was demonstrated that curli fibers can still be formed (FIG. 11B). These data demonstrate that long nanowires can be formed (in the µm range) with small diameters (in the low nm range).

The CsgA protein was comprehensively mapped for regions that can tolerate the insertion and surface display of foreign peptides. To determine the locations which can display surface-exposed peptides, the 6×His or 7×His peptide tag was inserted along the entire CsgA sequence. The CsgA protein was mapped starting right after the Sec signal sequence all the way to the C-terminal (FIG. 7A and Table 1). Modified CsgA proteins were expressed in strains with the endogenous csgA gene removed, such as BW25113 ΔcsgA::kanR from the Keio collection (Baba et al., (2006) *Mol Syst Biol* 2:20060008. The His-tag is a preferred affinity tag since CsgA with C-terminal His tags have previously been expressed, purified, and shown to form fibrils (Shewmaker et al., (2009) *J Biol Chem* 284:25065).

It was verified that amyloid fibers are formed by plating cells on CR agar and measuring CR binding by intact cells using a microplate spectrophotometer (Ishiguro et al., (1985) J Bacteriol 164:1233). Fiber formation and surface-exposure of the affinity tag is confirmed visually using Transmission Electron Microscopy (TEM). Specifically, gold nanoparticles functionalized with nickel-nitrilotriacetic acid (AuNP-Ni-NTA) are used since Ni-NTA is known to bind to the His-tag with high affinity (Hainfeld et al., (1999) *J Struct Biol* 127:185). Whether the His-tag is located at the N-terminal, C-terminal, or internally, binding to Ni-NTA should occur as long as the His-tag is surface exposed. For samples where the His-tag is surface exposed, we expect to see a uniform coating of fibers with AuNP-Ni-NTA under TEM.

TABLE 1

A comprehensive matrix is created to map out amyloid fiber formation (assayed with CR and TEM) and surface-expression of the His-tag (assayed with Au—Ni-NTA nanoparticles) inserted at different positions within CsgA.

| After | 6xHis Inserted | | | | |
|---|---|---|---|---|---|
| Observations | $CsgA_{20}$ | $CsgA_{21}$ | $CsgA_{22}$ | ... | $CsgA_{151}$ |
| Color on CR Plates | | | | | |
| Quantitative CR Binding | | | | | |
| TEM Fibril Formation | | | | | |
| Binding to Au—Ni-NTA Particles | | | | | |

Engineering of Nanowire Dimensions, Morphology, and Localization

To form the basis of tunable biomaterials, control over curli fiber diameter, morphology, and localization is achieved. Nanowire dimensions and morphology are engineered by modifying the major curlin subunits, CsgA, and the minor curlin subunits, CsgB.

Dimensions

The question of whether long internal inserts in CsgA can increase the diameter of curli fibers is investigated. This is achieved by adding foreign peptides of different lengths at regions within CsgA that can accommodate inserts. The size of the peptides inserted into this region is progressively increased and it is observed whether curli formation is maintained and the diameter is affected. Since CsgA is thought to have a stacked configuration (FIG. 6), inserts can be added within each of the repeats to increase fiber diameter. Deletions within CsgA can also be inserted to shorten formed nanowires. For example, deleting repeat 3 or repeat 4 in CsgA (R3 and R4, respectively, in FIG. 6) results in shortened amyloid fibers (Wang et al., (2008) *J Biol Chem* 283:21530).

Morphology

Figure 4:
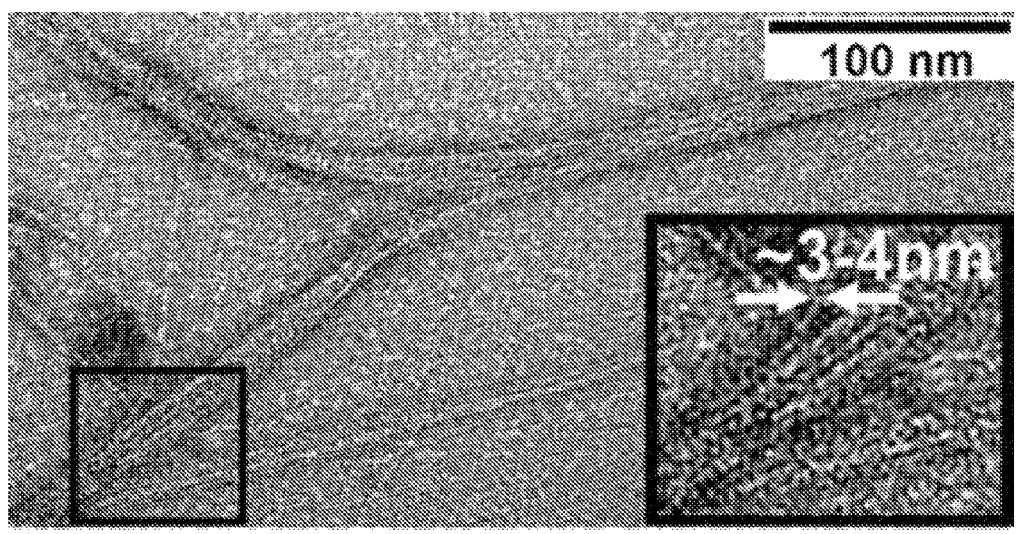
FIG. 4 shows curli amyloid fibers viewed under transmission electron microscopy (TEM). This image, from Shewmaker et al. (2009) *J. Biol Chem* 284:25065, shows the lateral association of individual curli fibrils to form larger bundles. Individual curli fibrils are about 3 to 4 nm in diameter.

As shown in FIG. 4, curli fibers are often laterally associated to form thicker bundles and mats instead of individual fibers (Shewmaker et al., (2009) *J Biol Chem* 284:25065). Curli mats can be useful in situations where achieving dense materials (e.g., for armor) is desired. However, distinct nanowires may be desirable in certain applications (e.g., wiring electrical devices together in electronic chips, organizing nanoparticles for drug delivery). Reduction of lateral association is achieved by expressing charged residues, such as glutamic acid, to increase electrostatic repulsion between curli fibers. These residues are inserted into CsgA locations mapped out as described above. In addition, curli fibers samples are sonicated to try to separate associated fibers into individual fibrils.

Instead of curli mats, in some instances it is desired to achieve straight or curved nanowires. It has been previously shown that overexpressing CsgB in *E. coli* ΔcsgA strains yields short and straight polymers composed of CsgB which are also insoluble and bind to Congo Red (Bian et al., (1997) *EMBO J* 16:5827). Moreover, it has been shown that fusing periplasmic maltose-binding protein with CsgB (MBP-CsgB) in *E. coli* ΔcsgB cells results in curved fibers that are thicker (~10-15 nm) than wild-type fibers (Bian et al., (1997) *EMBO J* 16:5827). These studies are extended by placing CsgA, CsgB, and MBP-CsgB under independent inducible control in the same *E. coli* ΔcsgA ΔcsgB cells and modifying their relative levels of expression. The aforementioned results are first confirmed to produce straight and curved fibers. Then, by tuning the relative expression levels of CsgA, CsgB, and MBP-CsgB, it is expected that fibers with varying thickness and curvature are produced.

Localization

While curli fibers can normally be found at different locations on the cell surface, it would be beneficial for certain applications to control curli localization. For example, it may be desired to express one type of amyloid nanowires at the poles of bacteria and another type of nanowires along the length of bacteria. If nanowires that can be coated with magnetic materials are desired, it may be advantageous for these nanowires to be localized to the same area or opposing area as flagella to act as rudders so that swimming takes place in alignment with magnetic fields. Cells expressing MBP-CsgB in *E. coli* ΔcsgB cells produce fibers that are localized to the bacterial poles (Bian et al., (1997) *EMBO J* 16:5827). These results are confirmed and additional options are pursued for controlling nanowire localization. For example, the CsgB nucleator protein is fused with other cell-surface proteins that exhibit cellular polarization, such as IcsA. IcsA is an outer-membrane protein from in *Shigella* that is found at the cell poles when expressed heterologously in *E. coli* (Lybarger et al., (2001) *J Bacteriol* 183:3261).

Control Nanowire Release to Enable Continuous Fiber Production Cycles

In their native setting, curli fibers are continuously elongated with the addition of new CsgA subunits. While this may be beneficial for bacteria in natural settings, it may be desired to produce curli fibers with defined lengths for nanowire applications. To do so, a method is developed to release amyloid fibers so that they can be easily collected and purified for downstream use while resetting the bacteria to continue producing new fibers (FIG. 12).

Kolodkin-Gal et al. recently demonstrated that D-amino acids can trigger biofilm disassembly by causing the detachment of amyloid fibrils in *Bacillus subtilis* (Kolodkin-Gal et al., (2010) *Science* 328:627). They found that mixtures of D-leucine, D-methionine, D-tyrosine, and D-tryptophan were the most effective signals for fiber release. Id. In addition, they demonstrated that the deletion of ylmE and racX, two genes with similarity to known racemases that convert L-amino acids to D-amino acids, prevents biofilm release presumably by decreasing the synthesis of D-amino acids. Id. Conversely, cells overexpressing ylmE were unable to form biofilms presumably by synthesizing large amounts of D-amino acids that detach amyloid fibers from cell surfaces. Id.

D-amino acids can also serve as a useful signal for the release of curli nanowires from bacterial cells which would enable a continuous fiber production cycle (FIG. 12). To implement this production cycle, engineered bacteria are loaded into microfluidics chips where time-varying chemical inputs are applied and effluent material is collected (e.g., from CellASIC, Inc. through a collaboration). Inducers for curli synthesis are applied followed by the addition of different combinations of D-leucine, D-methionine, D-tyrosine, and D-tryptophan. If none of these amino acids detach curli fibers, the search is expanded to other D-amino acids. In addition to testing exogenous D-amino acids, it is investigated whether the expression of amino-acid racemases can release curli fibers. *B. subtilis* ylmE and racX are cloned as well as *E. coli* racemases or putative racemases (e.g., alr, dadX, mud, yhfX, and ygeA) into *E. coli* expression vectors and their expression is induced. Using TEM to image the effluent channels, it is determined whether fibers are detached from cell surfaces by the application of D-amino acids or expression of racemases.

If it is not possible to release curli fibers with D-amino acids or racemases, this ability is screened for in the comprehensive ASKA library of inducible *E. coli* open reading frame (ORF) clones (Kitagawa et al., (2005) *DNA Res* 12:291). This screen is carried out in a high-throughput fashion by comparing quantitative CR binding by curli-expressing cells with induced ORF expression versus curli-expressing cells with non-induced ORF expression. Cells containing ORFs that can release curli fibers should have high CR binding in the non-induced state and low CR binding in the induced state. It is expected that successful hits are uncovered because bacterial have the natural ability to detach themselves from biofilms by separating themselves from functional curli amyloids within biofilms (Flemming et al., (2010) *Nat Rev Microbiol* 8:623).

Example 2

Figure 13:
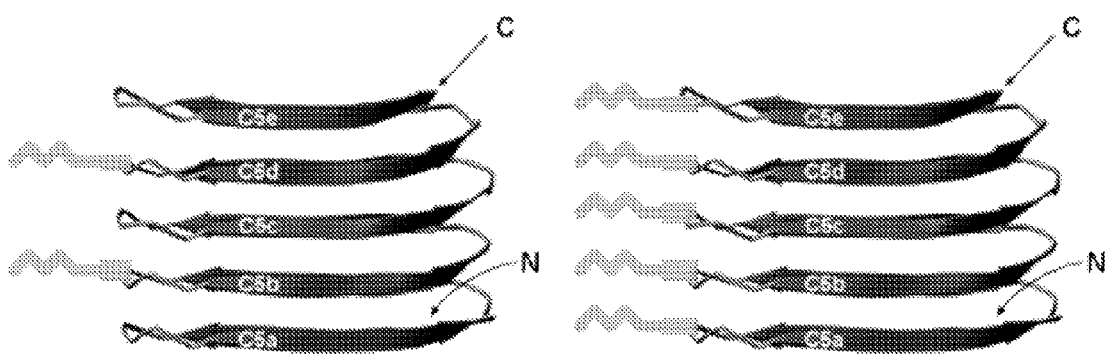
FIG. 13 shows that inserting multiple inorganic-material-binding peptides (shown in light grey) throughout the CsgA structure can enable controlled and high-density metal binding.

Engineering of Multifunctional Bacterial Nanowires with Organic-Inorganic Interfaces Construct Inorganic-Material-Binding Nanowires A characteristic feature of bacterial nanowires described herein is their ability to interface organic and non-organic materials. Curli amyloid fibers are designed that display peptides which can bind and nucleate inorganic nanomaterials, such as gold, quantum dots, and iron oxide. These peptides are inserted into surface-exposed regions identified as described above. Using the mapping data, the density and spacing between successive material-binding peptides can be controlled (FIG. 13). For example, the distance between β-strands within β-sheets in curli amyloids is ~4.7 Å while the distance between layers of β-sheets in curli amyloids is ~9 Å (Shewmaker et al., (2009) *J Biol Chem* 284:25065). Thus, if peptides are displayed at multiple locations along the curli amyloid structure, it should be possible to achieve inter-peptide distances on the order of nanometers to sub-nanometers.

A gold-binding peptide (Au-BP) has been displayed at the C-terminal of CsgA to form CsgA-Au-BP. The Au-BP used (LKAHLPPSRLPS) was previously selected using phage display by Nam et al. (Nam et al., (2006) *Science* 312:885). As shown herein, gold particles were found to bind to CsgA-Au-BP fibers (FIG. 14A) in greater density than native curli fibers or curli fibers that displayed the FLAG affinity tag (FIG. 14B). To achieve this, CsgA-Au-BP was expressed from its native *E. coli* promoter in a low copy vector (pZS32 from Lutz and Bujard (Lutz et al., (1997) *Nucleic Acids Res* 25:1203) transformed into BW25113 ΔcsgA::kanR (Baba et al., (2006) *Mol Syst Biol* 2:20060008). 15 μL of stationary culture grown in YESCA media was spotted onto YESCA agar plates (30 μg/ml kanamycin, 12.5 μg/ml chloramphenicol) and grown for 72-96 hours at 30° C. to induce expression of curli fibers. The resulting colonies were scraped and resuspended in 500 μL of 1× phosphate-buffered saline (PBS). 5 μL of the bacteria was then spun down at 16,000 rcf for 5 minutes. The resulting supernatant was removed and the cells were resuspended in 200 μL of 5 nm gold colloid ($5 \times 10^{13}$/ml, Ted Pella) or in a 10-fold dilution thereof. This sample was sonicated for 10 minutes (Branson 5510 Ultrasonic Cleaner) and incubated for 24-48 hours at room temperature prior to TEM (FIG. 14).

ZnS-binding/nucleating peptides (ZnS-BP) and CdS-binding/nucleating peptides (CdS-BP) have also been displayed on curli fibers to nucleate ZnS and CdS formation. For these experiments, ZnS-BP (CNNPMHQNC) and CdS-BP (SLTPLTTSHLRS) from Mao et al. (Mao et al., (2004) *Science* 303:213) were used. ZnS-BP and CdS-BP were fused at the C-terminal of CsgA to form CsgA-ZnS-BP and CsgA-CdS-BP. These engineered CsgA subunits were expressed from low copy vectors in BW25113 ΔcsgA::kanR, grown on YESCA plates, harvested, and centrifuged as described for CsgA-Au-BP. Cells expressing CsgA-ZnS-BP and CsgA-CdS-BP formed amyloid fibrils that bound to CR. To test their ability to nucleate ZnS and CdS formation, samples were resuspended in 500 μL aqueous solution of $ZnCl_2$ (1 mM) or $CdCl_2$ (1 mM), sonicated for 10 minutes (Branson 5510 Ultrasonic Cleaner), and allowed to interact for 12 hours at room temperature. 500 μL aqueous solution of $Na_2S$ (1 mM) was added and the temperature was lowered to 0° C. for 24 hours to enhance curli-ZnS or curli-CdS interactions, after which samples were aged at room temperature for 12 hours.

Using TEM, it was found that curli nanowires composed of CsgA ZnS BP nucleated zinc sulfate formation (FIG. 44A) and those composed of CsgA CdS BP nucleated cadmium sulfate formation (FIG. 44B). These semiconductor materials also displayed fluorescence (FIG. 44E, 44F).

These promising results can be extended to create curli fibers that can bind and nucleate other useful materials such as iron oxide, silver nanoparticles, cobalt oxide, cobalt platinum, and iron platinum. To do so, curli are functionalized with peptides isolated using filamentous phage display (Mao et al., (2004) *Science* 303:213; Nam et al., (2006) *Science* 312:885; Baldwin et al., (2006) *Am Chem Soc* 128:2162). The conditions necessary for material binding and nucleation are also characterized by varying parameters such as material concentration, temperature, pH, and incubation time. These experiments allow optimization of the creation of interfaces between living and non-living devices.

Since the peptides used thus far were isolated by phage display, they may not be optimal for displaying inorganic-material binding peptides on curli amyloid fibers due to context-dependent effects (Peelle et al., (2005) *Langmuir* 21:6929; Peelle et al., (2005) *Acta Biomater* 1:145). If phage-displayed-based peptides do not mediate tight binding of inorganic materials, the curli amyloid system is utilized as a cell-display system to identify new peptides. This is possible because foreign peptides can be displayed on the surface of curli fibers and because the fiber-peptide complexes are physically linked to the cells that encode their production. Protocols are adapted for phage-display systems and other cell-display systems to express curli-displayed peptide libraries followed by binding, selection, amplification, and identification of new material-binding peptides.

In some cases, it may be desired to minimize the non-specific binding of curli fibers to certain materials. This can be done by displaying peptides which have been previously shown to block non-specific binding. For example, to minimize non-specific binding of gold nanoparticles by phages, Nam et al. used phage-displayed tetra-glutamate peptides (Nam et al., (2006) *Science* 312:885). If non-specific interactions appear to be problematic, a randomized library of curli-displayed peptides is constructed and the ability of these peptides to block non-specific material binding is tested. The curli-display system described above can also be utilized to select against phage sequences which promote tight binding to materials (Peelle et al., (2005) *Acta Biomater* 1:145).

Engineering Conductive Nanowires for Enhanced Electron Transport in Biofilms

Microbial fuel cells are a promising technology for the sustainable generation of energy. Anode-respiring bacteria (ARBs) can be used to produce electrical current for microbial fuel cells by oxidizing organic substrates and transferring extracellular electrons to anodes (Torres et al., (2010) *FEMS Microbiol Rev* 34:3). Anodes subsequently transfer electrons to cathodes, where different chemical species can act as the terminal electron acceptors. Maximal power generation by microbial fuel cells requires high current density production with low anode potential losses (Tones et al., (2010) *FEMS Microbiol Rev* 34:3; Tones et al., (2008) *Biotechnol Bioeng* 100:872). The electrical potential difference between donor electrons and the anode is the anode potential loss and is equal to the sum of intracellular potential losses (which contributes energy to ARBs) and extracellular potential losses (composed of energy losses associated with the transmission of electrons to anode interfaces plus energy losses associated with reactions at anode interfaces) (Tones et al., (2010) *FEMS Microbiol Rev* 34:3).

Three methods are believed to be involved in extracellular electron transfer, including direct contact between cells and anodes, soluble electron shuttles, and conduction through solid constituents of bacterial biofilms. Electron transfer via direct contact between cells and anodes cannot achieve high current density since only a monolayer of cells can associate with the anode surface. Similarly, soluble electron shuttles are susceptible to current generation limitations and anode potential losses due to their slow diffusion from cells to anodes and back. In contrast, electrical conduction through biofilms enable distant bacteria to transfer electrons to anodes and limit potential losses (Tones et al., (2005) *FEMS Microbiol Rev* 34:3). Biofilm conduction in ARB monocultures is thought to be due to microbial nanowires synthesized by the ARBs themselves (Tones et al., (2005) *FEMS Microbiol Rev* 34:3; Reguera et al., (2005) Nature 435:1098; Gorby et al., (2006) *Proc Natl Acad Sci USA* 103:11358).

Since anode-respiring bacteria use electrical potential to power their intracellular machinery, metabolically expensive processes such as synthesizing nanowires can potentially decrease the efficiency of microbial fuel cells. Instead of using a monoculture of ARBs which must simultaneously synthesize nanowires and generate electrons, mixed biofilms composed of ARBs specializing in electron generation plus synthetic bacteria specializing in conductive nanowire production are used. Synthetic bacteria associated with the invention can potentially use energy sources that do not overlap with ARBs. Alternatively, mixed biofilms can be created composed of conductive bacteria plus cyanobacteria that exhibit light-dependent electrogenic activity and thereby attain direct sunlight to electricity conversion (Pisciotta et al., (2010) *PLoS One* 5:e10821).

To construct conductive biofilms, *E. coli* are engineered to express conductive curli nanowires. Two distinct approaches are pursued for the production of conductive bacterial nanowires: 1) express metal-binding peptides on the surface of curli to nucleate conductive materials and 2) display conductive cytochromes on the surface of curli. To measure the electrical properties of engineered versus wild-type curli and biofilms, a lab-on-a-chip system is used that contains electrodes for measuring electrical signals. Opposing electrodes are used that are separated by varying gap sizes that can be spanned by individual curli fibers or accommodate multiple bacterial cells. These electrodes are coated with biocompatible conductive materials such as platinum, gold, indium tin oxide, or titanium. The DC current-voltage characteristics and the AC impedance response of curli fibers and biofilms are determined using these devices. It is expected that cells which express conductive nanowires will have decreased electrical impedances compared with wild-type cells.

Using metal-binding peptides described herein, conductive nanowires are produced by binding conductive materials to curli amyloid fibers. For example, gold-binding and silver-binding peptides can be expressed in high density along curli fibers (Scheibel et al., (2003) *Proc Natl Acad Sci USA* 100:4527). Multiple insertion sites for metal-binding peptides within CsgA and different combinations of metals are tested. These experiments are performed in conditions that maintain cellular viability in contrast with other applications where the survival of bacterial micro-robots (BMRs) is not as important. It is expected that a high density of metal-binding peptides and metals will reduce the resistivity of curli nanowires and the associated *E. coli* biofilms.

Many natural biological systems utilize chains of closely-spaced redox centers (<14 Å) for electron transport over long distances (~9 nm) (Leys et al., (2004) *Curr Opin Struct Biol* 14:642). To mimic these systems and achieve conduction using biomolecules, bacterial cytochromes (such as cytochrome $b_{562}$) are fused to surface-exposed locations in CsgA (Baldwin et al., (2006) *J Am Chem Soc* 128:2162. For optimal electron transport, the cytochromes should be as closely spaced as possible and therefore, multiple cytochrome units are fused within the CsgA subunit at sites that can accept foreign inserts. The CsgA-cytochrome fusions may be poorly secreted due to the additional residues of the cytochromes (~100 amino acids). If this is the case, deletions can be made in CsgA that still preserve curli formation. For example, repeat 2 in CsgA (CsgA R2 in FIG. 6) is not necessary for in vivo curli formation and can be deleted to decrease the total complex size (Wang et al., (2008) *J Biol Chem* 283:21530).

Designing Electronic Signaling Pathways in Bacteria with Conductive Nanowires

Intercellular bacterial communication is usually based on diffusible quorum-sensing chemicals (Waters et al., (2005) *Annu Rev Cell Dev Biol* 21:319). Diffusible molecules are useful for broadcasting signals but have limited signaling range, fidelity, and speed. Moreover, diffusible chemical signals require specialized chemical sensor interfaces in order to be detected by electronic systems which form the bulk of modern computation. Thus, alternative signaling modalities for cell-cell or cell-device communications would be useful for many applications, including biocomputation and biosensors.

Here, electrical signaling pathways in *E. coli* are engineered to transmit electrical signals to non-living devices. Recently, Jensen et al. showed that the heterologous expression of the mtrCAB cluster from *Shewanella oneidensis* MR-1 in *E. coli* enables the transport of intracellular electrons to the extracellular space (Jensen et al., (2010) *Proc Natl Acad Sci USA* 107:19213). Similar to power generation in microbial fuel cells, exporting electrons for electrical signaling in the absence of long-range electron transport limits the current and voltage that can be delivered to external electrodes.

Thus, the mtrCAB system is integrated into *E. coli* that display conductive nanowires to enable long-range electrical signaling (FIG. 16). By modulating mtrCAB expression with inducible synthetic promoters, it may be possible to convert time-varying chemical inputs into long-range electrical outputs that can be detected by external electrodes and electronics.

To test this system, engineered cells are grown in microfluidics systems integrated with microelectrode arrays. This system can capture single to hundreds of cells in nanoliter-sized chambers and deliver time-varying chemical inducers to these chambers via microfluidic channels. *E. coli* expressing conductive curli fibers and mtrCAB, under the control of inducible promoters, are grown in these channels. Voltage and current generated by the synthetic cells are measurable using microelectrodes coated with conductive materials. The expression of mtrCAB is modulated with time-varying input signals and the resulting changes in voltage and current are measured. Since this proof-of-concept system relies on transcriptional control to regulate electrical signal output, it is expected that the optimal translation of chemical inputs to electrical outputs will occur at the time scale of hours. Electrical outputs can also be designed that can be modulated on shorter time scales using synthetic gene circuits which are triggered by light, heat, magnetism, electrical fields, or changes in protein phosphorylation.

Example 3

Programming Synthetic Gene Circuits for Nanoscale, Microscale, and Macroscale Patterning Characterization of the Assembly Rates of Bacterial Nanowires In order to achieve detailed nanoscale patterning, the assembly rate for curli fibers is characterized. CsgA is expressed under inducible synthetic promoters such as pLtetO and pLlacO (Lutz et al., (1997) *Nucleic Acids Res* 25:1203). These plasmids are induced for CsgA expression and assayed using quantitative Congo Red binding at 480 nm and electron microscopy for curli fiber formation over several days or more. The change in dimensions for curli amyloids is characterized over time with a range of inducer concentrations. It is expected that a continuous increase in quantitative CR binding and fiber elongation via TEM will be measured over several days. It is also expected that fiber assembly rates will exhibit a dependence on inducer concentrations.

Control of Anisotropic Patterning of Bacterial Nanowires at the Nanoscale

Nanowire platforms described herein can achieve detailed nanoscale patterning by coupling the expression of curli subunits to synthetic gene circuits, such as promoters, switches, and oscillators. Anisotropic patterning of nanomaterials is hard to achieve using other means due to the difficulty in specifying controlled interactions between nanowire components. This difficulty is heightened at length scales greater than single subunit dimensions.

Curli fibers are constructed with several proof-of-concept nanopatterns, including an interdigitated pattern, a bipartite pattern, a multi-segmented pattern, and a repeating multi-segmented pattern (FIG. 17).

Interdigitated patterning is implemented by the simultaneous expression of different curli subunits from inducible promoters (FIG. 17A). Bipartite patterning is validated by placing different curli subunits under the control of two inducible promoters which are activated in sequential order or to the two outputs of a genetic toggle switch (FIG. 17B). Multi-segmented designs are achieved by extending the bipartite patterning method to more than two inducible promoters which are sequentially activated (FIG. 17C). Finally, the multi-segmented pattern is extended to a repeating pattern by coupling the production of different curli subunits to genetic oscillators (FIG. 17D) (Elowitz et al., (2000) *Nature* 403:335; Stricker et al., (2008) *Nature* 456:516). In this design, the temporal periodicity of the oscillators translates to spatial periodicity in the nanowires.

It is confirmed that curli amyloids are formed by these patterning circuits by plating cells onto CR agar and performing quantitative CR binding assays. To validate that the expected nanopatterns are being formed, TEM is utilized. By designing subunits which bind to nanoparticles of various sizes, different subunit types are distinguished by TEM. For example, for the interdigitated nanowires and bipartite nanowires, a wild-type CsgA subunit with a His-tagged subunit is used. Au-Ni-NTA particles should only bind to the His-tagged subunits allowing for verification of the success of interdigitated or bipartite patterns. For designs that involve more than two different subunit types (e.g., FIG. 17C-D), a wild-type CsgA subunit, a His-tagged CsgA subunit, and CsgA subunits engineered to bind to non-gold nanoparticles of different sizes are used. Alternatively, different affinity tags are displayed on CsgA subunits (e.g., HA and FLAG tags) and gold-labeled antibodies are used to probe the nanopatterns.

Combining Bacterial Nanowire Patterning with Quorum-Sensing-Based and Light-Based Patterning at the Microscale and Macroscale To achieve self-organizing materials at length scales across many orders of magnitude, complex nanopatterning capabilities are combined with microscale and macroscale patterning capabilities by connecting the activation of curli-expressing circuits with quorum-sensing circuits and light-sensing circuits. This is a major challenge in nanotechnology that is difficult to solve using current means. Quorum-sensing circuits enable the self-organization of bacterial micro-robots which produce nanowires. Light-sensing circuits allow the use of masks to achieve user-directed patterning. By combining these two methods, the patterning of biomaterials across multiple length scales can be achieved. The ability to pattern nanomaterials across many orders of magnitude is critical for real-world applications such as next-generation armor, electrodes, solar cells, and electronics.

Quorum-sensing sender and receiver circuits are used to engineer self-organizing bacteria with microscale patterns of curli production (FIG. 18A) (Lu (2010) *Bioengineered Bugs* 1:1; Lu et al., (2009) *Nat Biotechnol* 27:1139). Previous work from Ron Weiss' lab has shown that synthetic quorum sensing circuits in bacteria can be used to create self-organizing systems with different patterns such as bullseyes, ellipses, and clovers (Basu et al., (2005) *Nature* 434:1130). Recently, Chris Voigt's lab demonstrated that quorum sensing can be used to program multicellular digital logic (Tamsir et al., (2011) *Nature* 469(7329):212).

Here, the fluorescent protein outputs in these quorum sensing systems are replaced with a transcriptional activator which controls the expression of curli fibers. This allows the creation of microscale and macroscale patterns of expression for nanowires based on bacterial self-organization or even using digital logic processing (FIG. 18A). As a proof-of-concept, bullseye patterns are created with alternating conductive and non-conductive nanowires which may be useful as capacitors.

User-defined microscale and macroscale patterning of curli nanowire production is achieved by employing light to selectively induce curli subunit synthesis. For example, Kobayashi et al. built a toggle switch that can be switched by ultraviolet (UV) radiation (FIG. 18B) (Kobayashi et al., (2004) *Proc Natl Acad Sci USA* 101:8414). Alternatively, the Voigt lab has developed visible-light-sensing transcriptional control in bacteria (Levskaya et al., (2005) *Nature* 438:441). UV-inducible toggle switches and visible-light-inducible promoters are designed to control the expression of curli. Thus, UV and visible light are used in combination with optical masks to define different areas of curli production (FIG. 18B).

To achieve stable curli expression, visible-light-inducible promoters are connected to toggle switches or recombinase-based switches. For example, we have developed a modular design for heritable, stable, and interoperable memory devices called Single Invertase Memory Modules (SIMMs) (Lu et al., (2009) *Nat Biotechnol* 27:1139; Friedland et al., (2009) *Science* 324:1199). At the core of a SIMM is a recombinase that can invert DNA between two oppositely-oriented cognate recognition sites. Upon expression of the recombinase by an upstream promoter, the entire SIMM is inverted between the recognition sites, representing the flipping of a digital bit. Due to the inverted orientation of the recombinase gene with respect to the upstream promoter, further expression of recombinase protein ceases and DNA orientation is fixed. This design stores heritable memory information in the physical orientation of DNA. Stability is conferred by sandwiching the recombinase gene between its own recombinase recognition sites. Interoperability is achieved by the natural ability of recombinase proteins to recognize and focus their activity upon specific DNA sequences in recombinase-recognition sites.

These synthetic quorum-sensing and light-inducible circuits in *E. coli* are constructed and characterized using gene synthesis and available parts at the MIT Registry of Standard Biological Parts. A simple visual assay for the proper operation of these patterning circuits is to plate a lawn of cells on CR agar and observe the patterns of red and white which indicate the presence and absence of curli fibers, respectively. These results are confirmed using TEM with nanowires labeled with nanoparticles using the techniques described herein. Finally, to demonstrate multiscale patterning, these quorum-sensing and light-inducible circuits are connected with the repeating multi-segmented nanopatterning circuit described herein.

Example 4

Materials and Methods for Examples 1-3

DNA constructs were cloned into the pZS32-GFP plasmid (received from Jim Collins' Laboratory, Boston University, Boston, Mass.), containing the pLlacO promoter, described in Lutz and Bujard (1997) *Nucleic Acids Research* 25(6): 1203-10. The S_ori origin of replication was ligated into the pZS32-GFP plasmid to generate a low copy version of the plasmid.

The sequence of the modified pZS32-GFP plasmid is as follows (SEQ ID NO:4):

```
CTCGAGATGCTAGCAATTGTGAGCGGATAACAATTGACATTGTGAGCGGA

TAACAAGATACTGAGCACATCAGCAGGACGCACTGACCTTAATTAAAAGA

ATTCATTAAAGAGGAGAAAGGTACCATGCGTAAAGGAGAAGAACTTTTCA

CTGGAGTTGTCCCAATTCTTGTTGAATTAGATGGTGATGTTAATGGGCAC

AAATTTTCTGTCAGTGGAGAGGGTGAAGGTGATGCAACATACGGAAAACT

TACCCTTAAATTTATTTGCACTACTGGAAAACTACCTGTTCCATGGCCAA

CACTTGTCACTACTTTCGGTTATGGTGTTCAATGCTTTGCGAGATACCCA

GATCATATGAAACAGCATGACTTTTTCAAGAGTGCCATGCCCGAAGGTTA

TGTACAGGAAAGAACTATATTTTTCAAAGATGACGGGAACTACAAGACAC

GTGCTGAAGTCAAGTTTGAAGGTGATACCCTTGTTAATAGAATCGAGTTA

AAAGGTATTGATTTTAAAGAAGATGGAAACATTCTTGGACACAAATTGGA

ATACAACTATAACTCACACAATGTATACATCATGGCAGACAAACAAAAGA

ATGGAATCAAAGTTAACTTCAAAATTAGACACAACATTGAAGATGGAAGC

GTTCAACTAGCAGACCATTATCAACAAAATACTCCAATTGGCGATGGCCC

TGTCCTTTTACCAGACAACCATTACCTGTCCACACAATCTGCCCTTTCGA

AAGATCCCAACGAAAAGAGAGACCACATGGTCCTTCTTGAGTTTGTAACA

GCTGCTGGGATTACACATGGCATGGATGAACTATACAAATAAAAGCTTGA

TATCGAATTCCTGCAGCCCGGGGGATCCCATGGTACGCGTGGCATCAAAT

AAAACGAAAGGCTCAGTCGAAAGACTGGGCCTTTCGTTTTATCTGTTGTT

TGTCGGTGAACGCTCTCCTGAGTAGGACAAATCCGCCGCCCTAGACCTAG

GGTACGGGTTTTGCTGCCCGCAAACGGGCTGTTCTGGTGTTGCTAGTTTG

TTATCAGAATCGCAGATCCGGCTTCAGGTTTGCCGGCTGAAAGCGCTATT

TCTTCCAGAATTGCCATGATTTTTTCCCCACGGGAGGCGTCACTGGCTCC
```

```
CGTGTTGTCGGCAGCTTTGATTCGATAAGCAGCATCGCCTGTTTCAGGCT
GTCTATGTGTGACTGTTGAGCTGTAACAAGTTGTCTCAGGTGTTCAATTT
CATGTTCTAGTTGCTTTGTTTTACTGGTTTCACCTGTTCTATTAGGTGTT
ACATGCTGTTCATCTGTTACATTGTCGATCTGTTCATGGTGAACAGCTTT
AAATGCACCAAAAACTCGTAAAAGCTCTGATGTATCTATCTTTTTTACAC
CGTTTTCATCTGTGCATATGGACAGTTTTCCCTTTGATATCTAACGGTGA
ACAGTTGTTCTACTTTTGTTTGTTAGTCTTGATGCTTCACTGATAGATAC
AAGAGCCATAAGAACCTCAGATCCTTCCGTATTTAGCCAGTATGTTCTCT
AGTGTGGTTCGTTGTTTTTGCGTGAGCCATGAGAACGAACCATTGAGATC
ATGCTTACTTTGCATGTCACTCAAAAATTTTGCCTCAAAACTGGTGAGCT
GAATTTTTGCAGTTAAAGCATCGTGTAGTGTTTTTCTTAGTCCGTTACGT
AGGTAGGAATCTGATGTAATGGTTGTTGGTATTTTGTCACCATTCATTTT
TATCTGGTTGTTCTCAAGTTCGGTTACGAGATCCATTTGTCTATCTAGTT
CAACTTGGAAAATCAACGTATCAGTCGGGCGGCCTCGCTTATCAACCACC
AATTTCATATTGCTGTAAGTGTTTAAATCTTTACTTATTGGTTTCAAAAC
CCATTGGTTAAGCCTTTTAAACTCATGGTAGTTATTTTCAAGCATTAACA
TGAACTTAAATTCATCAAGGCTAATCTCTATATTTGCCTTGTGAGTTTTC
TTTTGTGTTAGTTCTTTTAATAACCACTCATAAATCCTCATAGAGTATTT
GTTTTCAAAAGACTTAACATGTTCCAGATTATATTTTATGAATTTTTTTA
ACTGGAAAAGATAAGGCAATATCTCTTCACTAAAAACTAATTCTAATTTT
TCGCTTGAGAACTTGGCATAGTTTGTCCACTGGAAAATCTCAAAGCCTTT
AACCAAAGGATTCCTGATTTCCACAGTTCTCGTCATCAGCTCTCTGGTTG
CTTTAGCTAATACACCATAAGCATTTTCCCTACTGATGTTCATCATCTGA
GCGTATTGGTTATAAGTGAACGATACCGTCCGTTCTTTCCTTGTAGGGTT
TTCAATCGTGGGGTTGAGTAGTGCCACACAGCATAAAATTAGCTTGGTTT
CATGCTCCGTTAAGTCATAGCGACTAATCGCTAGTTCATTTGCTTTGAAA
ACAACTAATTCAGACATACATCTCAATTGGTCTAGGTGATTTTAATCACT
ATACCAATTGAGATGGGCTAGTCAATGATAATTACTAGTCCTTTTCCTTT
GAGTTGTGGGTATCTGTAAATTCTGCTAGACCTTTGCTGGAAAACTTGTA
AATTCTGCTAGACCCTCTGTAAATTCCGCTAGACCTTTGTGTGTTTTTTT
TGTTTATATTCAAGTGGTTATAATTTATAGAATAAAGAAAGAATAAAAAA
AGATAAAAGAATAGATCCCAGCCCTGTGTATAACTCACTACTTTAGTCA
GTTCCGCAGTATTACAAAAGGATGTCGCAAACGCTGTTTGCTCCTCTACA
AAACAGACCTTAAAACCCTAAAGGCTTAAGTAGCACCCTCGCAAGCTCGG
GCAAATCGCTGAATATTCCTTTTGTCTCCGACCATCAGGCACCTGAGTCG
CTGTCTTTTTCGTGACATTCAGTTCGCTGCGCTCACGGCTCTGGCAGTGA
ATGGGGGTAAATGGCACTACAGGCGCCTTTTATGGATTCATGCAAGGAAA
CTACCCATAATACAAGAAAAGCCCGTCACGGGCTTCTCAGGGCGTTTTAT
GGCGGGTCTGCTATGTGGTGCTATCTGACTTTTTGCTGTTCAGCAGTTCC
TGCCCTCTGATTTTCCAGTCTGACCACTTCGGATTATCCCGTGACAGGTC
ATTCAGACTGGCTAATGCACCCAGTAAGGCAGCGGTATCATCAACAGGCT
TACCCGTCTTACTGTCCCTAGTGCTTGGATTCTCACCAATAAAAAACGCC
CGGCGGCAACCGAGCGTTCTGAACAAATCCAGATGGAGTTCTGAGGTCAT
TACTGGATCTATCAACAGGAGTCCAAGCGAGCTCGATATCAAATTACGCC
CCGCCCTGCCACTCATCGCAGTACTGTTGTAATTCATTAAGCATTCTGCC
GACATGGAAGCCATCACAGACGGCATGATGAACCTGAATCGCCAGCGGCA
TCAGCACCTTGTCGCCTTGCGTATAATATTTGCCCATGGTGAAAACGGGG
GCGAAGAAGTTGTCCATATTGGCCACGTTTAAATCAAAACTGGTGAAACT
CACCCAGGGATTGGCTGAGACGAAAAACATATTCTCAATAAACCCTTTAG
GGAAATAGGCCAGGTTTTCACCGTAACACGCCACATCTTGCGAATATATG
TGTAGAAACTGCCGGAAATCGTCGTGGTATTCACTCCAGAGCGATGAAAA
CGTTTCAGTTTGCTCATGGAAAACGGTGTAACAAGGGTGAACACTATCCC
ATATCACCAGCTCACCGTCTTTCATTGCCATACGGAATTCCGGATGAGCA
TTCATCAGGCGGGCAAGAATGTGAATAAAGGCCGGATAAAACTTGTGCTT
ATTTTTCTTTACGGTCTTTAAAAAGGCCGTAATATCCAGCTGAACGGTCT
GGTTATAGGTACATTGAGCAACTGACTGAAATGCCTCAAAATGTTCTTTA
CGATGCCATTGGGATATATCAACGGTGGTATATCCAGTGATTTTTTTCTC
CATTTTAGCTTCCTTAGCTCCTGAAAATCTCGATAACTCAAAAAATACGC
CCGGTAGTGATCTTATTTCATTATGGTGAAAGTTGGAACCTCTTACGTGC
CGATCAACGTCTCATTTTCGCCAGATATCGACGTCTAAGAAACCATTATT
ATCATGACATTAACCTATAAAAATAGGCGTATCACGAGGCCCTTTCGTCT
TCAC
```

The sequence of CsgA is represented by SEQ ID NO:122, as follows:

```
ATGAAACTTTTAAAAGTAGCAGCAATTGCAGCAATCGTATTCTCCGGTAG
CGCTCTGGCAGGTGTTGTTCCTCAGTACGGCGGCGGCGGTAACCACGGTG
GTGGCGGTAATAATAGCGGCCCAAATTCTGAGCTGAACATTTACCAGTAC
GGTGGCGGTAACTCTGCACTTGCTCTGCAAACTGATGCCCGTAACTCTGA
CTTGACTATTACCCAGCATGGCGGCGGTAATGGTGCAGATGTTGGTCAGG
GCTCAGATGACAGCTCAATCGATCTGACCCAACGTGGCTTCGGTAACAGC
GCTACTCTTGATCAGTGGAACGGCAAAAATTCTGAAATGACGGTTAAACA
GTTCGGTGGTGGCAACGGTGCTGCAGTTGACCAGACTGCATCTAACTCCT
CCGTCAACGTGACTCAGGTTGGCTTTGGTAACAACGCGACCGCTCATCAG
TACTAA
```

CsgA was subcloned into KpnI and MluI sites within pZS32-GFP, generating pZS32-CsgA, using the following primers:

pR_CsgA:
(SEQ ID NO: 5)
5'-CTACGCGTGATGTATTAGTACTGATGAGCGG-3'
TmNN: 64/53 (aycP2)

pF_CsgA:
(SEQ ID NO: 6)
5'-GAGGTACC AT GAAACTTTTA AAAGTAGCAG C-3'
TmNN: 59/50 (aycP4)

The sequence of pZS32-CsgA is as follows (SEQ ID NO:7):

CTCGAGATGCTAGCAATTGTGAGCGGATAACAATTGACATTGTGAGCGGA
TAACAAGATACTGAGCACATCAGCAGGACGCACTGACCTTAATTAAAAGA
ATTCATTAAAGAGGAGAAAGGTACCATGAAACTTTTAAAAGTAGCAGCAA
TTGCAGCAATCGTATTCTCCGGTAGCGCTCTGGCAGGTGTTGTTCCTCAG
TACGGCGGCGGCGGTAACCACGGTGGTGGCGGTAATAATAGCGGCCCAAA
TTCTGAGCTGAACATTTACCAGTACGGTGGCGGTAACTCTGCACTTGCTC
TGCAAACTGATGCCCGTAACTCTGACTTGACTATTACCCAGCATGGCGGC
GGTAATGGTGCAGATGTTGGTCAGGGCTCAGATGACAGCTCAATCGATCT
GACCCAACGTGGCTTCGGTAACAGCGCTACTCTTGATCAGTGGAACGGCA
AAAATTCTGAAATGACGGTTAAACAGTTCGGTGGTGGCAACGGTGCTGCA
GTTGACCAGACTGCATCTAACTCCTCCGTCAACGTGACTCAGGTTGGCTT
TGGTAACAACGCGACCGCTCATCAGTACTAATACATCACGCGTGGCATCA
AATAAAACGAAAGGCTCAGTCGAAAGACTGGGCCTTTCGTTTTATCTGTT
GTTTGTCGGTGAACGCTCTCCTGAGTAGGACAAATCCGCCGCCCTAGACC
TAGGGTACGGGTTTTGCTGCCCGCAAACGGGCTGTTCTGGTGTTGCTAGT
TTGTTATCAGAATCGCAGATCCGGCTTCAGGTTTGCCGGCTGAAAGCGCT
ATTTCTTCCAGAATTGCCATGATTTTTTCCCCACGGGAGGCGTCACTGGC
TCCCGTGTTGTCGGCAGCTTTGATTCGATAAGCAGCATCGCCTGTTTCAG
GCTGTCTATGTGTGACTGTTGAGCTGTAACAAGTTGTCTCAGGTGTTCAA
TTTCATGTTCTAGTTGCTTTGTTTTACTGGTTTCACCTGTTCTATTAGGT
GTTACATGCTGTTCATCTGTTACATTGTCGATCTGTTCATGGTGAACAGC
TTTAAATGCACCAAAAACTCGTAAAAGCTCTGATGTATCTATCTTTTTTA
CACCGTTTTCATCTGTGCATATGGACAGTTTTCCCTTTGATATCTAACGG
TGAACAGTTGTTCTACTTTTGTTTGTTAGTCTTGATGCTTCACTGATAGA
TACAAGAGCCATAAGAACCTCAGATCCTTCCGTATTTAGCCAGTATGTTC
TCTAGTGTGGTTCGTTGTTTTTGCGTGAGCCATGAGAACGAACCATTGAG
ATCATGCTTACTTTGCATGTCACTCAAAAATTTTGCCTCAAAACTGGTGA
GCTGAATTTTTGCAGTTAAAGCATCGTGTAGTGTTTTTCTTAGTCCGTTA
CGTAGGTAGGAATCTGATGTAATGGTTGTTGGTATTTTGTCACCATTCAT
TTTTATCTGGTTGTTCTCAAGTTCGGTTACGAGATCCATTTGTCTATCTA
GTTCAACTTGGAAAATCAACGTATCAGTCGGGCGGCCTCGCTTATCAACC
ACCAATTTCATATTGCTGTAAGTGTTTAAATCTTTACTTATTGGTTTCAA
AACCCATTGGTTAAGCCTTTTAAACTCATGGTAGTTATTTTCAAGCATTA

-continued

ACATGAACTTAAATTCATCAAGGCTAATCTCTATATTTGCCTTGTGAGTT
TTCTTTTGTGTTAGTTCTTTTAATAACCACTCATAAATCCTCATAGAGTA
TTTGTTTTCAAAAGACTTAACATGTTCCAGATTATATTTTATGAATTTTT
TTAACTGGAAAAGATAAGGCAATATCTCTTCACTAAAAACTAATTCTAAT
TTTTCGCTTGAGAACTTGGCATAGTTTGTCCACTGGAAAATCTCAAAGCC
TTTAACCAAAGGATTCCTGATTTCCACAGTTCTCGTCATCAGCTCTCTGG
TTGCTTTAGCTAATACACCATAAGCATTTTCCCTACTGATGTTCATCATC
TGAGCGTATTGGTTATAAGTGAACGATACCGTCCGTTCTTTCCTTGTAGG
GTTTTCAATCGTGGGGTTGAGTAGTGCCACACAGCATAAAATTAGCTTGG
TTTCATGCTCCGTTAAGTCATAGCGACTAATCGCTAGTTCATTTGCTTTG
AAAACAACTAATTCAGACATACATCTCAATTGGTCTAGGTGATTTTAATC
ACTATACCAATTGAGATGGGCTAGTCAATGATAATTACTAGTCCTTTTCC
TTTGAGTTGTGGGTATCTGTAAATTCTGCTAGACCTTTGCTGGAAAACTT
GTAAATTCTGCTAGACCCTCTGTAAATTCCGCTAGACCTTTGTGTGTTTT
TTTTGTTTATATTCAAGTGGTTATAATTTATAGAATAAAGAAAGAATAAA
AAAAGATAAAAAGAATAGATCCCAGCCCTGTGTATAACTCACTACTTTAG
TCAGTTCCGCAGTATTACAAAAGGATGTCGCAAACGCTGTTTGCTCCTCT
ACAAAACAGACCTTAAAACCCTAAAGGCTTAAGTAGCACCCTCGCAAGCT
CGGGCAAATCGCTGAATATTCCTTTTGTCTCCGACCATCAGGCACCTGAG
TCGCTGTCTTTTTCGTGACATTCAGTTCGCTGCGCTCACGGCTCTGGCAG
TGAATGGGGGTAAATGGCACTACAGGCGCCTTTTATGGATTCATGCAAGG
AAACTACCCATAATACAAGAAAAGCCCGTCACGGGCTTCTCAGGGCGTTT
TATGGCGGGTCTGCTATGTGGTGCTATCTGACTTTTTGCTGTTCAGCAGT
TCCTGCCCTCTGATTTTCCAGTCTGACCACTTCGGATTATCCCGTGACAG
GTCATTCAGACTGGCTAATGCACCCAGTAAGGCAGCGGTATCATCAACAG
GCTTACCCGTCTTACTGTCCCTAGTGCTTGGATTCTCACCAATAAAAAAC
GCCCGGCGGCAACCGAGCGTTCTGAACAAATCCAGATGGAGTTCTGAGGT
CATTACTGGATCTATCAACAGGAGTCCAAGCGAGCTCGATATCAAATTAC
GCCCCGCCCTGCCACTCATCGCAGTACTGTTGTAATTCATTAAGCATTCT
GCCGACATGGAAGCCATCACAGACGGCATGATGAACCTGAATCGCCAGCG
GCATCAGCACCTTGTCGCCTTGCGTATAATATTTGCCCATGGTGAAAACG
GGGGCGAAGAAGTTGTCCATATTGGCCACGTTTAAATCAAAACTGGTGAA
ACTCACCCAGGGATTGGCTGAGACGAAAACATATTCTCAATAAACCCTT
TAGGGAAATAGGCCAGGTTTTCACCGTAACACGCCACATCTTGCGAATAT
ATGTGTAGAAACTGCCGGAAATCGTCGTGGTATTCACTCCAGAGCGATGA
AAACGTTTCAGTTTGCTCATGGAAAACGGTGTAACAAGGGTGAACACTAT
CCCATATCACCAGCTCACCGTCTTTCATTGCCATACGGAATTCCGGATGA
GCATTCATCAGGCGGGCAAGAATGTGAATAAAGGCCGGATAAAACTTGTG
CTTATTTTTCTTTACGGTCTTTAAAAAGGCCGTAATATCCAGCTGAACGG
TCTGGTTATAGGTACATTGAGCAACTGACTGAAATGCCTCAAAATGTTCT

```
TTACGATGCCATTGGGATATATCAACGGTGGTATATCCAGTGATTTTTTT

CTCCATTTTAGCTTCCTTAGCTCCTGAAAATCTCGATAACTCAAAAAATA

CGCCCGGTAGTGATCTTATTTCATTATGGTGAAAGTTGGAACCTCTTACG

TGCCGATCAACGTCTCATTTTCGCCAGATATCGACGTCTAAGAAACCATT

ATTATCATGACATTAACCTATAAAAATAGGCGTATCACGAGGCCCTTTCG

TCTTCAC
```

For some embodiments, the native CsgBAC promoter was cloned into pZS32-CsgA at XhoI and KpnI sites using the following primers:

```
pF_promoter:
                                          (SEQ ID NO: 8)
5'-GACTCGAGCAGAAGTACTGACAGATGTTGC-3'
TmNN: 65/53 (aycP1)

pR_promoter:
                                          (SEQ ID NO: 9)
5'-CTGGTACCTTTCTCCTCTTTAATTGTCACCCTGGACCTGG-3'
TmNN: 67/49 (aycP3)
```

The sequence of pZS32-CsgA, containing a native CsgA promoter is as follows (SEQ ID NO:10):

```
CTCGAGCAGAAGTACTGACAGATGTTGCACTGCTGTGTGTAGTAATAAAT

CAGCCCTAAATGGGTAAAATATAAAACTAATGGATTACATCTGATTTCAA

TCTAGCCATTACAAATCTTAAATCAAGTGTTAAACATGTAACTAAATGTA

ACTCGTTATATTAAAATGTTAACCTTAAGGTTTTATTAAGTTTAGAAATG

ATAGAAAAGTTGTACATTTGGTTTTTATTGCACAATTTTAAAAAATCATA

CAAATGGTGATAACTTACTAATAATGCATATAAAAAATATTTCGGTGTAG

TCCTTTCGTCATGTAAAACGTTCTTGTTTTTTCTCCACACCTCCGTGGAC

AATTTTTTACTGCAAAAAGACGAGGTTTGTCACGGCTTGTGCGCAAGACA

TATCGCAGCAATCAGCGACGGGCAAGAAGAATGACTGTCTGGTGCTTTTT

GATAGCGGAAAACGGAGATTTAAAAGAAAACAAAATATTTTTTTGCGTAG

ATAACAGCGTATTTACGTGGGTTTTAATACTTTGGTATGAACTAAAAAAG

AAAAATACAACGCGCGGGTGAGTTATTAAAAATATTTCCGCAGACATACT

TTCCATCGTAACGCAGCGTTAACAAAATACAGGTTGCGTTAACAACCAAG

TTGAAATGATTTAATTTCTTAAATGTACGACCAGGTCCAGGGTGACAATT

AAAGAGGAGAAAGGTACCATGAAACTTTTAAAAGTAGCAGCAATTGCAGC

AATCGTATTCTCCGGTAGCGCTCTGGCAGGTGTTGTTCCTCAGTACGGCG

GCGGCGGTAACCACGGTGGTGGCGGTAATAATAGCGGCCCAAATTCTGAG

CTGAACATTTACCAGTACGGTGGCGGTAACTCTGCACTTGCTCTGCAAAC

TGATGCCCGTAACTCTGACTTGACTATTACCCAGCATGGCGGCGGTAATG

GTGCAGATGTTGGTCAGGGCTCAGATGACAGCTCAATCGATCTGACCCAA

CGTGGCTTCGGTAACAGCGCTACTCTTGATCAGTGGAACGGCAAAAATTC

TGAAATGACGGTTAAACAGTTCGGTGGTGGCAACGGTGCTGCAGTTGACC

AGACTGCATCTAACTCCTCCGTCAACGTGACTCAGGTTGGCTTTGGTAAC

AACGCGACCGCTCATCAGTACTAATACATCACGCGTGGCATCAAATAAAA

CGAAAGGCTCAGTCGAAAGACTGGGCCTTTCGTTTTATCTGTTGTTTGTC

GGTGAACGCTCTCCTGAGTAGGACAAATCCGCCGCCCTAGACCTAGGGTA

CGGGTTTTGCTGCCCGCAAACGGGCTGTTCTGGTGTTGCTAGTTTGTTAT

CAGAATCGCAGATCCGGCTTCAGGTTTGCCGGCTGAAAGCGCTATTTCTT

CCAGAATTGCCATGATTTTTTCCCCACGGGAGGCGTCACTGGCTCCCGTG

TTGTCGGCAGCTTTGATTCGATAAGCAGCATCGCCTGTTTCAGGCTGTCT

ATGTGTGACTGTTGAGCTGTAACAAGTTGTCTCAGGTGTTCAATTTCATG

TTCTAGTTGCTTTGTTTTACTGGTTTCACCTGTTCTATTAGGTGTTACAT

GCTGTTCATCTGTTACATTGTCGATCTGTTCATGGTGAACAGCTTTAAAT

GCACCAAAAACTCGTAAAAGCTCTGATGTATCTATCTTTTTTTACACCGTT

TTCATCTGTGCATATGGACAGTTTTCCCTTTGATATCTAACGGTGAACAG

TTGTTCTACTTTTGTTTGTTAGTCTTGATGCTTCACTGATAGATACAAGA

GCCATAAGAACCTCAGATCCTTCCGTATTTAGCCAGTATGTTCTCTAGTG

TGGTTCGTTGTTTTTGCGTGAGCCATGAGAACGAACCATTGAGATCATGC

TTACTTTGCATGTCACTCAAAAATTTTGCCTCAAAACTGGTGAGCTGAAT

TTTTGCAGTTAAAGCATCGTGTAGTGTTTTTCTTAGTCCGTTACGTAGGT

AGGAATCTGATGTAATGGTTGTTGGTATTTTGTCACCATTCATTTTTATC

TGGTTGTTCTCAAGTTCGGTTACGAGATCCATTTGTCTATCTAGTTCAAC

TTGGAAAATCAACGTATCAGTCGGGCGGCCTCGCTTATCAACCACCAATT

TCATATTGCTGTAAGTGTTTAAATCTTTACTTATTGGTTTCAAAACCCAT

TGGTTAAGCCTTTTAAACTCATGGTAGTTATTTTCAAGCATTAACATGAA

CTTAAATTCATCAAGGCTAATCTCTATATTTGCCTTGTGAGTTTTCTTTT

GTGTTAGTTCTTTTAATAACCACTCATAAATCCTCATAGAGTATTTGTTT

TCAAAAGACTTAACATGTTCCAGATTATATTTTATGAATTTTTTTAACTG

GAAAAGATAAGGCAATATCTCTTCACTAAAAACTAATTCTAATTTTTCGC

TTGAGAACTTGGCATAGTTTGTCCACTGGAAAATCTCAAAGCCTTTAACC

AAAGGATTCCTGATTTCCACAGTTCTCGTCATCAGCTCTCTGGTTGCTTT

AGCTAATACACCATAAGCATTTTCCCTACTGATGTTCATCATCTGAGCGT

ATTGGTTATAAGTGAACGATACCGTCCGTTCTTTCCTTGTAGGGTTTTCA

ATCGTGGGGTTGAGTAGTGCCACACAGCATAAAATTAGCTTGGTTTCATG

CTCCGTTAAGTCATAGCGACTAATCGCTAGTTCATTTGCTTTGAAAACAA

CTAATTCAGACATACATCTCAATTGGTCTAGGTGATTTTAATCACTATAC

CAATTGAGATGGGCTAGTCAATGATAATTACTAGTCCTTTTCCTTTGAGT

TGTGGGTATCTGTAAATTCTGCTAGACCTTTGCTGGAAAACTTGTAAATT

CTGCTAGACCCTCTGTAAATTCCGCTAGACCTTTGTGTGTTTTTTTGTT

TATATTCAAGTGGTTATAATTTATAGAATAAAGAAAGAATAAAAAAAGAT

AAAAAGAATAGATCCCAGCCCTGTGTATAACTCACTACTTTAGTCAGTTC

CGCAGTATTACAAAAGGATGTCGCAAACGCTGTTTGCTCCTCTACAAAAC

AGACCTTAAAACCCTAAAGGCTTAAGTAGCACCCTCGCAAGCTCGGGCAA

ATCGCTGAATATTCCTTTTGTCTCCGACCATCAGGCACCTGAGTCGCTGT
```

-continued

CTTTTTCGTGACATTCAGTTCGCTGCGCTCACGGCTCTGGCAGTGAATGG

GGGTAAATGGCACTACAGGCGCCTTTTATGGATTCATGCAAGGAAACTAC

CCATAATACAAGAAAAGCCCGTCACGGGCTTCTCAGGGCGTTTTATGGCG

GGTCTGCTATGTGGTGCTATCTGACTTTTTGCTGTTCAGCAGTTCCTGCC

CTCTGATTTTCCAGTCTGACCACTTCGGATTATCCCGTGACAGGTCATTC

AGACTGGCTAATGCACCCAGTAAGGCAGCGGTATCATCAACAGGCTTACC

CGTCTTACTGTCCCTAGTGCTTGGATTCTCACCAATAAAAAACGCCCGGC

GGCAACCGAGCGTTCTGAACAAATCCAGATGGAGTTCTGAGGTCATTACT

GGATCTATCAACAGGAGTCCAAGCGAGCTCGATATCAAATTACGCCCGC

CCTGCCACTCATCGCAGTACTGTTGTAATTCATTAAGCATTCTGCCGACA

TGGAAGCCATCACAGACGGCATGATGAACCTGAATCGCCAGCGGCATCAG

CACCTTGTCGCCTTGCGTATAATATTTGCCCATGGTGAAAACGGGGCGA

AGAAGTTGTCCATATTGGCCACGTTTAAATCAAAACTGGTGAAACTCACC

CAGGGATTGGCTGAGACGAAAAACATATTCTCAATAAACCCTTTAGGGAA

ATAGGCCAGGTTTTCACCGTAACACGCCACATCTTGCGAATATATGTGTA

GAAACTGCCGGAAATCGTCGTGGTATTCACTCCAGAGCGATGAAAACGTT

TCAGTTTGCTCATGGAAAACGGTGTAACAAGGGTGAACACTATCCCATAT

CACCAGCTCACCGTCTTTCATTGCCATACGGAATTCCGGATGAGCATTCA

TCAGGCGGGCAAGAATGTGAATAAAGGCCGGATAAAACTTGTGCTTATTT

TTCTTTACGGTCTTTAAAAAGGCCGTAATATCCAGCTGAACGGTCTGGTT

ATAGGTACATTGAGCAACTGACTGAAATGCCTCAAAATGTTCTTTACGAT

GCCATTGGGATATATCAACGGTGGTATATCCAGTGATTTTTTCTCCATT

TTAGCTTCCTTAGCTCCTGAAAATCTCGATAACTCAAAAAATACGCCCGG

TAGTGATCTTATTTCATTATGGTGAAAGTTGGAACCTCTTACGTGCCGAT

CAACGTCTCATTTTCGCCAGATATCGACGTCTAAGAAACCATTATTATCA

TGACATTAACCTATAAAAATAGGCGTATCACGAGGCCCTTTCGTCTTCAC

Peptide Fusions

ZnS Binding Peptide

The ZnS binding peptide, A7, is described in Mao et al., (2004) *Science* 303:213 and consists of the sequence: CNNPMHQNC (SEQ ID NO:2). The linker sequence GGGS was attached to the ZnS binding peptide, generating the sequence: GGGSCNNPMHQNC (SEQ ID NO:11), which was fused to the C-terminus of CsgA.

The DNA sequence of the C-terminal region of CsgA, linker and the ZnS binding peptide was as follows:

(SEQ ID NO: 12)
GCGACCGCTCATCAGTACGGTGGTGGTTCTTGCAACAACCCGATGCACC

AGAACTGC.

The reverse complement, containing an MluI site is shown as follows:

(SEQ ID NO: 13)
GATACGCGTTTAGCAGTTCTGGTGCATCGGGTTGTTGCAAGAACCACCAC

CGTACTGATGAGCGGTCGC.

Sequential PCR using standard conditions was used to clone the ZnS binding peptide at the C-terminus of CsgA.

The forward primer was: aycP41 (D1283) TmNN 66/52; 5' aycP41 (D1283) TmNN 66/52;
(SEQ ID NO: 34)
5' AAAGAGGAGAAAGGTACCATGAAACTTTTAAAAGTAGCAGCA 3'.

The three reverse primers were:

1) aycP15:
(SEQ ID NO: 123)
5'-GTTGTTGCAAGAACCACCACCGTACTGATGAGCGGTCGC-3'
TmNN: 70/52;

2) aycP16:
(SEQ ID NO: 14)
5'-GTTCTGGTGCATCGGGTTGTTGCAAGAACCACCAC-3'
TmNN: 67/50;

3) aycP17:
(SEQ ID NO: 15)
5'-GATACGCGTTTAGCAGTTCTGGTGCATCGGGTTGTT-3'
TmNN: 68/54;

CdS Binding Peptide

The CdS binding peptide, J140, is described in Mao et al., (2004) *Science* 303:213 and consists of the sequence: SLTPLTTSHLRS (SEQ ID NO:3). The linker sequence GGGS was attached to the CdS binding peptide generating the sequence: GGGSSLTPLTTSHLRS (SEQ ID NO:16), which was fused to the C-terminus of CsgA.

The DNA sequence of the C-terminal region of CsgA, the linker and the CdS binding peptide was as follows:

(SEQ ID NO: 17)
GCGACCGCTCATCAGTACGGTGGTGGTTCTTCTCTGACCCCGCTGACCAC

CTCTCACCTGCGTTCT.

The reverse complement, containing a stop codon and MluI site is shown as follows:

(SEQ ID NO: 18)
GATACGCGTTTAAGAACGCAGGTGAGAGGTGGTCAGCGGGGTCAGAGAAG

AACCACCACCGTACTGATGAGCGGTCGC.

The sequence was reconstructed to generate the following sequence: GATACGCGT (SEQ ID NO: 19)
GATACGCGTTTAAGAACGCAGGTGAGAGGTGGTCAACGGGGTCAGAGA

AGAACCACCACCGTACTGATGAGCGGTCGC.

Sequential PCR using standard conditions was used to clone the CdS binding peptide at the C-terminus of CsgA.

The forward primer was: aycP41 (D1283) TmNN 66/52; 5' aycP41 (D1283) TmNN 66/52;
(SEQ ID NO: 34)
5' AAAGAGGAGAAAGGTACCATGAAACTTTTAAAAGTAGC

AGCA 3'.

The four reverse primers were:

1) aycP18:
(SEQ ID NO: 20)
5'-AGAAGAACCACCACCGTACTGATGAGCGGTCGC-3'
TmNN: 68/52;

2) aycP19:
(SEQ ID NO: 21)
5'-GGTCAACGGGGTCAGAGAAGAACCACCACCGTACT-3'
TmNN: 67/51;

3) aycP20:
(SEQ ID NO: 22)
5'-ACGCAGGTGAGAGGTGGTCAACGGGGTCAGAGAAGA-3'
TmNN: 70/55;

4) aycP21:
(SEQ ID NO: 23)
5'-GATACGCGTTTAAGAACGCAGGTGAGAGGTGGT C-3'
TmNN: 67/54;

Au Binding Peptide

The Au binding peptide LKAHLPPSRLPS (SEQ ID NO:1) is described in Nam et al., (2006) *Science* 312:885, wherein it was isolated by screening against a gold substrate with a phage display library. The linker sequence GGGS was attached to the gold binding peptide generating the sequence: GGGSLKAHLPPSRLPS (SEQ ID NO:24), which was fused to the C-terminus of CsgA.

The DNA sequence of the C-terminal region of CsgA, the linker and the Au binding peptide was as follows:

(SEQ ID NO: 25)
GCGACCGCTCATCAGTACGGTGGTGGTTCTCTGAAAGCTCACCTGCCGCC

GTCTCGTCTGCCGTCT.

The reverse complement, containing a stop codon and MluI site is shown as follows:

(SEQ ID NO: 26)
GATACGCGTTTAAGACGGCAGACGAGACGGCGGCAGGTGAGCTTTCAGAG

AACCACCACCGTACTGATGAGCGGTCGC.

Sequential PCR using standard conditions was used to clone the gold binding peptide at the C-terminus of CsgA. The forward primer was:

aycP41 (D1283) TmNN 66/52;
(SEQ ID NO: 34)
5' AAAGAGGAGAAAGGTACCATGAAACTTTTAAAAGTAGC

AGCA 3'.

The three reverse primers were:

1) aycP22:
(SEQ ID NO: 27)
5' GAGCTTTCAGAGAACCACCACC GTACTGATGAGCGGTCGC 3'
TmNN 72/52

2) aycP23:
(SEQ ID NO: 28)
5' CAGACGAGACGGCGGCAGGTGAGCTTTCAGAGAACCACCA 3'
TmNN 74/52

3) aycP24:
(SEQ ID NO: 29)
5' GATACGCGTTTAAGACGGCAGACGAGACGGCGG 3' TmNN 70/51

Fe₃O₄ Binding Peptide

The Fe₃O₄ binding peptide, FO7, corresponding to the sequence CDSPHRHSC (SEQ ID NO:30), is described in "Evolving Biomolecular Control and Peptide Specificity for the Synthesis and Assembly of II-VI Semiconductor Nanomaterials," PhD Thesis Dissertation by Christine Elizabeth Flynn, 2003, University of Texas at Austin, page 81.

The linker sequence GGGS was attached to the Fe₃O₄ binding peptide, generating the sequence: GGGSCDSPHRHSC (SEQ ID NO:31), which was fused to the C-terminus of CsgA.

The DNA sequence of the C-terminal region of CsgA, the linker and the Fe₃O₄ binding peptide was as follows:

(SEQ ID NO: 32)
GCGACCGCTCATCAGTAC GGTGGTGGATCC

TGCGACTCTCCGCACCGTCACTCTTGC.

The reverse complement, containing a stop codon and MluI site is shown as follows:

(SEQ ID NO: 33)
GATACGCGTTTAGCAAGAGTGACGGTGCGGAGAGTCGCA

GGATCCACCACCGTACTGATGAGCGGTCGC.

The forward primer was:

aycP41 (D1283) TmNN 66/52;
(SEQ ID NO: 34)
5' AAAGAGGAGAAAGGTACCATGAAACTTTTAAAAGTAGC AGCA 3'.

The three reverse primers were:

1) aycP48:
(SEQ ID NO: 35)
5'-TCGCAGGATCCACCACC GTACTGATGAGCGGTCGC-3'
TmNN 71/52

2) aycP49:
(SEQ ID NO: 36)
5'-TGACGGTGCGGAGAGTCGCAGGATCCACCACC-3'
TmNN 70/51

3) aycP50:
(SEQ ID NO: 37)
5'-GATACGCGTTTAGCAAGAGTGACGGTGCGGAGAGT-3'
TmNN 69/50.

FePt Binding Peptide

The FePt binding peptide, FP12, is described in Mao et al., (2004) *Science* 303:213 and consists of the sequence: HNKHLPSTQPLA (SEQ ID NO:38). The linker sequence GGGS was attached to the FePt binding peptide generating the sequence: GGGSHNKHLPSTQPLA (SEQ ID NO:39), which was fused to the C-terminus of CsgA.

The DNA sequence of the C-terminal region of CsgA, the linker and the FePt binding peptide was as follows:

(SEQ ID NO: 40)
GCGACCGCTCATCAGTAC GGTGGTGGATCC

CACAACAAACACCTGCCGTCTACCCAGCCGCTGGCT.

The reverse complement, containing a stop codon and MluI site is shown as follows:

(SEQ ID NO: 41)
GATACGCGTTTAAGCCAGCGGCTGGGTAGACGGCAGGTGTTTGTTGTG

GGATCCACCACCGTACTGATGAGCGGTCGC.

Sequential PCR using standard conditions was used to clone the FePt peptide at the C-terminus of CsgA.

The forward primer was:
aycP41 (D1283) TmNN 66/52; 5' aycP41 (D1283) TmNN 66/52;
(SEQ ID NO: 34)
5' AAAGAGGAGAAAGGTACCATGAAACTTTTAAAAGTAGC AGCA 3'.

The three reverse primers were:

1) aycP42 TmNN: 70/52;
(SEQ ID NO:42)
5'-TTGTTGTG GGATCCACCACCGTACTGATGAGCGGTCGC-3'

2) aycP43 TmNN: 69/51;
(SEQ ID NO: 43)
5'-TGGGTAGACGGCAGGTGTTTGTTGTGGGATCCACCACC-3'

3) aycP44 TmNN: 73/51;
(SEQ ID NO: 44)
5'-GATACGCGTTTAAGCCAGCGGCTGGGTAGACGGCAGGT-3'

CoPt Binding Peptide

The CoPt binding peptide, CP7, is described in Mao et al., (2004) *Science* 303:213 and consists of the sequence: CNAGDHANC (SEQ ID NO:45). The linker sequence GGGS was attached to the CoPt binding peptide generating the sequence: GGGSCNAGDHANC (SEQ ID NO:46), which was fused to the C-terminus of CsgA.

The DNA sequence of the C-terminal region of CsgA, the linker and the CoPt binding peptide was as follows:

(SEQ ID NO: 47)
GCGACCGCTCATCAGTAC GGTGGTGGATCC

TGCAACGCTGGTGACCACGCTAACTGC.

The reverse complement, containing a stop codon and MluI site is shown as follows:

(SEQ ID NO: 48)
GATACGCGTTTAGCAGTTAGCGTGGTCACCAGCGTTGCA

GGATCCACCACCGTACTGATGAGCGGTCGC.

Sequential PCR using standard conditions was used to clone the CoPt peptide at the C-terminus of CsgA.

The forward primer was:

aycP41 (D1283) TmNN 66/52;
(SEQ ID NO: 34)
5' AAAGAGGAGAAAGGTACCATGAAACTTTTAAAAGTAGC AGCA 3'.

The reverse primers were:

1) aycP45 TmNN;70/52;
(SEQ ID NO: 49)
5'-TTGCAGGATCCACCACCGTACTGATGAGCGGTCGC-3'

2) aycP46 TmNN;71/54;
(SEQ ID NO: 50)
5'-GCGTGGTCACCAGCGTTGCAGGATCCACCACCGT-3'

3) aycP47 TmNN:70/52;
(SEQ ID NO: 51)
5'-GATACGCGTTTAGCAGTTAGCGTGGTCACCAGCGT-3'

FLAG Tag Fusion

A FLAG tag was fused to the C-terminus of CsgA using sequential PCR under standard conditions.

The forward primer was:

aycP41 (D1283) TmNN 66/52;
(SEQ ID NO: 34)
5' AAAGAGGAGAAAGGTACCATGAAACTTTTAAAAGTAGC AGCA 3'.

The two reverse primers were:

1) D1289:
(SEQ ID NO: 52)
5' TCGTCGTCATCCTTGTAGTCGTACTGATGAGCGGTCGC 3'
TmNN 71/52 part-FLAG(r)-CsgA-r (D1289)

(SEQ ID NO: 53)
2) D1290:
5' GATACGCGTTTACTTGTCGTCGTCATCCTTGTAGTC 3'
TmNN 66/52 MluI-FLAG(r)-r (D1290)

6×His Fusion

A 6 histidine (His) tag (HHHHHH) (SEQ ID NO:54) was fused at the C terminus of CsgA. The linker GGGS was fused to the 6×His tag, generating the sequence:

(SEQ ID NO: 55)
GGGSHHHHHH.

The DNA sequence of the C-terminal region of CsgA, the linker and the His tag was as follows:

(SEQ ID NO: 56)
GCGACCGCTCATCAGTAC GGTGGTGGATCCCATCATCACCATCACCAC.

The reverse complement, containing a stop codon and MluI site is shown as follows:

(SEQ ID NO: 57)
GATACGCGTTTAGTGGTGATGGTGATGATGGGATCCACCACCGTACTGAT

GAGCGGTCGC.

Sequential PCR using standard conditions was used to clone the 6×His tag at the C-terminus of CsgA.

The forward primer was:

aycP41 (D1283) TmNN 66/52;
(SEQ ID NO: 34)
5'AAAGAGGAGAAAGGTACCATGAAACTTTTAAAAGTAGCAGCA 3'

The reverse primers were:

1) aycP51:
(SEQ ID NO: 58)
5'-GGTGATGATG GGATCCACCACC GTACTGATGAGCGGTCGC-3'
TmNN: 71/52

2) aycP52:
(SEQ ID NO: 59)
5'-GATACGCGTTTAGTGGTGATGGTGATGATGGGATCCACC-3'
TmNN: 67/50

Example 5

Interfacing Curli Fibers with General-Purpose Affinity Groups

It is also useful to engineer curli fibers that bind general-purpose affinity groups, which allow the fibers to bind many entities, including metal nanoparticles (nanoprobes.com/products/NTAgold.html), semiconductor quantum dots (Park et al. (2010) Langmuir 26:7327), enzymes (qiagen.com/products/protein/detection/qiaexpressdetectionsystem/ni-ntahrpconjugate.aspx), and even molecular motors (qiagen.com/literature/qiagennews/0398/983ninta.pdf). To do so, 7xHis tag sequences were inserted into the peptide sequence of CsgA. These sequences bind to nickel NTA (NiNTA) groups with high affinity and also high specificity provided the binding environment is acceptable.

Figure 30:
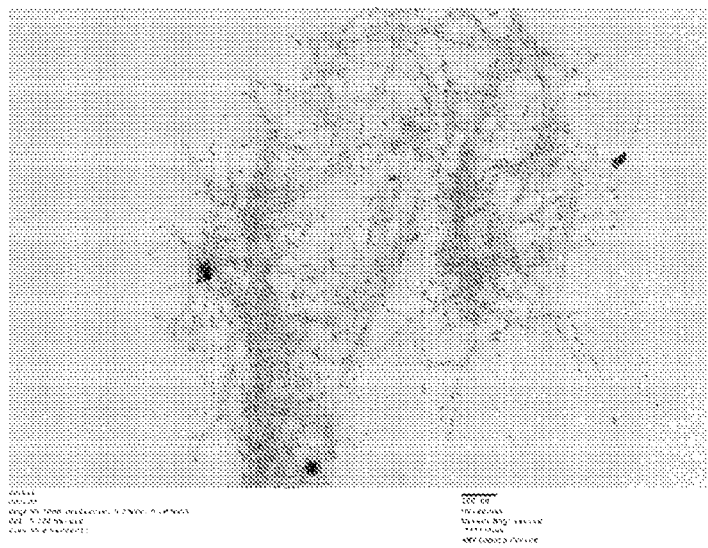
FIG. 30 presents wildtype unmodified curli fibers which still do not bind NiNTA-conjugated gold nanoparticles in a binding buffer consisting of 0.5M NaCl, 10 mM imidazole and 0.2 v/v % Tween 20.

The binding between a specific histidine tag-NiNTA interaction is also influenced by the protein which displays the histidine tag, so in some embodiments, it is preferable to optimize the buffer in which the binding interactions are carried out. In some embodiments, it was found that PBS buffer with 0.5M NaCl, 100 mM imidazole and 0.2 v/v % Tween 20 allowed specific interaction, and using this binding buffer condition with several wash steps allowed NiNTA conjugated gold particles to bind and be organized into arrays on curli fibers that display histidine tags (FIG. 29A), but not bind curli fibers without the tag (FIG. 29B). In contrast, in non-optimal binding conditions, unmodified curli fibers also did not bind NiNTA-conjugated gold nanoparticles (FIG. 30).

Example 6

Insertion of 7xHis Throughout the CsgA Protein

To further demonstrate insertion of polypeptides into the CsgA protein sequence and to investigate effectiveness of insertion into different regions of the protein, 7xHis tags were inserted in a variety of locations throughout CsgA. Electron microscopy was then used to determine whether gold nanoparticles fused to NiNTA could bind to CsgA.

The DNA sequence of the 7xHis tag was CACCATCAC-CATCACCACCAT (SEQ ID NO:60) and the protein sequence was HHHHHHH (SEQ ID NO:61). The reverse complement DNA sequence is as follows:

(SEQ ID NO: 62)
ATGGTGGTGATGGTGATGGTG.

Figure 19:
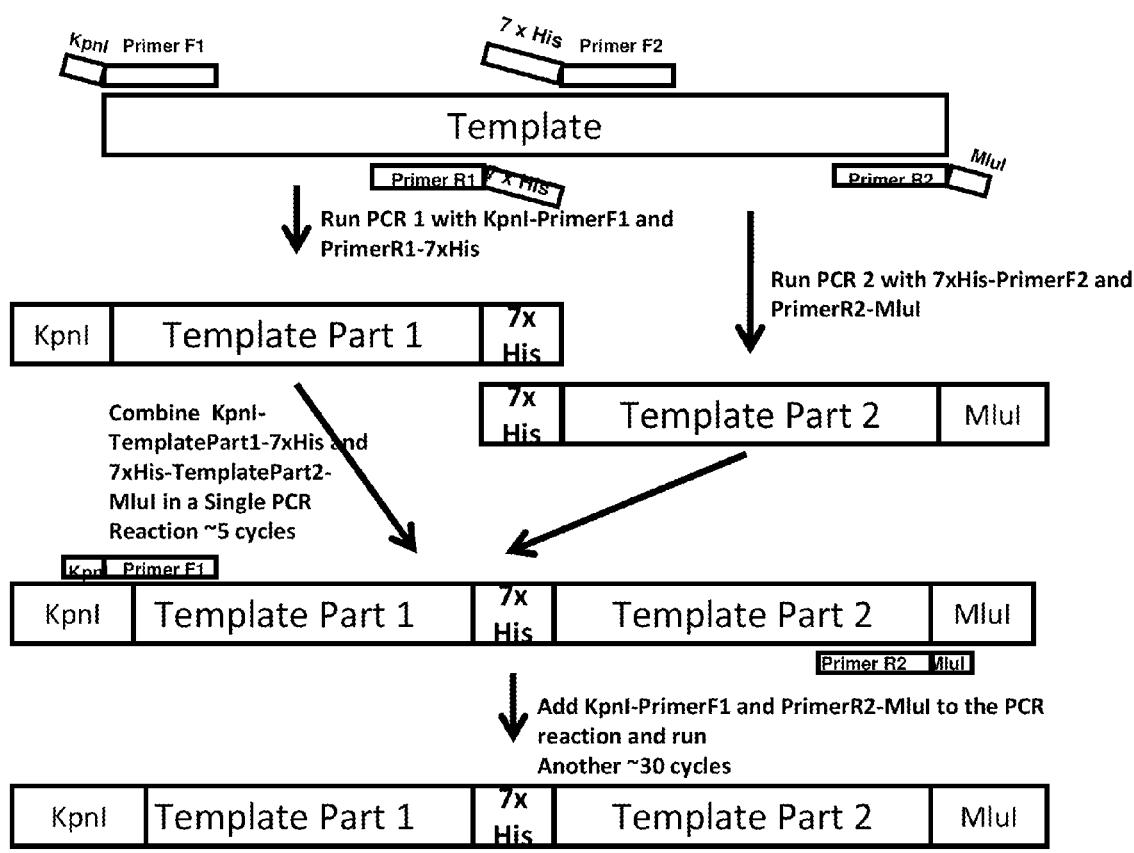
FIG. 19 presents a schematic depicting the PCR-based approach to introducing 7xHis tags throughout the CsgA protein. In the diagram, the primers are shown as having the complete 7xHis sequence, however, that is not necessary as long as the overlapping and extension steps yield 7xHis (e.g., the overlap between Primer R1-7xHis and 7xHis-Primer F2 will yield the full 7xHis tag upon PCR).

The PCR-based approach for insertion of 7xHis tags throughout CsgA is shown in FIG. 19. A summary of the primers used for 7xHis insertion is shown in FIG. 20. A schematic of the structure of CsgA is shown in FIG. 6C.

The CsgA protein comprises multiple different regions. In the below DNA sequence, each row of the sequence represents one region of the protein. The first two lines correspond to regions involved in secretion. The next 5 correspond to the R domains of the protein (R1-R5). The large breaks within the sequence represent places where 7xHis tags were inserted. The seven rows of DNA sequences correspond to SEQ ID NOs 63-69.

```
ATGAAACTTT TAAAAGTAGC AGCAATTGCA GCAATCGTAT

TCTCCGGTAG CGCTCTGGCA GGTGTTGTTC CTCAGTACGG

CGGCGGCGGT AACCACGGTG GTGGCGGTAA TAATAGCGGC

CCAAAT TCTG AGCTGAACAT TTACCAGTAC GGTGGC

GGTA ACTCTGCACT TGCTCTGCAA ACTGAT GCCCGTAAC

TCTGA CTTGACTATT ACCCAGCATG GCGGC GGTAA

TGGTGCAGAT GTTGGTCAGG GCTCA GATGAC

AGCTCAATC GATCTGACCC AACGTGGCTT C GGTAACAGC

GCTACTCTTG ATCAGTGGAA C GGCAAAAAT TCTGAAATGA

CGGTTAAACA GTTCGGTGGT GGCAACGGTG CTGCAGTTGA

CCAGACTGCA TCTAAC TCCT CCGTCAACGT GACTCAGGTT

GGCTTT GGTA ACAACGCGAC CGCTCATCAG TACTAA
```

The corresponding seven rows of protein sequences (Sec (signal sequence)-N22-R1-R2-R3-R4-R5)) are provided below and are represented by SEQ ID NOs 70-76.

```
MKLLKVAAIAAIVFSGSALA

GVVPQYGGGGNHGGGGNNSGPN

SELNIYQYGG GNSALALQTD ARN

SDLTITQHGG GNGADVGQGS DD

SSIDLTQRGF GNSATLDQWN GKN

SEMTVKQFGG GNGAAVDQTA SN

SSVNVTQVGF GNNATAHQY
```

Primers used for subcloning and verification were as follows:

Insertion of 7xHis Between R1 and R2

```
TmNN 68/51 part7xHis-CsgA(63)-f(D1363)
                                 (SEQ ID NO: 77)
5' ACCATCACCATCACCACCATGCCCGTAACTCTGACTTGA 3'

TmNN 69/50 part7xHis-CsgA(62)-r(D1364)
                                 (SEQ ID NO: 78)
5' TGGTGGTGATGGTGATGGTGATCAGTTTGCAGAGCAAGT 3'

5aFIq' R17 + R1642 #1
                                 (SEQ ID NO: 79)
MKLLKVAAIAAIVFSGSALAGVVPQYGGGGNHGGGGNNSGPNSEL

NIYQYGGGNSALALQTDHHHHHHHARNSDLTITQHGGGNGADVGQ

GSDDSSIDLTQRGFGNSATLDQWNGKNSEMTVKQFGGGNGAAVDQ

TASNSSVNVTQVGFGNNATAHQY*
```

Insertion of 7×His Between R2 and R3

```
TmNN 69/51 part7xHis-CsgA(86)-f(D1365)
                                      (SEQ ID NO: 80)
5' ACCATCACCATCACCACCATGATGACAGCTCAATCGATCT 3'

TmNN 68/50 part7xHis-CsgA(85)-r(D1366)
                                      (SEQ ID NO: 81)
5' TGGTGGTGATGGTGATGGTGTGAGCCCTGACCAACATC 3'
```

5aFIq' R17+R1643 #1

```
                                              (SEQ ID NO: 82)
MKLLKVAAIAAIVFSGSALAGVVPQYGGGGNHGGGGNNSGPNSEL
NIYQYGGGNSALALQTDARNSDLTITQHGGGNGADVGQGSHHHHH
HHDDSSIDLTQRGFGNSATLDQWNGKNSEMTVKQFGGGNGAAVDQ
TASNSSVNVTQVGFGNNATAHQY*
```

Insertion of 7×His Between R3 and R4

```
TmNN 67/50 part7xHis-CsgA(108)-f(D1367)
                                      (SEQ ID NO: 83)
5' ACCATCACCATCACCACCATGGCAAAAATTCTGAAATGACG 3'

TmNN 69/51 part7xHis-CsgA(107)-r(D1368)
                                      (SEQ ID NO: 84)
5' TGGTGGTGATGGTGATGGTGGTTCCACTGATCAAGAGTAGC 3'
```

5aFIq' R17+R1644 #1

```
                                              (SEQ ID NO: 85)
MKLLKVAAIAAIVFSGSALAGVVPQYGGGGNHGGGGNNSGPNSEL
NIYQYGGGNSALALQTDARNSDLTITQHGGGNGADVGQGSDDSSI
DLTQRGFGNSATLDQWNHHHHHHHGKNSEMTVKQFGGGNGAAVDQ
TASNSSVNVTQVGFGNNATAHQY*
```

Insertion of 7×His Between R4 and R5

```
TmNN 68/51 part7xHis-CsgA(131)-f(D1369)
                                      (SEQ ID NO: 86)
5' ACCATCACCATCACCACCATTCTAACTCCTCCGTCAACG 3'

TmNN 69/51 part7xHis-CsgA(130)-r(D1370)
                                      (SEQ ID NO: 87)
5' TGGTGGTGATGGTGATGGTGTGCAGTCTGG TCAACTGC 3'
```

5aFIq' R17+R1645 #1

```
                                              (SEQ ID NO: 88)
MKLLKVAAIAAIVFSGSALAGVVPQYGGGGNHGGGGNNSGPNSEL
NIYQYGGGNSALALQTDARNSDLTITQHGGGNGADVGQGSDDSSI
DLTQRGFGNSATLDQWNGKNSEMTVKQFGGGNGAAVDQTAHHHHH
HHSNSSVNVTQVGFGNNATAHQY*
```

Insertion of 7×His within R1

```
TmNN 68/50 part7xHis-CsgA(53)-f(D1371)
                                      (SEQ ID NO: 89)
5' ACCATCACCATCACCACCATGGTAACTCTGCACTTGCTC 3'

TmNN 68/51 part7xHis-CsgA(52)-r(D1372)
                                      (SEQ ID NO: 90)
5' TGGTGGTGATGGTGATGGTGGCCACCGTACTGGTAAATGT 3'
```

5aFIq' R17+R1646 #1

```
                                              (SEQ ID NO: 91)
MKLLKVAAIAAIVFSGSALAGVVPQYGGGGNHGGGGNNSGPNSEL
NIYQYGGHHHHHHHGNSALALQTDARNSDLTITQHGGGNGADVGQ
GSDDSSIDLTQRGFGNSATLDQWNGKNSEMTVKQFGGGNGAAVDQ
TASNSSVNVTQVGFGNNATAHQY*
```

Insertion of 7×His within R2

```
TmNN 68/50 part7xHis-CsgA(76)-f(D1373)
                                      (SEQ ID NO: 92)
5' ACCATCACCATCACCACCATGGTAATGGTGCAGATGTTGG 3'

TmNN 71/51 part7xHis-CsgA(75)-r(D1374)
                                      (SEQ ID NO: 93)
5' TGGTGGTGATGGTGATGGTGGCCGCCATGCTGGGT 3'
```

5aFIq' R17+R1647 #1

```
                                              (SEQ ID NO: 94)
MKLLKVAAIAAIVFSGSALAGVVPQYGGGGNHGGGGNNSGPNSEL
NIYQYGGGNSALALQTDARNSDLTITQHGGHHHHHHHGNGADVGQ
GSDDSSIDLTQRGFGNSATLDQWNGKNSEMTVKQFGGGNGAAVDQ
TASNSSVNVTQVGFGNNATAHQY*
```

Insertion of 7×His within R3

```
TmNN 69/51 part7xHis-CsgA(98)-f (D1375)
                                      (SEQ ID NO: 95)
5' ACCATCACCATCACCACCATGGTAACAGCGCTACTCTTG 3'

TmNN 69/51 part7xHis-CsgA(97)-r (D1376)
                                      (SEQ ID NO: 96)
5' TGGTGGTGATGGTGATGGTGGAAGCCACGTTGGGTCAG 3'
```

5aFIq' R17+R1648 #1

```
                                              (SEQ ID NO: 97)
MKLLKVAAIAAIVFSGSALAGVVPQYGGGGNHGGGGNNSGPNSELNIYQ
YGGGNSALALQTDARNSDLTITQHGGGNGADVGQGSDDSSIDLTQRGFH
HHHHHHGNSATLDQWNGKNSEMTVKQFGGGNGAAVDQTASNSSVNVTQV
GFGNNATAHQY*
```

Insertion of 7×His within R4

```
TmNN 69/50 part7xHis-CsgA(121)-f (D1377)
                                      (SEQ ID NO: 98)
5' ACCATCACCATCACCACCATGGCAACGGTGCTGCA 3'

TmNN 68/52 part7xHis-CsgA(120)-r (D1378)
                                      (SEQ ID NO: 99)
5' TGGTGGTGATGGTGATGGTGACCACCGAACTGTTTAACCG 3'
```

5aFIq' R17+R1649 #2

```
                                              (SEQ ID NO: 100)
MKLLKVAAIAAIVFSGSALAGVVPQYGGGGNHGGGGNNSGPNSELNIYQ
YGGGNSALALQTDARNSDLTITQHGGCNGADVGQGSDDSSIDLTQRGFG
```

-continued

NSATLDQWNGKNSEMTVKQFGGHHHHHHHGNGAAVDQTASNSSVNVTQV

GFGNNATAHQY*

Insertion of 7xHis within R5

```
TmNN 69/52 part7xHis-CsgA(143)-f (D1379)
                                      (SEQ ID NO: 101)
5' ACCATCACCATCACCACCATGGTAACAACGCGACCGC 3'

TmNN 69/52 part7xHis-CsgA(142)-r (D1380)
                                      (SEQ ID NO: 102)
5' TGGTGGTGATGGTGATGGTGAAAGCCAACCTGAGTCACG 3'
```

5aFIq' R17+R1650 #1

(SEQ ID NO: 103)
MKLLKVAAIAAIVFSGSALAGVVPQYGGGGNHGGGGNNSGPNSELNIYQ

YGGGNSALALQTDARNSDLTITQHGGGNGADVGQGSDDSSIDLTQRGFG

NSATLDQWNGKNSEMTVKQFGGGNGAAVDQTASNSSVNVTQVGFHHHHH

HHGNNATAHQY*

The Above Primers were Used in Conjunction with the Following Primers:

```
D1283 aycP41 TmNN 66/52
                                      (SEQ ID NO: 34)
5' AAAGAGGAGAAAGGTACCATGAAACTTTTAAAAGTAGCAGCA 3'
same as TmNN 65/53 MluI-CsgA-r (D1284)
                                      (SEQ ID NO: 104)
5' GACAATACGCGTTTAGTACTGATGAGCGGTCG 3'
```

Figure 21:
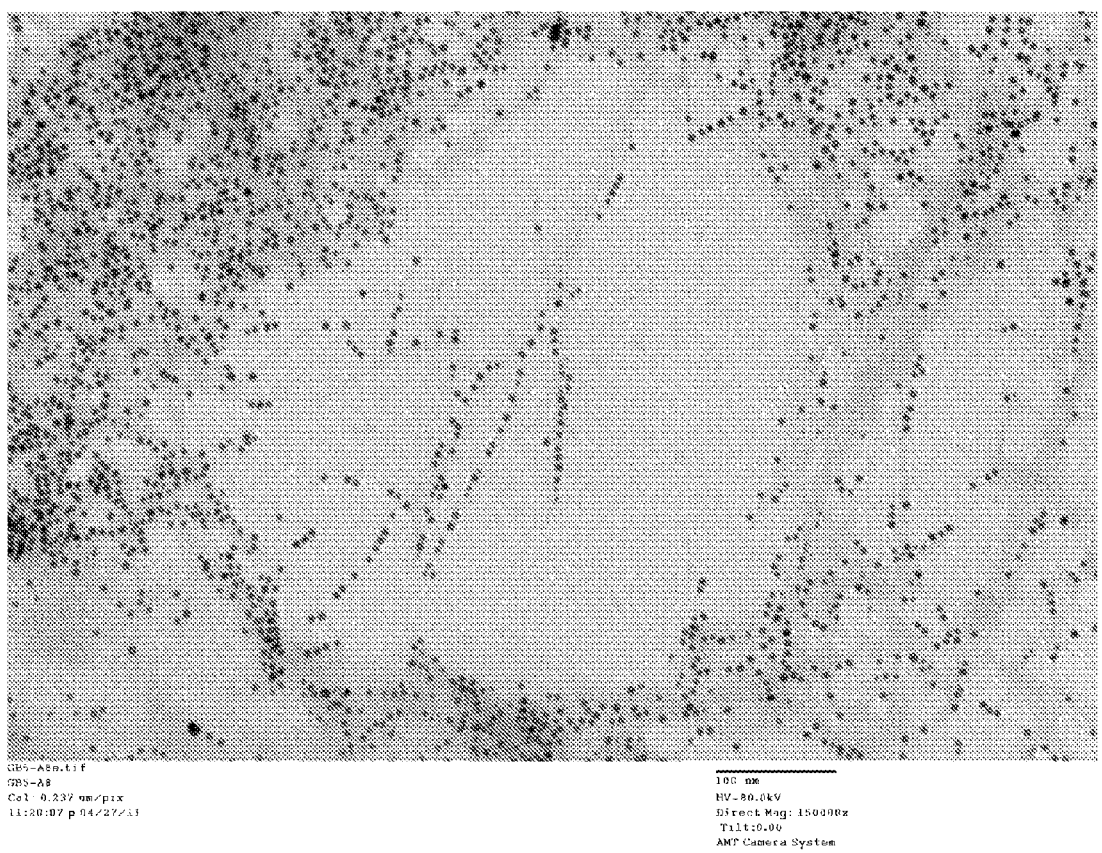
FIG. 21 presents an electron microscopy image showing binding between gold particles fused to Ni-NTA and 7xHis tags inserted in CsgA. In this image, the 7xHis tag was inserted between residues 85 and 86 of CsgA, corresponding to insertion between R2 and R3.
Figure 22:
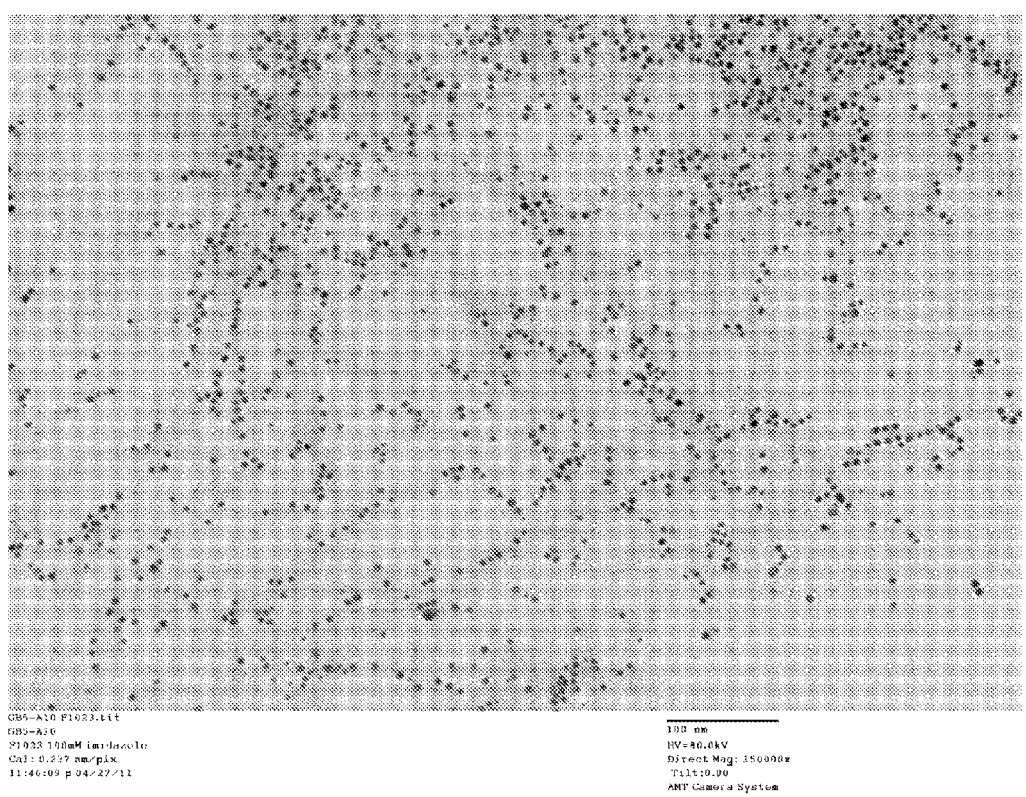
FIG. 22 presents an electron microscopy image showing binding between gold particles fused to Ni-NTA and 7xHis tags inserted in CsgA. In this image, the 7xHis tag was inserted between residues 107 and 108 of CsgA, corresponding to insertion between R3 and R4.
Figure 23:
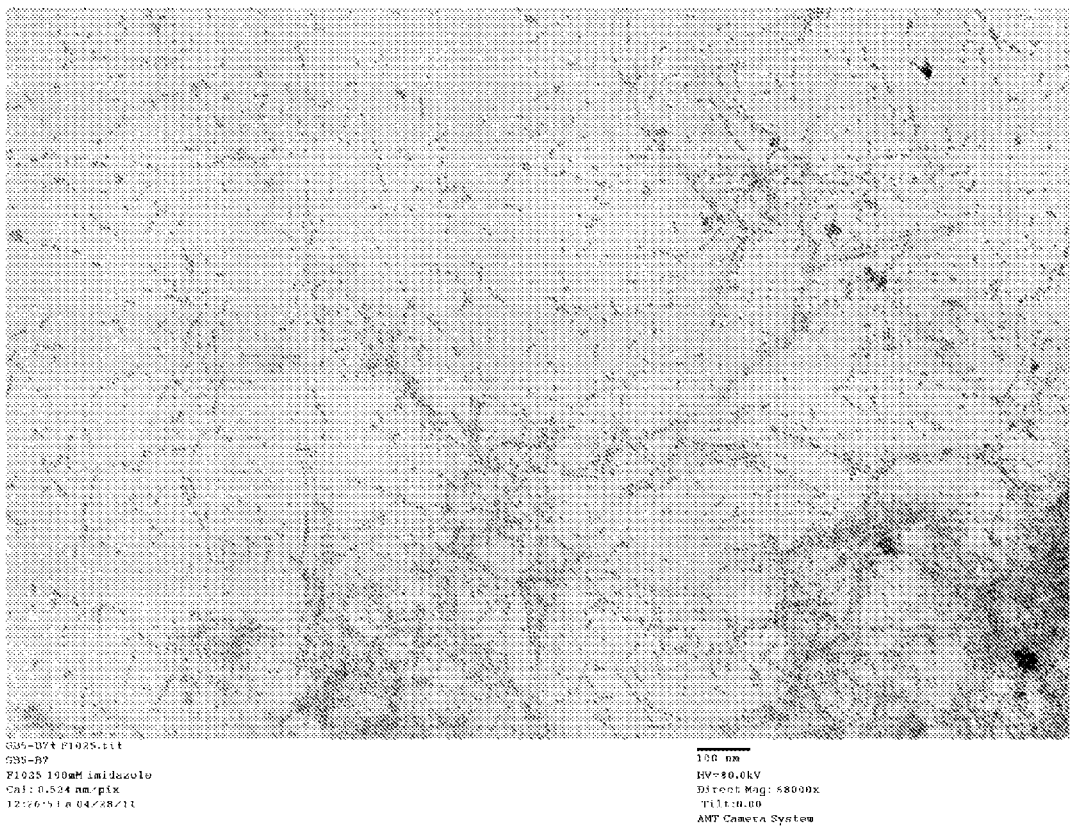
FIG. 23 presents an electron microscopy image showing binding between gold particles fused to Ni-NTA and 7xHis tags inserted in CsgA. In this image, the 7xHis tag was inserted between residues 130 and 131 of CsgA, corresponding to insertion between R4 and R5.
Figure 24:
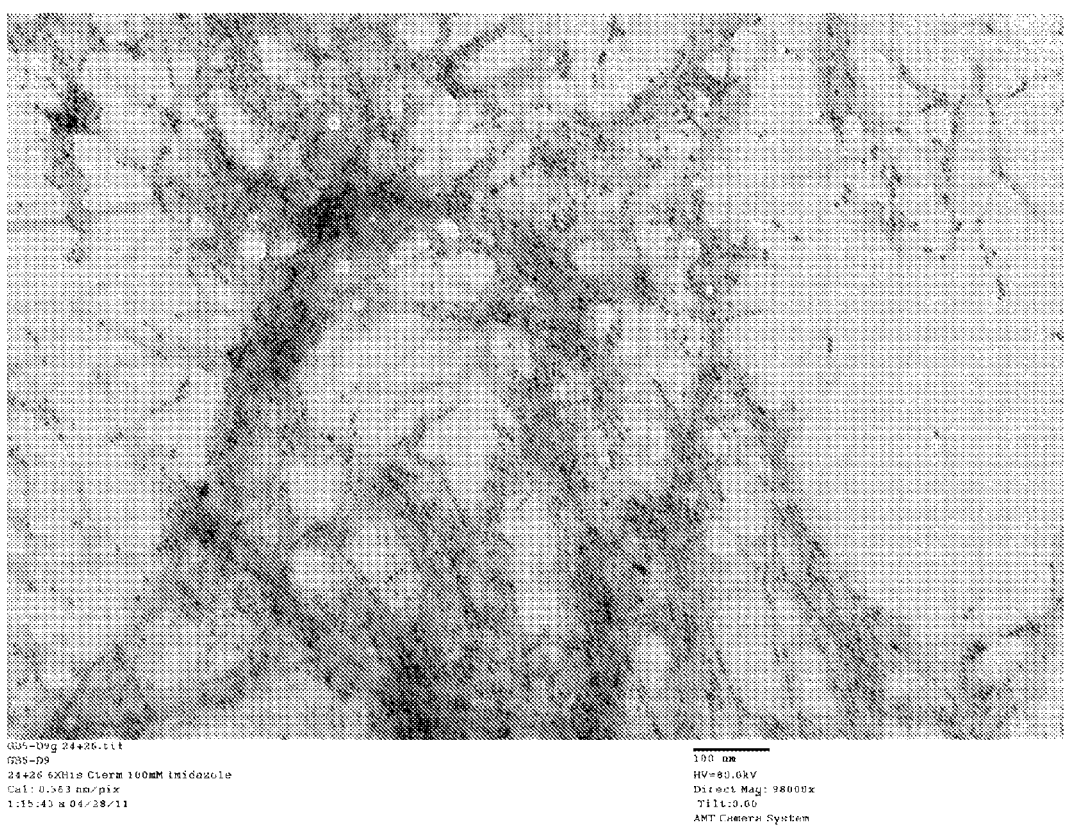
FIG. 24 presents an electron microscopy image showing binding between gold particles fused to Ni-NTA and a 6xHis tag inserted at the C terminus of CsgA.
Figure 26:
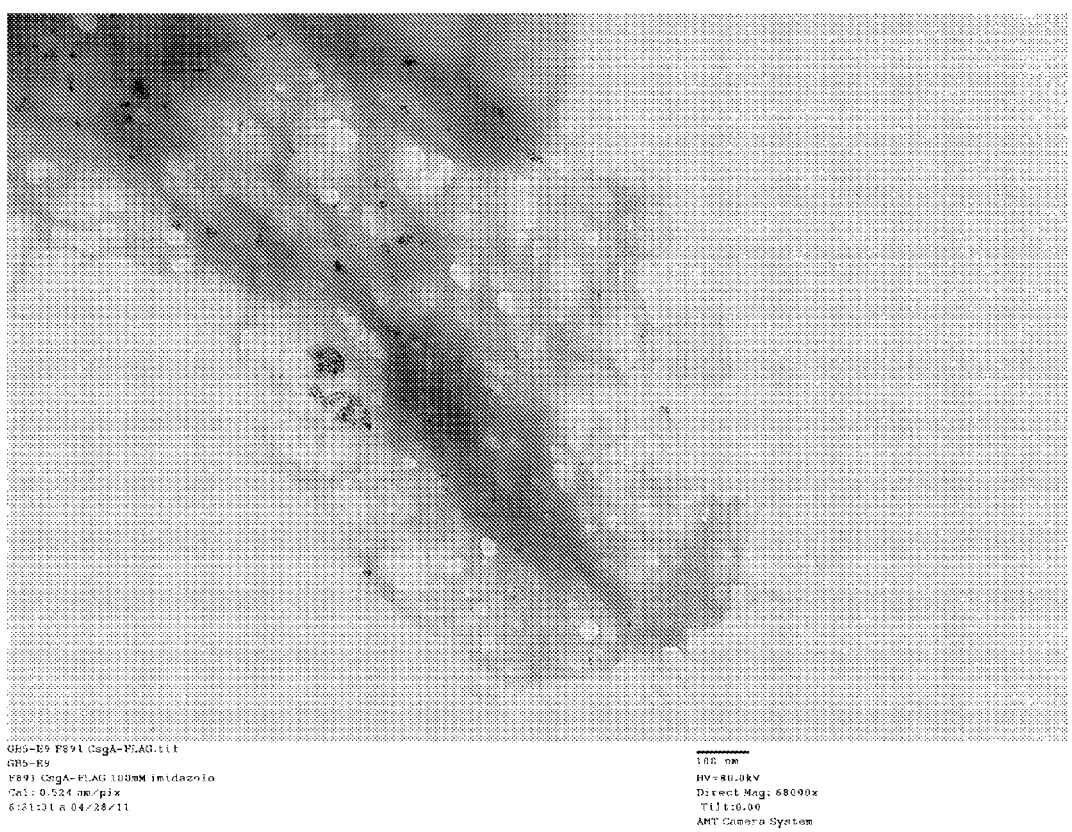
FIG. 26 presents an electron microscopy image of a CsgA-FLAG negative control.

For the electron microscopy experiments, 5 nm Ni-NTA was bound to gold nanoparticles (5 nm in size). Binding conditions included 0.5 M NaCl, 250 mM imidazole and 0.2 v/v % Tween. FIGS. 21-24 show that gold nanoparticles fused to Ni-NTA bind to His tags inserted within the CsgA protein. FIG. 21 shows binding to a 7xHis tag inserted between residues 85 and 86 of CsgA, corresponding to an insertion between regions R2 and R3. FIG. 22 shows binding to a 7xHis tag inserted between residues 107 and 108 of CsgA, corresponding to an insertion between residues R3 and R4. FIG. 23 shows binding to a 7xHis tag inserted between residues 130 and 131, corresponding to an insertion between R4 and R5. FIG. 24 shows binding to a 6xHis tag inserted at the C terminus of CsgA. FIG. 25 presents a negative control of wild type CsgA. FIG. 26 presents a negative control of CsgA-FLAG.

Figure 27:
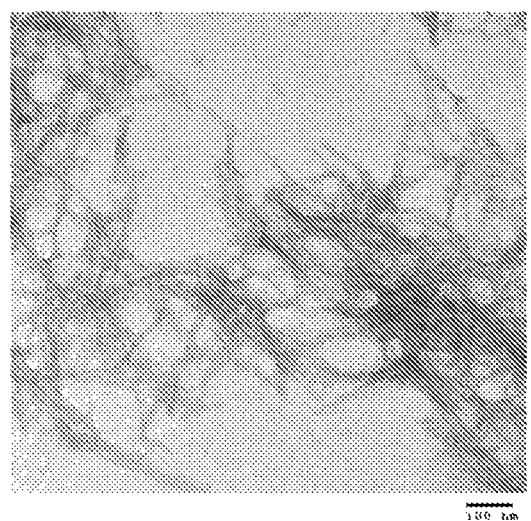
FIG. 27 presents an example of type "1" distinct fibers.
Figure 28:
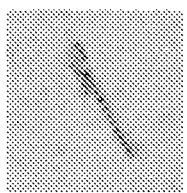
FIG. 28 presents an example of a fiber with the ability to organize NiNTA, classified as "good".
Figure 31:
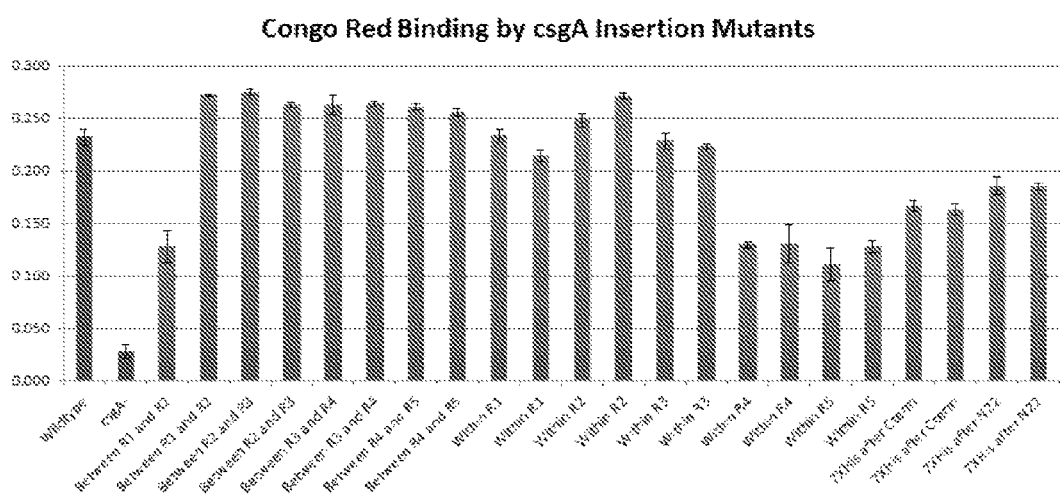
FIG. 31 presents quantitative results of production efficiency of different curli variants with 7xHis tag insertions in different positions. Congo Red (CR) (15 µg/mL) was incubated with cells for 5 minutes, followed by centrifuging the cells at high speed (>13,000 rcf), and measuring the unbound CR in the supernatant using a spectrophotometer at 480 nm (Ishiguro et al., (1985) *J Bacteriol* 164:1233). Absorbance at 480 nm was normalized by $OD_{600}$ of the sample measured by spectrometer before the CR binding assay.

Table 2 summarizes the effect of inserting 7x histidine tags into different positions in the peptide sequence of CsgA on the ability of CsgA to form curli fiber structures, the production level of curli fibers, and the ability of the fibers to bind and align NiNTA-conjugated gold nanoparticles. Semi-quantitative studies of the production level of different curli variants was complemented by quantitative Congo Red assays (FIG. 31), in which Congo Red binding was quantified by incubating CR (15 μg/mL) with cells, centrifuging the cells at high speed (>13,000 rcf), and measuring the unbound CR in the supernatant using a spectrophotometer at 480 nm (Ishiguro et al., (1985) *J Bacteriol* 164:1233). The results showed that insertion of such tags in most positions is minimally disruptive. FIG. 27 shows an example of distinct fibers formed by CsgA with 7x histidine tags inserted, and FIG. 28 shows an example of curli fibers formed by CsgA with 7x histidine tags organizing NiNTA-conjugated gold nanoparticles.

TABLE 2

Insertion of 7XHis tag at a variety of positions in peptide sequence preserves the ability of curli fibers to form and the ability of tags to be displayed.

| His tag insert position | Curli Morphology (1 = distinct fibers --> 4 = indistinct fibers) | Curli: Cell ratio | Ability to organize NiNTA-AuNP |
|---|---|---|---|
| After N22 | 1 | <> | Good |
| After N22 | 1 | <> | Good |
| Between R1 and R2 | 2 | >2 | <> |
| Between R1 and R2 | 2 | >2 | <> |
| Between R2 and R3 | 1 | >2 | Good |
| Between R2 and R3 | 1 | >2 | Good |
| Between R3 and R4 | 1 | >2 | Good |
| Between R3 and R4 | 1 | >2 | Good |
| Between R4 and R5 | 2 | >2 | Good |
| Between R4 and R5 | 2 | >2 | Good |
| Within R1 | 3 | ~1 | Poor |
| Within R1 | 1 | ~1 | Good |
| Within R2 | 2 | >1 | Good |
| Within R2 | 3 | ~1 | Good |
| Within R3 | 3 | <1 | Ok |
| Within R3 | 4 | <1 | Poor |
| Within R4 | 3 | ~1 | Poor |
| Within R4 | 4 | ~1 | Poor |
| Within R5 | 3 | ~1 | Poor |
| Within R5 | 1 | >1 | Poor |
| After C terminus | 1 | >1 | Good |
| After C terminus | 1 | >1 | Good |
| CsgA KO | N/A | 0 | N/A |
| No insert | 1 | >2 | N/A |

Example 7

Mutagenesis of CsgA

In order to minimize potential background binding, mutational analysis was conducted by substituting several residues within CsgA with alanine residues. The choice of residues to mutate was based on Peelle et al. (2005), Design Criteria for Engineering Inorganic Material-Specific Peptides," *Langmuir* 21(15):6929. Peelle et al. demonstrated a potential role for histidine in binding to CdS and a potential role for cysteine, histidine, methionine and tryptophan in binding to ZnS and Au. As a negative control for CdS, ZnS and Au binding, H, M, W and/or C residues were replaced with alanine or a similar residue.

Residues of the CsgA protein that were mutated are indicated in bold and underlining as follows:

(SEQ ID NO: 71)
GVVPQYGGGGNHGGGGNNSGPN (SEQ ID NO: 72)
SELNIYQYGGGNSALALQTDARN (SEQ ID NO: 73)
SDLTITQHGGGNGADVGQGSDD (SEQ ID NO: 74)
SSIDLTQRGFGNSATLDQWNGKN (SEQ ID NO: 75)
SEMTVKQFGGGNGAAVDQTASN

-continued (SEQ ID NO: 76)
SSVNVTQVGFGNNATAHQY

The corresponding sequences containing alanine substitutions, which are shown in bold and underlining, are as follows:

(SEQ ID NO: 105)
GVVPQYGGGNAGGGGNNSGPN (SEQ ID NO: 106)
SELNIYQYGGGNSALALQTDARN (SEQ ID NO: 107)
SDLTITQAGGGNGADVGQGSDD (SEQ ID NO: 108)
SSIDLTQRGFGNSATLDQANGKN (SEQ ID NO: 109)
SEATVKQFGGGNGAAVDQTASN (SEQ ID NO: 110)
SSVNVTQVGFGNNATAAQY

The codons that were mutated are shown in bold and underlining, as follows:

(SEQ ID NO: 111)
ATGAAACTTT TAAAAGTAGC AGCAATTGCA GCAATCGTAT

TCTCCGGTAG CGCTCTGCCA GGTGTTGTTC CTCAGTACGG

CGGCGGCGGT AACCACGGTG GTGGCGGTAA TAATAGCGGC

CCAAATTCTG AGCTGAACAT TTACCAGTAC GGTGGCGGTA

ACTCTGCACT TGCTCTGCAA ACTGATGCCC GTAACTCTGA

CTTGACTATT ACCCAGCATG GCGGCGGTAA TGGTGCAGAT

GTTGGTCAGG GCTCAGATGA CAGCTCAATC GATCTGACCC

AACGTGGCTT CGGTAACAGC GCTACTCTTG ATCAGTGGAA

CGGCAAAAATT CTGAAATGA CGGTTAAACA GTTCGGTGGT

GGCAACGGTG CTGCAGTTGA CCAGACTGCA TCTAACTCCT

CCGTCAACGT GACTCAGGTT GGCTTTGGTA ACAACGCGAC

CGCTCATCAG TACTAA

Quikchange® (Agilent Technologies, Santa Clara, Calif.) mutagenesis was used to mutate the above codons.
The following primers were used:

CsgA-H32A(mut)-f (D1396)
(SEQ ID NO: 112)
5'-GGCGGCGGTAACGCCGGTGGTGGCGG-3'

CsgA-H32A(mut)-r (D1397)
(SEQ ID NO: 113)
5'-CCGCCACCACCGGCGTTACCGCCGCC-3'

CsgA-H73A(mut)-f (D1398)
(SEQ ID NO: 114)
5'-GACTTGACTATTACCCAGGCTGGCGGCGGTAATGGT-3'

CsgA-H73A(mut)-r (D1399)
(SEQ ID NO: 115)
5'-ACCATTACCGCCGCCAGCCTGGGTAATAGTCAAGTC-3'

CsgA-W106A(mut)-f (D1400)

(SEQ ID NO: 116)
5'-CAGCGCTACTCTTGATCAGGCGAACGGCAAAAATTCTGAA-3'

CsgA-W106A(mut)-r (D1401)
(SEQ ID NO: 117)
5'- TTCAGAATTTTTGCCGTTCGCCTGATCAAGAGTAGCGCTG-3'

CsgA-M133A(mut)-f (D1402)
(SEQ ID NO: 118)
5'-TTGATCAGTGGAACGGCAAAAATTCTGAAGCGACGGTTAAACA
GTTC-3'

CsgA-M133A(mut)-r (D1403)
(SEQ ID NO: 119)
5'-GAACTGTTTAACCGTCGCTTCAGAATTTTTGCCGTTCCACTGA
TCAA-3'

CsgA-H149A(mut)-r TmNN 71/50 (D1404)
(SEQ ID NO: 120)
5' GACAATACGCGTTTAGTACTGAgcAGCG GTCGCGTTGTTA 3'

TmNN 63/54 PciI-TermT1-r (D743)
(SEQ ID NO: 121)
5' ATTTTCACATGTTCTAGGGCGGCGGATTTG 3'

Example 8

Living Factories for Supramolecular Copolymers

Demonstrated herein is a living factory which produces supramolecular copolymers whose spatial organization and function at the 10 nm-10 μm scale are controlled by genetic circuits, and encoded by amino acid sequence at the 1-10 nm scale. This is the first demonstration of synthetic genetic circuits operating in cells being used to spatially organize the building blocks of nanostructured materials.

To create block-copolymers of CsgA and histidine tagged CsgA whose organization is controlled by genetic circuits, CsgA was placed under the control of an aTc inducible riboregulator and CsgA-7xHis was placed under the control of an AHL inducible riboregulator (Isaacs et al., (2004) *Nat. Biotech.* 22:841). Plasmids bearing CsgA under the control of the aTc riboregulator were transformed into one population of cells to create Cell A, and a second population of cells was transformed with plasmids bearing CsgA-7xHis under the control of the AHL riboregulator to create Cell B. Cell A was grown in media with 15.6 ng/ml, 31.2 ng/ml, 62.5 ng/ml, 125 ng/ml, 250 ng/ml or 500 ng/ml aTc for 16 hours, allowing the cells to create CsgA polymer segments on a plastic coverslip. The coverslip was then washed and transferred to media in which Cell B is grown and induced with 1 nM, 2 nM, 4 nM, 7.9 nM, 15.6 nM, 31.2 nM, 62.5 nM, 125 nM, 250 nM, 500 nM or 1 uM AHL for 16 hours, allowing polymer segments consisting of CsgA-7xHis to grow on top of the formerly deposited CsgA polymer segments. FIG. 32C shows that copolymers grown in this way contain segments which bind NiNTA-conjugated gold nanoparticles via histidine tags and contain other segments which do not. This is in contrast to polymers consisting of only CsgA, which do not bind NiNTA-conjugated gold nanoparticles to a significant degree (FIG. 32A) and polymers consisting of only CsgA-7xHis, which bind the particles uniformly along their length (FIG. 32B).

To pattern at the 1-10 nm scale, some embodiments described herein take advantage of the ability of individual beta strands on CsgA to be uniquely addressed. It is possible to attach histidine tags to every beta strand in the folded CsgA structure while still allowing curli fiber formation and allowing the histidine tags to be exposed. Histidine tags were inserted at different positions on opposite sides of the folded CsgA structure and by changing the register of displayed histidine tags on opposite sides of CsgA, the register of NiNTA-conjugated gold nanoparticles bound to the polymer can also be changed.

Figure 33:
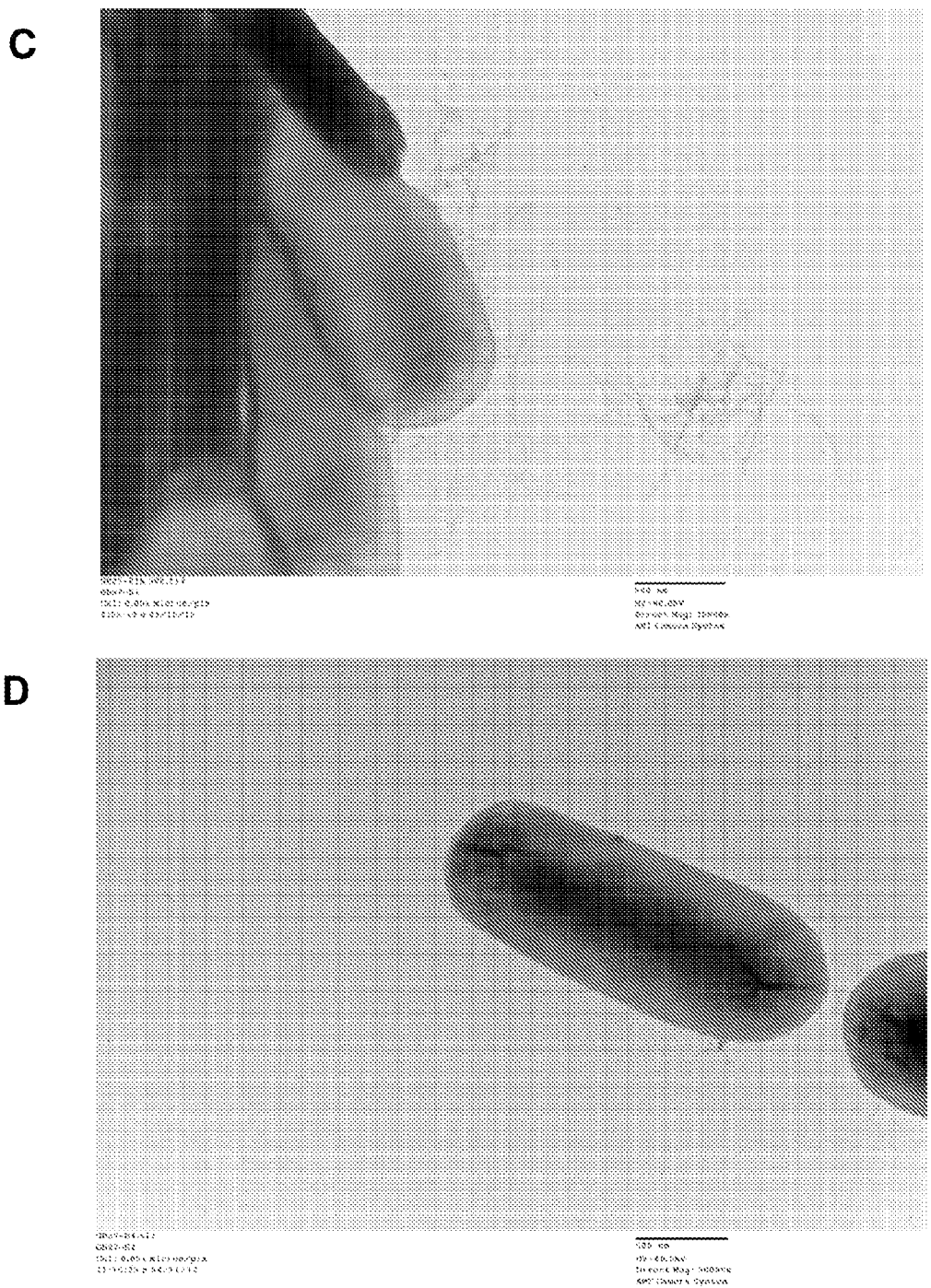
FIG. 33 demonstrates tight control of curli fiber expression by riboregulators.

In some embodiments, riboregulators that have very low "leaky" expression of the genes under their control are used for co-polymer applications, to produce only the desired type of polymer subunit at any given time. In some embodiments, leakiness of standard promoters such as PL-lacO1 can result in curli production in absence of inducer (FIG. 27). In contrast, aTc induced and AHL induced riboregulators allow curli fiber production only in presence of inducers. FIG. 33A shows that aTc induced riboregulators allow curli fiber formation in the presence of aTc, but not in its absence (FIG. 33B) Similarly, FIG. 33C shows that AHL induced riboregulators allow curli fiber formation in the presence of AHL, but not in its absence (FIG. 33D).

To control the distribution of segment lengths, the distribution of curli fiber segment lengths was mapped as a function of inducer concentration and growth time. FIG. 38 shows that in some embodiments, the distribution of curli fiber lengths is more strongly dependent on growth time than on inducer concentration. As cells were grown with inducer for increasing time, the fibers got longer and also became more heterogeneous in length; when allowed to grow even longer, the fibers underwent structural change and their average length decreased.

In this non-limiting embodiment of co-polymer production, the E. coli strain used had the following properties: endogenous CsgA was knocked out so that the only source of CsgA for fiber formation was the gene under control of an inducible promoter; for the aTc inducible riboregulator, a PRO cassette which overexpresses TetR repressor was included for tight repression. FIG. 36 shows that without overexpressed TetR repressor, the aTc induced riboregulator was leaky—GFP under the control of this riboregulator was expressed whether or not aTc inducer was present. In the case of the AHL inducible riboregulator, the plasmid carrying the riboregulator also had a constitutively expressed LuxR repressor, obviating the need for a separate entity which overexpressed LuxR repressor; and the strain producing curli fibers was kept in solution so that inducers could be readily changed. A strain with the OmpR234 mutation was used for this property (Prigent-Combaret et al., (2000) *Environmental Microbiology* 2:450). Other cell strains, even ones with modifications such as overexpression of the entire curli operon (Cherny et al., (2005) *Journal of Molecular Biology* 352:245), did not form distinct fibers in liquid media (FIG. 37). The liquid media used to allow OmpR234 mutants to produce curli fibers was M63 minimal media (Miller, J. H. (1972) Experiments in Molecular Genetics. Cold Spring Harbor, N.Y.: Cold Spring Harbor Laboratory Press).

In some embodiments, the copy number of the plasmids on which riboregulated CsgA or CsgA-7×His reside was found to be relevant for the ability to induce expression of CsgA. For example, Table 3 shows that in some embodiments, it was found to be preferable if the construct was on a plasmid with a medium-copy p15A origin of replication (Lutz et al., (1997) *Nucleic Acids Res* 25:1203) to allow inducible curli fiber production at a wide range of inducer concentrations.

TABLE 3

Relevance of plasmid copy number for curli production.

| | 1 uM AHL | 500 nM AHL | 250 nM AHL | 125 nM AHL | 62.5 nM AHL | 31.2 nM AHL | 15.6 nM AHL | 7.9 nM AHL | 4 nM AHL | 2 nM AHL | 1 nM AHL | 0.5 AHL | 0.25 AHL |
|---|---|---|---|---|---|---|---|---|---|---|---|---|---|
| Low copy | No curli | No curli | No curli | No curli | No curli | No curli | No curli | No curli | No curli | No curli | No curli | No curli | No curli |
| Medium copy | Curli | Curli | Curli | Curli | Curli | Curli | Curli | Curli | Curli | Curli | N/A | N/A | N/A |
| High copy | No curli | No curli | No curli | No curli | No curli | No curli | No curli | No curli | No curli | Curli | Curli | No curli | Curli |

Example 9

Dynamic Biomaterials Whose Composition Changes in Response to Environment

Cells were developed that express proteins under the control of gene regulatory elements to assemble materials with designed spatial organization and function. Such systems can leverage advances in synthetic biology to potentially create dynamic biomaterials which are assembled and remodeled in response to environmental cues. Dynamic biomaterials which mimic the ever-changing extracellular matrix would be valuable tools for regenerative medicine and tissue engineering.

A living factory that produces copolymer material whose composition changes as cell density increases is demonstrated herein. This illustrates a dynamic biomaterial which is responsive to environmental factors, in this case one relevant to tissue engineering applications.

A non-limiting embodiment of this system consists of two types of cells:

Cell 1 which contains an aTc ribo CsgA (CmR) plasmid and an aTc induced luxI (AmpR) plasmid; and Cell 2 which contains an: AHL ribo CsgA-7×His (AmpR) plasmid.

Binding to NiNTA-conjugated gold nanoparticles (as described in Example 5) was used to distinguish fiber segments formed by CsgA containing histidine tags from those formed by wild-type CsgA.

In condition 1, Cell 1 was grown in Carb and induced with aTc, which drives CsgA expression from aTc ribo CsgA (CmR) and AHL production via aTc induced luxI (AmpR). The number of cells bearing CmR did not increase significantly with time since there was no selection for CmR, so the CmR plasmid was not propagated in most cell division events. By contrast, the number of cells with AmpR plasmid was growing exponentially and the AHL concentration was rapidly increasing. After 26 h, some curli fibers were seen, and they did not bind NiNTA gold particles (FIG. 34A).

In condition 2, Cell 2 was grown in Carb and induced with aTc. The number of cells bearing AHL ribo CsgA7×His (AmpR) plasmid grew exponentially, but no curli was produced since there was no AHL present. After 26 h, no curli fibers were seen (FIG. 34B).

In condition 3, Cell 1 was co-cultured with Cell 2 in Carb and induced with aTc. Early on, there was CsgA curli production from aTc ribo CsgA (CmR), but not enough AHL had been made via aTc induced luxI (AmpR) to drive CsgA7×His curli production from AHL ribo CsgA7×His (AmpR). The curli formed early on at 8 hour and 12 hour timepoints did not bind NiNTA gold particles (FIG. 35A, B). Later, since there was selection for AmpR but not for CmR, the number of AHL ribo CsgA7×His (AmpR) overwhelm aTc ribo CsgA (CmR). At the same time AHL concentration had also reached high levels, allowing induction of CsgA7× His from AHL ribo CsgA7×His (AmpR) at 16 hour and 24 hour timepoints (FIG. 35C, D). At that time, the majority of subunits available to form fibers were CsgA-7×His.

Example 10

Multicellular Pattern Formation

Patterning on multiple length scales can be achieved by combining the demonstration described in Example 8 with methods to spatially pattern the nanopatterned fiber-producing cells themselves. A non-limiting example of a spatial patterning technique was demonstrated based on creation of standing waves in liquid media. Such waves create cell-accumulating pressure nodes and antinodes in intricate patterns (FIG. 39, from physics.ucla.edu/demoweb/demo-manual/acoustics/effects_of_sound/chladniarray.jpg). 15 ml of M63 minimal media was placed with $5 \times 10^7$/ml OmpR234 *E. coli* cells in a 100 mm Petri dish, then incubated at 30° C. for 28 h on the top self of a VWR 1585 Shaking Incubator set at 300 rpm. The shaking action created concentric ring standing waves in the Petri dish with wavelength ~1.67 cm, and such waves created concentric ring pattern deposits of cells at a spacing of ~0.83 cm (FIG. 40A). Examination of the material in the rings under TEM revealed curli fiber formation (FIG. 40B).

This non-limiting embodiment created centimeter-scale patterns, but can be generalized to create patterns at any scale by tuning the frequency of driving oscillations which set up standing waves. Ultrasonic frequencies could be used, for example, to create micron-scale patterns.

Example 11

Fibers Attached to Cells Allow Cells to Interface with Magnetic Fields

Surface-attached fibers with affinity tags or natural affinity for biomaterials can be used to bind paramagnetic nanoparticles, allowing cells to interface with magnetic fields. For example, it was found that incubating curli fiber-displaying cells with 10 nM 30 nm iron oxide nanoparticles (IONPs) for at least 1 hour allowed the cells to move toward an N42 neodynium magnet as observed under a microscope (FIG. 41B, FIG. 42B). Negative control cells (CsgA KO), which did not express fibers, when incubated for at least 1 hour with 10 nM 30 nm IONPs did not move (FIG. 41A, FIG. 42A). At the macroscale, incubating fiber-displaying cells with IONP allowed magnetic separation of cells to a pellet (FIG. 43), leaving the supernatant clear. A sample of cells not displaying fibers incubated with IONP did not separate and the supernatant remained cloudy.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety, particularly for the disclosure referenced herein.

What is claimed is:

1. A bacterial cell that is genetically engineered to express at least one modified amyloid fiber that comprises at least one inorganic-binding peptide.

2. The bacterial cell of claim 1, wherein the at least one modified amyloid fiber is bound through the inorganic-binding peptide to at least one metal or metal nanoparticle.

3. The bacterial cell of claim 2, wherein the at least one metal or metal nanoparticle comprises a gold nanoparticle, a silver nanoparticle, zinc sulfate, cadmium sulfate, iron oxide, cobalt oxide, cobalt platinum, iron platinum or a quantum dot.

4. The bacterial cell of claim 1, wherein expression of the at least one modified amyloid fiber is under the control of an inducible promoter.

5. The bacterial cell of claim 1, wherein the bacterial cell is an *Escherichia coli* (*E. coli*) cell.

6. The bacterial cell of claim 1, wherein the at least one modified amyloid fiber comprises a curli fiber.

7. The bacterial cell of claim 6, wherein the bacterial cell expresses a csgBAC operon, a csgDEFG operon, or both a csgBAC operon and a csgDEFG operon, and wherein one or more components of the csgBAC operon, the csgDEFG operon, or both the csgBAC operon and the csgDEFG operon is/are genetically engineered.

8. The bacterial cell of claim 7, wherein one or more components of the csgBAC operon, the csgDEFG operon, or both the csgBAC operon and the csgDEFG operon is/are expressed on a plasmid, wherein csgA, csgB, or both csgA and csgB is/are expressed on a plasmid under the control of an inducible promoter, wherein one or more heterologous polypeptide domains are attached to CsgA, and/or wherein csgA, csgB, or both csgA and csgB is/are genetically engineered to express charged residues.

9. The bacterial cell claim 1, wherein the at least one modified amyloid fiber is genetically engineered to promote release of the at least one modified amyloid fiber from the bacterial cell.

10. The bacterial cell of claim 9, wherein exogenous D-amino acids enable detachment of amyloid fibers from the bacterial cell surface and/or wherein the bacterial cell overexpresses a gene encoding for an enzyme that converts L-amino acids to D-amino acids.

11. The bacterial cell of claim 1, wherein the at least one inorganic-binding peptide comprises a metal-binding peptide or a semiconductor-binding peptide.

12. The bacterial cell of claim 11, wherein the at least one inorganic-binding peptide comprises a gold-binding peptide (Au-BP), a ZnS-binding peptide (ZnS-BP), or a CdS-binding peptide (CdS-BP).

13. The bacterial cell of claim 12, wherein the Au-BP comprises the sequence LKAHLPPSRLPS (SEQ ID NO:1), wherein the ZnS-BP comprises the sequence CNNPMHQNC (SEQ ID NO:2), or wherein the CdS-BP comprises the sequence SLTPLTTSHLRS (SEQ ID NO:3).

14. The bacterial cell of claim 6, wherein the curli fiber binds to and nucleates inorganic nanomaterials, comprises tetra-glutamate peptides, and/or displays a conductive cytochrome on the surface of the curli fiber.

15. The bacterial cell of claim 4, wherein the inducible promoter is a visible-light-inducible promoter or comprises a UV-inducible toggle switch.

16. A combination of two or more of the bacterial cells of claim 1, wherein the bacterial cells are spatially patterned.

17. A bacterial cell that is genetically engineered to express at least one modified amyloid fiber that comprises at least one heterologous polypeptide domain, wherein the bacterial cell expresses a csgBAC operon, a csgDEFG operon, or both a csgBAC operon and a csgDEFG operon, and wherein at least one component of the csgBAC operon, the csgDEFG operon or both the csgBAC operon and the csgDEFG is genetically engineered.

18. The bacterial cell of claim 17, wherein the csgBAC operon, the csgDEFG operon, or both the csgBAC operon and the csgDEFG operon is/are expressed on a plasmid.

19. The bacterial cell of claim 17, the csgBAC operon, the csgDEFG operon, or both the csgBAC operon and the csgDEFG operon is/are under the control of an inducible promoter.

20. The bacterial cell of claim 17, wherein at least one of the heterologous polypeptide domains is attached to CsgA.

21. The bacterial cell of claim 17, wherein csgA, csgB, or both csgA and csgB is/are genetically engineered to express charged residues.

* * * * *

SEQUENCE LISTING

```
<160> NUMBER OF SEQ ID NOS: 133

<210> SEQ ID NO 1
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1

Leu Lys Ala His Leu Pro Pro Ser Arg Leu Pro Ser
1               5                   10

<210> SEQ ID NO 2
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 2
```

Cys Asn Asn Pro Met His Gln Asn Cys
1               5

<210> SEQ ID NO 3
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 3

Ser Leu Thr Pro Leu Thr Thr Ser His Leu Arg Ser
1               5                   10

<210> SEQ ID NO 4
<211> LENGTH: 4204
<212> TYPE: DNA
<213> ORGANISM: Artificial sequence
<220> FEATURE:
<223> OTHER INFORMATION: Synthetic polynucleotide

<400> SEQUENCE: 4

| | | | | | |
|---|---|---|---|---|---|
| ctcgagatgc | tagcaattgt | gagcggataa | caattgacat | tgtgagcgga | taacaagata | 60 |
| ctgagcacat | cagcaggacg | cactgacctt | aattaaaaga | attcattaaa | gaggagaaag | 120 |
| gtaccatgcg | taaaggagaa | gaactttca | ctggagttgt | cccaattctt | gttgaattag | 180 |
| atggtgatgt | taatgggcac | aaattttctg | tcagtggaga | gggtgaaggt | gatgcaacat | 240 |
| acggaaaact | tacccttaaa | tttatttgca | ctactggaaa | actacctgtt | ccatggccaa | 300 |
| cacttgtcac | tactttcggt | tatggtgttc | aatgctttgc | gagatacca | gatcatatga | 360 |
| aacagcatga | cttttcaag | agtgccatgc | ccgaaggtta | tgtacaggaa | agaactatat | 420 |
| ttttcaaaga | tgacgggaac | tacaagacac | gtgctgaagt | caagtttgaa | ggtgataccc | 480 |
| ttgttaatag | aatcgagtta | aaaggtattg | attttaaaga | agatggaaac | attcttggac | 540 |
| acaaattgga | atacaactat | aactcacaca | atgtatacat | catggcagac | aaacaaaaga | 600 |
| atggaatcaa | agttaacttc | aaaattagac | acaacattga | agatggaagc | gttcaactag | 660 |
| cagaccatta | tcaacaaaat | actccaattg | gcgatggccc | tgtccttta | ccagacaacc | 720 |
| attacctgtc | cacacaatct | gccctttcga | aagatcccaa | cgaaaagaga | gaccacatgg | 780 |
| tccttcttga | gtttgtaaca | gctgctggga | ttacacatgg | catggatgaa | ctatacaaat | 840 |
| aaaagcttga | tatcgaattc | ctgcagcccg | ggggatccca | tggtacgcgt | ggcatcaaat | 900 |
| aaaacgaaag | gctcagtcga | aagactgggc | ctttcgtttt | atctgttgtt | tgtcggtgaa | 960 |
| cgctctcctg | agtaggacaa | atccgccgcc | ctagacctag | ggtacgggtt | tgctgcccg | 1020 |
| caaacgggct | gttctggtgt | tgctagtttg | ttatcagaat | cgcagatccg | gcttcaggtt | 1080 |
| tgccggctga | aagcgctatt | tcttccagaa | ttgccatgat | tttttcccca | cgggaggcgt | 1140 |
| cactggctcc | cgtgttgtcg | gcagctttga | ttcgataagc | agcatcgcct | gtttcaggct | 1200 |
| gtctatgtgt | gactgttgag | ctgtaacaag | ttgtctcagg | tgttcaattt | catgttctag | 1260 |
| ttgctttgtt | ttactggttt | cacctgttct | attaggtgtt | acatgctgtt | catctgttac | 1320 |
| attgtcgatc | tgttcatggt | gaacagcttt | aaatgcacca | aaaactcgta | aaagctctga | 1380 |
| tgtatctatc | ttttttacac | cgttttcatc | tgtgcatatg | gacagttttc | cctttgatat | 1440 |
| ctaacggtga | acagttgttc | tactttgttt | gttagtcctt | gatgcttcac | tgatagatac | 1500 |
| aagagccata | agaacctcag | atccttccgt | atttagccag | tatgttctct | agtgtggttc | 1560 |
| gttgtttttg | cgtgagccat | gagaacgaac | cattgagatc | atgcttactt | tgcatgtcac | 1620 |

```
tcaaaaattt tgcctcaaaa ctggtgagct gaattttttgc agttaaagca tcgtgtagtg    1680 ttttttcttag tccgttacgt aggtaggaat ctgatgtaat ggttgttggt attttgtcac    1740
cattcatttt tatctggttg ttctcaagtt cggttacgag atccatttgt ctatctagtt    1800
caacttggaa aatcaacgta tcagtcgggc ggcctcgctt atcaaccacc aatttcatat    1860
tgctgtaagt gtttaaatct ttacttattg gtttcaaaac ccattggtta agccttttaa    1920
actcatggta gttattttca agcattaaca tgaacttaaa ttcatcaagg ctaatctcta    1980
tatttgcctt gtgagttttc ttttgtgtta gttctttttaa taaccactca taaatcctca    2040
tagagtattt gttttcaaaa gacttaacat gttccagatt atattttatg aattttttta    2100
actggaaaag ataaggcaat atctcttcac taaaaactaa ttctaatttt tcgcttgaga    2160
acttggcata gtttgtccac tggaaaatct caaagccttt aaccaaagga ttcctgattt    2220
ccacagttct cgtcatcagc tctctggttg ctttagctaa tacaccataa gcattttccc    2280
tactgatgtt catcatctga gcgtattggt tataagtgaa cgataccgtc cgttctttcc    2340
ttgtagggtt ttcaatcgtg gggttgagta gtgccacaca gcataaaatt agcttggttt    2400
catgctccgt taagtcatag cgactaatcg ctagttcatt tgctttgaaa acaactaatt    2460
cagacataca tctcaattgg tctaggtgat tttaatcact ataccaattg agatgggcta    2520
gtcaatgata attactagtc cttttccttt gagttgtggg tatctgtaaa ttctgctaga    2580
cctttgctgg aaaacttgta aattctgcta gaccctctgt aaattccgct agacctttgt    2640
gtgttttttt tgtttatatt caagtggtta aatttatag aataaagaaa gaataaaaaa    2700
agataaaaag aatagatccc agccctgtgt ataactcact actttagtca gttccgcagt    2760
attacaaaag gatgtcgcaa acgctgtttg ctcctctaca aaacagacct taaaacccta    2820
aaggcttaag tagcaccctc gcaagctcgg gcaaatcgct gaatattcct tttgtctccg    2880
accatcaggc acctgagtcg ctgtcttttt cgtgacattc agttcgctgc gctcacggct    2940
ctggcagtga atgggggtaa atggcactac aggcgccttt tatggattca tgcaaggaaa    3000
ctacccataa tacaagaaaa gcccgtcacg ggcttctcag ggcgttttat ggcgggtctg    3060
ctatgtggtg ctatctgact ttttgctgtt cagcagttcc tgccctctga ttttccagtc    3120
tgaccacttc ggattatccc gtgacaggtc attcagactg gctaatgcac ccagtaaggc    3180
agcggtatca tcaacaggct tacccgtctt actgtcccta gtgcttggat tctcaccaat    3240
aaaaaacgcc cggcggcaac cgagcgttct gaacaaatcc agatggagtt ctgaggtcat    3300
tactggatct atcaacagga gtccaagcga gctcgatatc aaattacgcc ccgccctgcc    3360
actcatcgca gtactgttgt aattcattaa gcattctgcc gacatggaag ccatcacaga    3420
cggcatgatg aacctgaatc gccagcggca tcagcacctt gtcgccttgc gtataatatt    3480
tgcccatggt gaaaacgggg gcgaagaagt tgtccatatt ggccacgttt aaatcaaaac    3540
tggtgaaact cacccaggga ttggctgaga cgaaaaacat attctcaata aacccttag    3600 ggaaataggc caggttttca ccgtaacacg ccacatcttg cgaatatatg tgtagaaact    3660
gccggaaatc gtcgtggtat tcactccaga gcgatgaaaa cgtttcagtt tgctcatgga    3720
aaacggtgta caagggtgag acactatccc atatcaccag ctcaccgtct ttcattgcca    3780
tacggaattc cggatgagca ttcatcaggc gggcaagaat gtgaataaag gccggataaa    3840
acttgtgctt attttctttt acggtcttta aaaaggccgt aatatccagc tgaacggtct    3900
ggttataggt acattgagca actgactgaa atgcctcaaa atgttcttta cgatgccatt    3960
```

| | |
|---|---|
| gggatatatc aacggtggta tatccagtga ttttttctc cattttagct tccttagctc | 4020 |
| ctgaaaatct cgataactca aaaaatacgc ccggtagtga tcttatttca ttatggtgaa | 4080 |
| agttggaacc tcttacgtgc cgatcaacgt ctcattttcg ccagatatcg acgtctaaga | 4140 |
| aaccattatt atcatgacat taacctataa aaataggcgt atcacgaggc cctttcgtct | 4200 |
| tcac | 4204 |

<210> SEQ ID NO 5
<211> LENGTH: 31
<212> TYPE: DNA
<213> ORGANISM: Artificial sequence
<220> FEATURE:
<223> OTHER INFORMATION: Synthetic polynucleotide

<400> SEQUENCE: 5

| | |
|---|---|
| ctacgcgtga tgtattagta ctgatgagcg g | 31 |

<210> SEQ ID NO 6
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 6

| | |
|---|---|
| gaggtaccat gaaactttta aaagtagcag | 30 |

<210> SEQ ID NO 7
<211> LENGTH: 3907
<212> TYPE: DNA
<213> ORGANISM: Artificial sequence
<220> FEATURE:
<223> OTHER INFORMATION: Synthetic polynucleotide

<400> SEQUENCE: 7

| | |
|---|---|
| ctcgagatgc tagcaattgt gagcggataa caattgacat tgtgagcgga taacaagata | 60 |
| ctgagcacat cagcaggacg cactgacctt aattaaaaga attcattaaa gaggagaaag | 120 |
| gtaccatgaa acttttaaaa gtagcagcaa ttgcagcaat cgtattctcc ggtagcgctc | 180 |
| tggcaggtgt tgttcctcag tacggcggcg gcggtaacca cggtggtggc ggtaataata | 240 |
| gcggcccaaa ttctgagctg aacatttacc agtacggtgg cggtaactct gcacttgctc | 300 |
| tgcaaactga tgcccgtaac tctgacttga ctattaccca gcatggcggc ggtaatggtg | 360 |
| cagatgttgg tcagggctca gatgacagct caatcgatct gacccaacgt ggcttcggta | 420 |
| acagcgctac tcttgatcag tggaacggca aaaattctga atgacggtt aaacagttcg | 480 |
| gtggtggcaa cggtgctgca gttgaccaga ctgcatctaa ctcctccgtc aacgtgactc | 540 |
| aggttggctt tggtaacaac gcgaccgctc atcagtacta atacatcacg cgtggcatca | 600 |
| aataaaacga aaggctcagt cgaaagactg ggcctttcgt tttatctgtt gtttgtcggt | 660 |
| gaacgctctc ctgagtagga caaatccgcc gccctagacc tagggtacgg ttttgctgc | 720 |
| ccgcaaacgg gctgttctgg tgttgctagt ttgttatcag aatcgcagat ccggcttcag | 780 |
| gtttgccggc tgaaagcgct atttcttcca gaattgccat gatttttcc ccacgggagg | 840 |
| cgtcactggc tcccgtgttg tcggcagctt tgattcgata agcagcatcg cctgtttcag | 900 |
| gctgtctatg tgtgactgtt gagctgtaac aagttgtctc aggtgttcaa tttcatgttc | 960 |
| tagttgcttt gttttactgg tttcacctgt tctattaggt ttacatgct gttcatctgt | 1020 |
| tacattgtcg atctgttcat ggtgaacagc tttaaatgca ccaaaaactc gtaaaagctc | 1080 |

```
tgatgtatct atcttttta caccgttttc atctgtgcat atggacagtt ttccctttga   1140
tatctaacgg tgaacagttg ttctactttt gtttgttagt cttgatgctt cactgataga   1200
tacaagagcc ataagaacct cagatccttc cgtatttagc cagtatgttc tctagtgtgg   1260
ttcgttgttt ttgcgtgagc catgagaacg aaccattgag atcatgctta ctttgcatgt   1320
cactcaaaaa ttttgcctca aaactggtga gctgaatttt tgcagttaaa gcatcgtgta   1380
gtgtttttct tagtccgtta cgtaggtagg aatctgatgt aatggttgtt ggtattttgt   1440
caccattcat ttttatctgg ttgttctcaa gttcggttac gagatccatt tgtctatcta   1500
gttcaacttg gaaaatcaac gtatcagtcg ggcggcctcg cttatcaacc accaatttca   1560
tattgctgta agtgtttaaa tctttactta ttggtttcaa acccattgg ttaagccttt    1620 taaactcatg gtagttattt tcaagcatta acatgaactt aaattcatca aggctaatct   1680
ctatatttgc cttgtgagtt ttcttttgtg ttagttcttt taataaccac tcataaatcc   1740
tcatagagta tttgttttca aaagacttaa catgttccag attatatttt atgaattttt   1800
ttaactggaa aagataaggc aatatctctt cactaaaaac taattctaat ttttcgcttg   1860
agaacttggc atagtttgtc cactggaaaa tctcaaagcc tttaaccaaa ggattcctga   1920
tttccacagt tctcgtcatc agctctctgg ttgctttagc taatacacca taagcatttt   1980
ccctactgat gttcatcatc tgagcgtatt ggttataagt gaacgatacc gtccgttctt   2040
tccttgtagg gttttcaatc gtggggttga gtagtgccac acagcataaa attagcttgg   2100
tttcatgctc cgttaagtca tagcgactaa tcgctagttc atttgctttg aaaacaacta   2160
attcagacat acatctcaat tggtctaggt gattttaatc actataccaa ttgagatggg   2220
ctagtcaatg ataattacta gtccttttcc tttgagttgt gggtatctgt aaattctgct   2280
agacctttgc tggaaaactt gtaaattctg ctagaccctc tgtaaattcc gctagacctt   2340 tgtgtgttttt ttttgtttat attcaagtgg ttataattta tagaataaag aaagaataaa   2400
aaaagataaa aagaatagat cccagccctg tgtataactc actactttag tcagttccgc   2460
agtattacaa aaggatgtcg caaacgctgt ttgctcctct acaaaacaga ccttaaaacc   2520
ctaaaggctt aagtagcacc ctcgcaagct cgggcaaatc gctgaatatt ccttttgtct   2580
ccgaccatca ggcacctgag tcgctgtctt tttcgtgaca ttcagttcgc tgcgctcacg   2640
gctctggcag tgaatggggg taaatggcac tacaggcgcc ttttatggat tcatgcaagg   2700
aaactaccca taatacaaga aaagcccgtc acgggcttct cagggcgttt tatggcgggt   2760
ctgctatgtg gtgctatctg acttttttgct gttcagcagt tcctgccctc tgattttcca   2820
gtctgaccac ttcggattat cccgtgacag gtcattcaga ctggctaatg cacccagtaa   2880
ggcagcggta tcatcaacag gcttacccgt cttactgtcc ctagtgcttg gattctcacc   2940
aataaaaaac gcccggcggc aaccgagcgt tctgaacaaa tccagatgga gttctgaggt   3000
cattactgga tctatcaaca ggagtccaag cgagctcgat atcaaattac gccccgccct   3060
gccactcatc gcagtactgt tgtaattcat taagcattct gccgacatgg aagccatcac   3120
agacggcatg atgaacctga atcgccagcg gcatcagcac cttgtcgcct tgcgtataat   3180
atttgcccat ggtgaaaacg ggggcgaaga agttgtccat attggccacg tttaaatcaa   3240
aactggtgaa actcacccag ggattggctg agacgaaaaa catattctca ataaacccctt  3300 tagggaaata ggccaggttt tcaccgtaac acgccacatc ttgcgaatat atgtgtagaa   3360
actgccggaa atcgtcgtgg tattcactcc agagcgatga aaacgtttca gtttgctcat   3420
```

```
ggaaaacggt gtaacaaggg tgaacactat cccatatcac cagctcaccg tctttcattg      3480
ccatacggaa ttccggatga gcattcatca ggcgggcaag aatgtgaata aaggccggat      3540
aaaacttgtg cttattttc tttacggtct ttaaaaggc cgtaatatcc agctgaacgg        3600
tctggttata ggtacattga gcaactgact gaaatgcctc aaaatgttct ttacgatgcc      3660
attgggatat atcaacggtg gtatatccag tgatttttt ctccatttta gcttccttag       3720
ctcctgaaaa tctcgataac tcaaaaaata cgcccggtag tgatcttatt tcattatggt     3780
gaaagttgga acctcttacg tgccgatcaa cgtctcattt tcgccagata tcgacgtcta     3840
agaaaccatt attatcatga cattaaccta taaaaatagg cgtatcacga ggcccttcg     3900 tcttcac                                                                3907

<210> SEQ ID NO 8
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 8
gactcgagca gaagtactga cagatgttgc                                         30

<210> SEQ ID NO 9
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 9
ctggtacctt tctcctcttt aattgtcacc ctggacctgg                              40

<210> SEQ ID NO 10
<211> LENGTH: 4500
<212> TYPE: DNA
<213> ORGANISM: Artificial sequence
<220> FEATURE:
<223> OTHER INFORMATION: Synthetic polynucleotide

<400> SEQUENCE: 10
ctcgagcaga agtactgaca gatgttgcac tgctgtgtgt agtaataaat cagccctaaa       60
tgggtaaaat ataaaactaa tggattacat ctgatttcaa tctagccatt acaaatctta     120
aatcaagtgt taaacatgta actaaatgta actcgttata ttaaaatgtt aaccttaagg      180
ttttattaag tttagaaatg atagaaaagt tgtacatttg gttttattg cacaattta        240 aaaaatcata caaatggtga taacttacta ataatgcata taaaaatat ttcggtgtag       300 tcctttcgtc atgtaaaacg ttcttgtttt ttctccacac ctccgtggac aatttttac      360 tgcaaaaaga cgaggtttgt cacggcttgt gcgcaagaca tatcgcagca atcagcgacg     420
ggcaagaaga atgactgtct ggtgcttttt gatagcggaa aacggagatt taaagaaaa       480 caaaatattt ttttgcgtag ataacagcgt atttacgtgg gttttaatac tttggtatga   540
actaaaaaag aaaaatacaa cgcgcgggtg agttattaaa aatatttccg cagacatact    600
ttccatcgta acgcagcgtt aacaaaatac aggttgcgtt aacaaccaag ttgaaatgat    660
ttaatttctt aaatgtacga ccaggtccag ggtgacaatt aaagaggaga aaggtaccat   720 gaaacttta aaagtagcag caattgcagc aatcgtattc tccggtagcg ctctggcagg   780
tgttgttcct cagtacggcg gcggcggtaa ccacggtggt ggcggtaata atagcggccc   840
```

```
aaattctgag ctgaacattt accagtacgg tggcggtaac tctgcacttg ctctgcaaac      900
tgatgcccgt aactctgact tgactattac ccagcatggc ggcggtaatg gtgcagatgt      960
tggtcagggc tcagatgaca gctcaatcga tctgacccaa cgtggcttcg gtaacagcgc     1020
tactcttgat cagtggaacg gcaaaaattc tgaaatgacg gttaaacagt tcggtggtgg     1080
caacggtgct gcagttgacc agactgcatc taactcctcc gtcaacgtga ctcaggttgg     1140
ctttggtaac aacgcgaccg ctcatcagta ctaatacatc acgcgtggca tcaaataaaa     1200
cgaaaggctc agtcgaaaga ctgggccttt cgttttatct gttgtttgtc ggtgaacgct     1260
ctcctgagta ggacaaatcc gccgccctag acctagggta cgggttttgc tgcccgcaaa     1320
cgggctgttc tggtgttgct agtttgttat cagaatcgca gatccggctt caggtttgcc     1380
ggctgaaagc gctatttctt ccagaattgc catgattttt tccccacggg aggcgtcact     1440
ggctcccgtg ttgtcggcag ctttgattcg ataagcagca tcgcctgttt caggctgtct     1500
atgtgtgact gttgagctgt aacaagttgt ctcaggtgtt caatttcatg ttctagttgc     1560
tttgttttac tggtttcacc tgttctatta ggtgttacat gctgttcatc tgttacattg     1620
tcgatctgtt catggtgaac agctttaaat gcaccaaaaa ctcgtaaaag ctctgatgta     1680
tctatctttt ttacaccgtt ttcatctgtg catatggaca gttttcccct tgatatctaa     1740
cggtgaacag ttgttctact tttgtttgtt agtcttgatg cttcactgat agatacaaga     1800
gccataagaa cctcagatcc ttccgtattt agccagtatg ttctctagtg tggttcgttg     1860 ttttgcgtg agccatgaga acgaaccatt gagatcatgc ttactttgca tgtcactcaa      1920 aaatttgcc tcaaaactgg tgagctgaat ttttgcagtt aaagcatcgt gtagtgtttt      1980
tcttagtccg ttacgtaggt aggaatctga tgtaatggtt gttggtattt tgtcaccatt     2040 cattttatc tggttgttct caagttcggt tacgagatcc atttgtctat ctagttcaac      2100
ttggaaaatc aacgtatcag tcgggcggcc tcgcttatca accaccaatt tcatattgct     2160
gtaagtgttt aaatctttac ttattggttt caaaacccat tggttaagcc ttttaaactc     2220
atggtagtta ttttcaagca ttaacatgaa cttaaattca tcaaggctaa tctctatatt     2280
tgccttgtga gttttctttt gtgttagttc ttttaataac cactcataaa tcctcataga     2340
gtatttgttt tcaaaagact taacatgttc cagattatat tttatgaatt tttttaactg     2400 gaaagataa ggcaatatct cttcactaaa aactaattct aatttttcgc ttgagaactt      2460
ggcatagttt gtccactgga aaatctcaaa gcctttaacc aaaggattcc tgatttccac     2520
agttctcgtc atcagctctc tggttgcttt agctaataca ccataagcat tttccctact     2580
gatgttcatc atctgagcgt attggttata agtgaacgat accgtccgtt ctttccttgt     2640
agggttttca atcgtggggt tgagtagtgc cacacagcat aaaattagct tggtttcatg     2700
ctccgttaag tcatagcgac taatcgctag ttcatttgct ttgaaaacaa ctaattcaga     2760
catacatctc aattggtcta ggtgatttta atcactatac caattgagat gggctagtca     2820
atgataatta ctagtccttt tcctttgagt tgtgggtatc tgtaaattct gctagacctt     2880
tgctggaaaa cttgtaaatt ctgctagacc ctctgtaaat tccgctagac ctttgtgtgt     2940
tttttttgtt tatattcaag tggttataat ttatagaata agaaagaat aaaaaaagat      3000 aaaaagaata gatcccagcc ctgtgtataa ctcactactt tagtcagttc cgcagtatta     3060
caaaaggatg tcgcaaacgc tgtttgctcc tctacaaaac agaccttaaa acctaaagg      3120 cttaagtagc accctcgcaa gctcgggcaa atcgctgaat attccttttg tctccgacca     3180
```

```
tcaggcacct gagtcgctgt cttttttcgtg acattcagtt cgctgcgctc acggctctgg     3240
cagtgaatgg gggtaaatgg cactacaggc gcctttttatg gattcatgca aggaaactac     3300
ccataataca agaaaagccc gtcacgggct tctcagggcg ttttatggcg ggtctgctat     3360
gtggtgctat ctgactttt gctgttcagc agttcctgcc ctctgatttt ccagtctgac      3420
cacttcggat tatcccgtga caggtcattc agactggcta atgcacccag taaggcagcg     3480
gtatcatcaa caggcttacc cgtcttactg tccctagtgc ttggattctc accaataaaa     3540
aacgcccggc ggcaaccgag cgttctgaac aaatccagat ggagttctga ggtcattact     3600
ggatctatca acaggagtcc aagcgagctc gatatcaaat tacgcccgc cctgccactc      3660 atcgcagtac tgttgtaatt cattaagcat tctgccgaca tggaagccat cacagacggc     3720
atgatgaacc tgaatcgcca gcggcatcag caccttgtcg ccttgcgtat aatatttgcc     3780
catggtgaaa acggggggcga agaagttgtc catattggcc acgtttaaat caaaactggt    3840
gaaactcacc cagggattgg ctgagacgaa aaacatattc tcaataaacc ctttagggaa     3900
ataggccagg ttttcaccgt aacacgccac atcttgcgaa tatatgtgta gaaactgccg     3960
gaaatcgtcg tggtattcac tccagagcga tgaaaacgtt tcagtttgct catggaaaac     4020
ggtgtaacaa gggtgaacac tatcccatat caccagctca ccgtctttca ttgccatacg     4080
gaattccgga tgagcattca tcaggcgggc aagaatgtga ataaaggccg gataaaactt     4140
gtgcttattt ttctttacgg tcttttaaaaa ggccgtaata tccagctgaa cggtctggtt     4200
ataggtacat tgagcaactg actgaaatgc ctcaaaatgt tctttacgat gccattggga    4260
tatatcaacg gtggtatatc cagtgatttt tttctccatt ttagcttcct tagctcctga     4320
aaatctcgat aactcaaaaa atacgcccgg tagtgatctt atttcattat ggtgaaagtt     4380
ggaacctctt acgtgccgat caacgtctca ttttcgccag atatcgacgt ctaagaaacc    4440
attattatca tgacattaac ctataaaaat aggcgtatca cgaggccctt tcgtcttcac     4500
```

<210> SEQ ID NO 11
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 11

Gly Gly Gly Ser Cys Asn Asn Pro Met His Gln Asn Cys
1               5                   10

<210> SEQ ID NO 12
<211> LENGTH: 57
<212> TYPE: DNA
<213> ORGANISM: Artificial sequence
<220> FEATURE:
<223> OTHER INFORMATION: Synthetic polynucleotide

<400> SEQUENCE: 12
gcgaccgctc atcagtacgg tggtggttct tgcaacaacc cgatgcacca gaactgc          57

<210> SEQ ID NO 13
<211> LENGTH: 69
<212> TYPE: DNA
<213> ORGANISM: Artificial sequence
<220> FEATURE:
<223> OTHER INFORMATION: Synthetic polynucleotide

<400> SEQUENCE: 13

```
gatacgcgtt tagcagttct ggtgcatcgg gttgttgcaa gaaccaccac cgtactgatg    60
agcggtcgc                                                            69
```

<210> SEQ ID NO 14
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 14

```
gttctggtgc atcgggttgt tgcaagaacc accac                               35
```

<210> SEQ ID NO 15
<211> LENGTH: 36
<212> TYPE: DNA
<213> ORGANISM: Artificial sequence
<220> FEATURE:
<223> OTHER INFORMATION: Synthetic polynucleotide

<400> SEQUENCE: 15

```
gatacgcgtt tagcagttct ggtgcatcgg gttgtt                              36
```

<210> SEQ ID NO 16
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 16

```
Gly Gly Gly Ser Ser Leu Thr Pro Leu Thr Thr Ser His Leu Arg Ser
1               5                   10                  15
```

<210> SEQ ID NO 17
<211> LENGTH: 66
<212> TYPE: DNA
<213> ORGANISM: Artificial sequence
<220> FEATURE:
<223> OTHER INFORMATION: Synthetic polynucleotide

<400> SEQUENCE: 17

```
gcgaccgctc atcagtacgg tggtggttct tctctgaccc cgctgaccac ctctcacctg    60
cgttct                                                               66
```

<210> SEQ ID NO 18
<211> LENGTH: 78
<212> TYPE: DNA
<213> ORGANISM: Artificial sequence
<220> FEATURE:
<223> OTHER INFORMATION: Synthetic polynucleotide

<400> SEQUENCE: 18

```
gatacgcgtt taagaacgca ggtgagaggt ggtcagcggg gtcagagaag aaccaccacc    60
gtactgatga gcggtcgc                                                  78
```

<210> SEQ ID NO 19
<211> LENGTH: 69
<212> TYPE: DNA
<213> ORGANISM: Artificial sequence
<220> FEATURE:
<223> OTHER INFORMATION: Synthetic polynucleotide

<400> SEQUENCE: 19

-continued

```
ttaagaacgc aggtgagagg tggtcaacgg ggtcagagaa gaaccaccac cgtactgatg    60
agcggtcgc                                                             69

<210> SEQ ID NO 20
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 20
agaagaacca ccaccgtact gatgagcggt cgc                                  33

<210> SEQ ID NO 21
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 21
ggtcaacggg gtcagagaag aaccaccacc gtact                                35

<210> SEQ ID NO 22
<211> LENGTH: 36
<212> TYPE: DNA
<213> ORGANISM: Artificial sequence
<220> FEATURE:
<223> OTHER INFORMATION: Synthetic polynucleotide

<400> SEQUENCE: 22
acgcaggtga gaggtggtca acggggtcag agaaga                               36

<210> SEQ ID NO 23
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 23
gatacgcgtt taagaacgca ggtgagaggt ggt                                  33

<210> SEQ ID NO 24
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 24

Gly Gly Gly Ser Leu Lys Ala His Leu Pro Pro Ser Arg Leu Pro Ser
1               5                   10                  15

<210> SEQ ID NO 25
<211> LENGTH: 66
<212> TYPE: DNA
<213> ORGANISM: Artificial sequence
<220> FEATURE:
<223> OTHER INFORMATION: Synthetic polynucleotide

<400> SEQUENCE: 25
gcgaccgctc atcagtacgg tggtggttct ctgaaagctc acctgccgcc gtctcgtctg    60
ccgtct                                                                66
```

<210> SEQ ID NO 26
<211> LENGTH: 78
<212> TYPE: DNA
<213> ORGANISM: Artificial sequence
<220> FEATURE:
<223> OTHER INFORMATION: Synthetic polynucleotide

<400> SEQUENCE: 26
gatacgcgtt taagacggca gacgagacgg cggcaggtga gctttcagag aaccaccacc    60
gtactgatga gcggtcgc                                                 78

<210> SEQ ID NO 27
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 27
gagctttcag agaaccacca ccgtactgat gagcggtcgc                          40

<210> SEQ ID NO 28
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 28
cagacgagac ggcggcaggt gagctttcag agaaccacca                          40

<210> SEQ ID NO 29
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 29
gatacgcgtt taagacggca gacgagacgg cgg                                 33

<210> SEQ ID NO 30
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 30

Cys Asp Ser Pro His Arg His Ser Cys
1               5

<210> SEQ ID NO 31
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 31

Gly Gly Gly Ser Cys Asp Ser Pro His Arg His Ser Cys
1               5                   10

<210> SEQ ID NO 32
<211> LENGTH: 57

```
<212> TYPE: DNA
<213> ORGANISM: Artificial sequence
<220> FEATURE:
<223> OTHER INFORMATION: Synthetic polynucleotide

<400> SEQUENCE: 32
gcgaccgctc atcagtacgg tggtggatcc tgcgactctc cgcaccgtca ctcttgc     57

<210> SEQ ID NO 33
<211> LENGTH: 69
<212> TYPE: DNA
<213> ORGANISM: Artificial sequence
<220> FEATURE:
<223> OTHER INFORMATION: Synthetic polynucleotide

<400> SEQUENCE: 33
gatacgcgtt tagcaagagt gacggtgcgg agagtcgcag gatccaccac cgtactgatg    60
agcggtcgc                                                           69

<210> SEQ ID NO 34
<211> LENGTH: 42
<212> TYPE: DNA
<213> ORGANISM: Artificial sequence
<220> FEATURE:
<223> OTHER INFORMATION: Synthetic polynucleotide

<400> SEQUENCE: 34
aaagaggaga aaggtaccat gaaacttta aaagtagcag ca                       42

<210> SEQ ID NO 35
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 35
tcgcaggatc caccaccgta ctgatgagcg gtcgc                              35

<210> SEQ ID NO 36
<211> LENGTH: 32
<212> TYPE: DNA
<213> ORGANISM: Artificial sequence
<220> FEATURE:
<223> OTHER INFORMATION: Synthetic polynucleotide

<400> SEQUENCE: 36
tgacggtgcg gagagtcgca ggatccacca cc                                 32

<210> SEQ ID NO 37
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 37
gatacgcgtt tagcaagagt gacggtgcgg agagt                              35

<210> SEQ ID NO 38
<211> LENGTH: 12
<212> TYPE: PRT
<213> ORGANISM: Artificial sequence
<220> FEATURE:
<223> OTHER INFORMATION: Synthetic polypeptide
```

```
<400> SEQUENCE: 38

His Asn Lys His Leu Pro Ser Thr Gln Pro Leu Ala
1               5                   10

<210> SEQ ID NO 39
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 39

Gly Gly Gly Ser His Asn Lys His Leu Pro Ser Thr Gln Pro Leu Ala
1               5                   10                  15

<210> SEQ ID NO 40
<211> LENGTH: 66
<212> TYPE: DNA
<213> ORGANISM: Artificial sequence
<220> FEATURE:
<223> OTHER INFORMATION: Synthetic polynucleotide

<400> SEQUENCE: 40
gcgaccgctc atcagtacgg tggtggatcc cacaacaaac acctgccgtc tacccagccg      60
ctggct                                                                 66

<210> SEQ ID NO 41
<211> LENGTH: 78
<212> TYPE: DNA
<213> ORGANISM: Artificial sequence
<220> FEATURE:
<223> OTHER INFORMATION: Synthetic polynucleotide

<400> SEQUENCE: 41
gatacgcgtt taagccagcg gctgggtaga cggcaggtgt ttgttgtggg atccaccacc      60
gtactgatga gcggtcgc                                                    78

<210> SEQ ID NO 42
<211> LENGTH: 38
<212> TYPE: DNA
<213> ORGANISM: Artificial sequence
<220> FEATURE:
<223> OTHER INFORMATION: Synthetic polynucleotide

<400> SEQUENCE: 42
ttgttgtggg atccaccacc gtactgatga gcggtcgc                              38

<210> SEQ ID NO 43
<211> LENGTH: 38
<212> TYPE: DNA
<213> ORGANISM: Artificial sequence
<220> FEATURE:
<223> OTHER INFORMATION: Synthetic polynucleotide

<400> SEQUENCE: 43
tgggtagacg gcaggtgttt gttgtgggat ccaccacc                              38

<210> SEQ ID NO 44
<211> LENGTH: 38
<212> TYPE: DNA
<213> ORGANISM: Artificial sequence
<220> FEATURE:
<223> OTHER INFORMATION: Synthetic polynucleotide

<400> SEQUENCE: 44
```
gatacgcgtt taagccagcg gctgggtaga cggcaggt                                    38

<210> SEQ ID NO 45
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 45

Cys Asn Ala Gly Asp His Ala Asn Cys
1               5

<210> SEQ ID NO 46
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 46

Gly Gly Gly Ser Cys Asn Ala Gly Asp His Ala Asn Cys
1               5                   10

<210> SEQ ID NO 47
<211> LENGTH: 57
<212> TYPE: DNA
<213> ORGANISM: Artificial sequence
<220> FEATURE:
<223> OTHER INFORMATION: Synthetic polynucleotide

<400> SEQUENCE: 47
gcgaccgctc atcagtacgg tggtggatcc tgcaacgctg gtgaccacgc taactgc      57

<210> SEQ ID NO 48
<211> LENGTH: 69
<212> TYPE: DNA
<213> ORGANISM: Artificial sequence
<220> FEATURE:
<223> OTHER INFORMATION: Synthetic polynucleotide

<400> SEQUENCE: 48
gatacgcgtt tagcagttag cgtggtcacc agcgttgcag gatccaccac cgtactgatg   60
agcggtcgc                                                            69

<210> SEQ ID NO 49
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 49
ttgcaggatc caccaccgta ctgatgagcg gtcgc                               35

<210> SEQ ID NO 50
<211> LENGTH: 34
<212> TYPE: DNA
<213> ORGANISM: Artificial sequence
<220> FEATURE:
<223> OTHER INFORMATION: Synthetic polynucleotide

<400> SEQUENCE: 50
gcgtggtcac cagcgttgca ggatccacca ccgt                                34

```
<210> SEQ ID NO 51
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 51
gatacgcgtt tagcagttag cgtggtcacc agcgt                              35

<210> SEQ ID NO 52
<211> LENGTH: 38
<212> TYPE: DNA
<213> ORGANISM: Artificial sequence
<220> FEATURE:
<223> OTHER INFORMATION: Synthetic polynucleotide

<400> SEQUENCE: 52
tcgtcgtcat ccttgtagtc gtactgatga gcggtcgc                           38

<210> SEQ ID NO 53
<211> LENGTH: 36
<212> TYPE: DNA
<213> ORGANISM: Artificial sequence
<220> FEATURE:
<223> OTHER INFORMATION: Synthetic polynucleotide

<400> SEQUENCE: 53
gatacgcgtt tacttgtcgt cgtcatcctt gtagtc                             36

<210> SEQ ID NO 54
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 54

His His His His His His
1               5

<210> SEQ ID NO 55
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 55

Gly Gly Gly Ser His His His His His His
1               5                   10

<210> SEQ ID NO 56
<211> LENGTH: 48
<212> TYPE: DNA
<213> ORGANISM: Artificial sequence
<220> FEATURE:
<223> OTHER INFORMATION: Synthetic polynucleotide

<400> SEQUENCE: 56
gcgaccgctc atcagtacgg tggtggatcc catcatcacc atcaccac                48

<210> SEQ ID NO 57
<211> LENGTH: 60
<212> TYPE: DNA
<213> ORGANISM: Artificial sequence
```

```
<220> FEATURE:
<223> OTHER INFORMATION: Synthetic polynucleotide

<400> SEQUENCE: 57
gatacgcgtt tagtggtgat ggtgatgatg ggatccacca ccgtactgat gagcggtcgc    60

<210> SEQ ID NO 58
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 58
ggtgatgatg ggatccacca ccgtactgat gagcggtcgc                          40

<210> SEQ ID NO 59
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 59
gatacgcgtt tagtggtgat ggtgatgatg ggatccacc                           39

<210> SEQ ID NO 60
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 60
caccatcacc atcaccacca t                                              21

<210> SEQ ID NO 61
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 61

His His His His His His His
1               5

<210> SEQ ID NO 62
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 62
atggtggtga tggtgatggt g                                              21

<210> SEQ ID NO 63
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 63
atgaaacttt taaaagtagc agcaattgca gcaatcgtat tctccggtag cgctctggca    60
```

<210> SEQ ID NO 64
<211> LENGTH: 66
<212> TYPE: DNA
<213> ORGANISM: Artificial sequence
<220> FEATURE:
<223> OTHER INFORMATION: Synthetic polynucleotide

<400> SEQUENCE: 64
ggtgttgttc ctcagtacgg cggcggcggt aaccacggtg gtggcggtaa taatagcggc    60
ccaaat    66

<210> SEQ ID NO 65
<211> LENGTH: 69
<212> TYPE: DNA
<213> ORGANISM: Artificial sequence
<220> FEATURE:
<223> OTHER INFORMATION: Synthetic polynucleotide

<400> SEQUENCE: 65
tctgagctga acatttacca gtacggtggc ggtaactctg cacttgctct gcaaactgat    60
gcccgtaac    69

<210> SEQ ID NO 66
<211> LENGTH: 66
<212> TYPE: DNA
<213> ORGANISM: Artificial sequence
<220> FEATURE:
<223> OTHER INFORMATION: Synthetic polynucleotide

<400> SEQUENCE: 66
tctgacttga ctattaccca gcatggcggc ggtaatggtg cagatgttgg tcagggctca    60
gatgac    66

<210> SEQ ID NO 67
<211> LENGTH: 69
<212> TYPE: DNA
<213> ORGANISM: Artificial sequence
<220> FEATURE:
<223> OTHER INFORMATION: Synthetic polynucleotide

<400> SEQUENCE: 67
agctcaatcg atctgaccca acgtggcttc ggtaacagcg ctactcttga tcagtggaac    60
ggcaaaaat    69

<210> SEQ ID NO 68
<211> LENGTH: 66
<212> TYPE: DNA
<213> ORGANISM: Artificial sequence
<220> FEATURE:
<223> OTHER INFORMATION: Synthetic polynucleotide

<400> SEQUENCE: 68
tctgaaatga cggttaaaca gttcggtggt ggcaacggtg ctgcagttga ccagactgca    60
tctaac    66

<210> SEQ ID NO 69
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 69
tcctccgtca acgtgactca ggttggcttt ggtaacaacg cgaccgctca tcagtactaa    60

<210> SEQ ID NO 70
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 70

Met Lys Leu Leu Lys Val Ala Ala Ile Ala Ala Ile Val Phe Ser Gly
1               5                   10                  15

Ser Ala Leu Ala
            20

<210> SEQ ID NO 71
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 71

Gly Val Val Pro Gln Tyr Gly Gly Gly Gly Asn His Gly Gly Gly Gly
1               5                   10                  15

Asn Asn Ser Gly Pro Asn
            20

<210> SEQ ID NO 72
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 72

Ser Glu Leu Asn Ile Tyr Gln Tyr Gly Gly Gly Asn Ser Ala Leu Ala
1               5                   10                  15

Leu Gln Thr Asp Ala Arg Asn
            20

<210> SEQ ID NO 73
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 73

Ser Asp Leu Thr Ile Thr Gln His Gly Gly Gly Asn Gly Ala Asp Val
1               5                   10                  15

Gly Gln Gly Ser Asp Asp
            20

<210> SEQ ID NO 74
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 74

Ser Ser Ile Asp Leu Thr Gln Arg Gly Phe Gly Asn Ser Ala Thr Leu

-continued

```
                 1               5                  10                 15
Asp Gln Trp Asn Gly Lys Asn
                20

<210> SEQ ID NO 75
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 75

Ser Glu Met Thr Val Lys Gln Phe Gly Gly Gly Asn Gly Ala Ala Val
1               5                  10                 15

Asp Gln Thr Ala Ser Asn
                20

<210> SEQ ID NO 76
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 76

Ser Ser Val Asn Val Thr Gln Val Gly Phe Gly Asn Asn Ala Thr Ala
1               5                  10                 15

His Gln Tyr

<210> SEQ ID NO 77
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 77
accatcacca tcaccaccat gcccgtaact ctgacttga                              39

<210> SEQ ID NO 78
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 78
tggtggtgat ggtgatggtg atcagtttgc agagcaagt                              39

<210> SEQ ID NO 79
<211> LENGTH: 158
<212> TYPE: PRT
<213> ORGANISM: Artificial sequence
<220> FEATURE:
<223> OTHER INFORMATION: Synthetic polypeptide

<400> SEQUENCE: 79

Met Lys Leu Leu Lys Val Ala Ala Ile Ala Ala Ile Val Phe Ser Gly
1               5                  10                 15

Ser Ala Leu Ala Gly Val Val Pro Gln Tyr Gly Gly Gly Gly Asn His
                20                  25                 30

Gly Gly Gly Gly Asn Asn Ser Gly Pro Asn Ser Glu Leu Asn Ile Tyr
        35                  40                  45
```

```
Gln Tyr Gly Gly Gly Asn Ser Ala Leu Ala Leu Gln Thr Asp His His
    50                  55                  60

His His His His His Ala Arg Asn Ser Asp Leu Thr Ile Thr Gln His
65                  70                  75                  80

Gly Gly Gly Asn Gly Ala Asp Val Gly Gln Gly Ser Asp Asp Ser Ser
                85                  90                  95

Ile Asp Leu Thr Gln Arg Gly Phe Gly Asn Ser Ala Thr Leu Asp Gln
                100                 105                 110

Trp Asn Gly Lys Asn Ser Glu Met Thr Val Lys Gln Phe Gly Gly Gly
                115                 120                 125

Asn Gly Ala Ala Val Asp Gln Thr Ala Ser Asn Ser Ser Val Asn Val
                130                 135                 140

Thr Gln Val Gly Phe Gly Asn Asn Ala Thr Ala His Gln Tyr
145                 150                 155
```

<210> SEQ ID NO 80
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 80
accatcacca tcaccaccat gatgacagct caatcgatct     40

<210> SEQ ID NO 81
<211> LENGTH: 38
<212> TYPE: DNA
<213> ORGANISM: Artificial sequence
<220> FEATURE:
<223> OTHER INFORMATION: Synthetic polynucleotide

<400> SEQUENCE: 81
tggtggtgat ggtgatggtg tgagccctga ccaacatc     38

<210> SEQ ID NO 82
<211> LENGTH: 165
<212> TYPE: PRT
<213> ORGANISM: Artificial sequence
<220> FEATURE:
<223> OTHER INFORMATION: Synthetic polypeptide

<400> SEQUENCE: 82

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
                20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser His His His His His His Asp Asp Ser Ser
                85                  90                  95

Ile Asp Leu Thr Gln Arg Gly Phe Gly Asn Ser Ala Thr Leu Asp Gln
                100                 105                 110

Trp Asn Gly Lys Asn Ser Glu Met Thr Val Lys Gln Phe Gly Gly Gly
                115                 120                 125
```

```
Asn Gly Ala Ala Val Asp Gln Thr Ala Ser Asn Ser Ser Val Asn Val
    130                 135                 140

Thr Gln Val Gly Phe Gly Asn Asn Ala Thr Ala His Gln Tyr Thr Arg
145                 150                 155                 160

Ala Arg Gly Ile Lys
            165
```

<210> SEQ ID NO 83
<211> LENGTH: 41
<212> TYPE: DNA
<213> ORGANISM: Artificial sequence
<220> FEATURE:
<223> OTHER INFORMATION: Synthetic polynucleotide

<400> SEQUENCE: 83
accatcacca tcaccaccat ggcaaaaatt ctgaaatgac g                41

<210> SEQ ID NO 84
<211> LENGTH: 41
<212> TYPE: DNA
<213> ORGANISM: Artificial sequence
<220> FEATURE:
<223> OTHER INFORMATION: Synthetic polynucleotide

<400> SEQUENCE: 84
tggtggtgat ggtgatggtg gttccactga tcaagagtag c                41

<210> SEQ ID NO 85
<211> LENGTH: 158
<212> TYPE: PRT
<213> ORGANISM: Artificial sequence
<220> FEATURE:
<223> OTHER INFORMATION: Synthetic polypeptide

<400> SEQUENCE: 85

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Ser Ser Ile Asp Leu Thr Gln Arg Gly
                85                  90                  95

Phe Gly Asn Ser Ala Thr Leu Asp Gln Trp Asn His His His His
            100                 105                 110

His His Gly Lys Asn Ser Glu Met Thr Val Lys Gln Phe Gly Gly Gly
        115                 120                 125

Asn Gly Ala Ala Val Asp Gln Thr Ala Ser Asn Ser Ser Val Asn Val
    130                 135                 140

Thr Gln Val Gly Phe Gly Asn Asn Ala Thr Ala His Gln Tyr
145                 150                 155
```

<210> SEQ ID NO 86
<211> LENGTH: 39
<212> TYPE: DNA
<213> ORGANISM: Artificial sequence
<220> FEATURE:

<223> OTHER INFORMATION: Synthetic polynucleotide

<400> SEQUENCE: 86
accatcacca tcaccaccat tctaactcct ccgtcaacg                                    39

<210> SEQ ID NO 87
<211> LENGTH: 38
<212> TYPE: DNA
<213> ORGANISM: Artificial sequence
<220> FEATURE:
<223> OTHER INFORMATION: Synthetic polynucleotide

<400> SEQUENCE: 87
tggtggtgat ggtgatggtg tgcagtctgg tcaactgc                                    38

<210> SEQ ID NO 88
<211> LENGTH: 158
<212> TYPE: PRT
<213> ORGANISM: Artificial sequence
<220> FEATURE:
<223> OTHER INFORMATION: Synthetic polypeptide

<400> SEQUENCE: 88

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala His His His His His His Ser Asn Ser Ser Val Asn Val
    130                 135                 140

Thr Gln Val Gly Phe Gly Asn Asn Ala Thr Ala His Gln Tyr
145                 150                 155

<210> SEQ ID NO 89
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 89
accatcacca tcaccaccat ggtaactctg cacttgctc                                    39

<210> SEQ ID NO 90
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 90
tggtggtgat ggtgatggtg gccaccgtac tggtaaatgt                                40

<210> SEQ ID NO 91
<211> LENGTH: 158
<212> TYPE: PRT
<213> ORGANISM: Artificial sequence
<220> FEATURE:
<223> OTHER INFORMATION: Synthetic polypeptide

<400> SEQUENCE: 91

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly His His His His His His Gly Asn Ser Ala Leu
    50                  55                  60

Ala Leu Gln Thr Asp Ala Arg Asn Ser Asp Leu Thr Ile Thr Gln His
65                  70                  75                  80

Gly Gly Gly Asn Gly Ala Asp Val Gly Gln Gly Ser Asp Asp Ser Ser
                85                  90                  95

Ile Asp Leu Thr Gln Arg Gly Phe Gly Asn Ser Ala Thr Leu Asp Gln
            100                 105                 110

Trp Asn Gly Lys Asn Ser Glu Met Thr Val Lys Gln Phe Gly Gly Gly
        115                 120                 125

Asn Gly Ala Ala Val Asp Gln Thr Ala Ser Asn Ser Ser Val Asn Val
    130                 135                 140

Thr Gln Val Gly Phe Gly Asn Asn Ala Thr Ala His Gln Tyr
145                 150                 155

<210> SEQ ID NO 92
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 92
accatcacca tcaccaccat ggtaatggtg cagatgttgg                                40

<210> SEQ ID NO 93
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 93
tggtggtgat ggtgatggtg gccgccatgc tgggt                                     35

<210> SEQ ID NO 94
<211> LENGTH: 158
<212> TYPE: PRT
<213> ORGANISM: Artificial sequence
<220> FEATURE:
<223> OTHER INFORMATION: Synthetic polypeptide

<400> SEQUENCE: 94

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
 50                  55                  60

Asn Ser Asp Leu Thr Ile Thr Gln His Gly Gly His His His His
 65                  70                  75                  80

His His Gly Asn Gly Ala Asp Val Gly Gln Gly Ser Asp Asp Ser Ser
                85                  90                  95

Ile Asp Leu Thr Gln Arg Gly Phe Gly Asn Ser Ala Thr Leu Asp Gln
            100                 105                 110

Trp Asn Gly Lys Asn Ser Glu Met Thr Val Lys Gln Phe Gly Gly Gly
            115                 120                 125

Asn Gly Ala Ala Val Asp Gln Thr Ala Ser Asn Ser Ser Val Asn Val
        130                 135                 140

Thr Gln Val Gly Phe Gly Asn Asn Ala Thr Ala His Gln Tyr
145                 150                 155

<210> SEQ ID NO 95
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 95
accatcacca tcaccaccat ggtaacagcg ctactcttg                              39

<210> SEQ ID NO 96
<211> LENGTH: 38
<212> TYPE: DNA
<213> ORGANISM: Artificial sequence
<220> FEATURE:
<223> OTHER INFORMATION: Synthetic polynucleotide

<400> SEQUENCE: 96
tggtggtgat ggtgatggtg aagccacgt tgggtcag                               38

<210> SEQ ID NO 97
<211> LENGTH: 165
<212> TYPE: PRT
<213> ORGANISM: Artificial sequence
<220> FEATURE:
<223> OTHER INFORMATION: Synthetic polypeptide

<400> SEQUENCE: 97

Met Lys Leu Leu Lys Val Ala Ala Ile Ala Ala Ile Val Phe Ser Gly
 1               5                  10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
 50                  55                  60

Asn Ser Asp Leu Thr Ile Thr Gln His Gly Gly Gly Asn Gly Ala Asp
 65                  70                  75                  80

Val Gly Gln Gly Ser Asp Asp Ser Ser Ile Asp Leu Thr Gln Arg Gly
                85                  90                  95

Phe His His His His His His Gly Asn Ser Ala Thr Leu Asp Gln
            100                 105                 110

Trp Asn Gly Lys Asn Ser Glu Met Thr Val Lys Gln Phe Gly Gly Gly
            115                 120                 125

Asn Gly Ala Ala Val Asp Gln Thr Ala Ser Asn Ser Ser Val Asn Val
130                 135                 140

Thr Gln Val Gly Phe Gly Asn Asn Ala Thr Ala His Gln Tyr Thr Arg
145                 150                 155                 160

Ala Arg Gly Ile Lys
                165

<210> SEQ ID NO 98
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 98
accatcacca tcaccaccat ggcaacggtg ctgca          35

<210> SEQ ID NO 99
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 99
tggtggtgat ggtgatggtg accaccgaac tgtttaaccg          40

<210> SEQ ID NO 100
<211> LENGTH: 158
<212> TYPE: PRT
<213> ORGANISM: Artificial sequence
<220> FEATURE:
<223> OTHER INFORMATION: Synthetic polypeptide

<400> SEQUENCE: 100

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Cys Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly His His His His His His Gly
            115                 120                 125

Asn Gly Ala Ala Val Asp Gln Thr Ala Ser Asn Ser Ser Val Asn Val
        130                 135                 140

Thr Gln Val Gly Phe Gly Asn Asn Ala Thr Ala His Gln Tyr
145                 150                 155

<210> SEQ ID NO 101
<211> LENGTH: 37
<212> TYPE: DNA
<213> ORGANISM: Artificial sequence
<220> FEATURE:
<223> OTHER INFORMATION: Synthetic polynucleotide

<400> SEQUENCE: 101
accatcacca tcaccaccat ggtaacaacg cgaccgc    37

<210> SEQ ID NO 102
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 102
tggtggtgat ggtgatggtg aaagccaacc tgagtcacg    39

<210> SEQ ID NO 103
<211> LENGTH: 158
<212> TYPE: PRT
<213> ORGANISM: Artificial sequence
<220> FEATURE:
<223> OTHER INFORMATION: Synthetic polypeptide

<400> SEQUENCE: 103

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Asn Gly Ala Ala Val Asp Gln
        115                 120                 125

Thr Ala Ser Asn Ser Ser Val Asn Val Thr Gln Val Gly Phe His His
    130                 135                 140

His His His His Gly Asn Asn Ala Thr Ala His Gln Tyr
145                 150                 155

<210> SEQ ID NO 104
<211> LENGTH: 32
<212> TYPE: DNA
<213> ORGANISM: Artificial sequence
<220> FEATURE:
<223> OTHER INFORMATION: Synthetic polynucleotide

<400> SEQUENCE: 104
gacaatacgc gtttagtact gatgagcggt cg    32

<210> SEQ ID NO 105

<211> LENGTH: 22
<212> TYPE: PRT
<213> ORGANISM: Artificial sequence
<220> FEATURE:
<223> OTHER INFORMATION: Synthetic polypeptide

<400> SEQUENCE: 105

Gly Val Val Pro Gln Tyr Gly Gly Gly Asn Ala Gly Gly Gly
1               5                   10                  15

Asn Asn Ser Gly Pro Asn
            20

<210> SEQ ID NO 106
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 106

Ser Glu Leu Asn Ile Tyr Gln Tyr Gly Gly Asn Ser Ala Leu Ala
1               5                   10                  15

Leu Gln Thr Asp Ala Arg Asn
            20

<210> SEQ ID NO 107
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 107

Ser Asp Leu Thr Ile Thr Gln Ala Gly Gly Asn Gly Ala Asp Val
1               5                   10                  15

Gly Gln Gly Ser Asp Asp
            20

<210> SEQ ID NO 108
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 108

Ser Ser Ile Asp Leu Thr Gln Arg Gly Phe Gly Asn Ser Ala Thr Leu
1               5                   10                  15

Asp Gln Ala Asn Gly Lys Asn
            20

<210> SEQ ID NO 109
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 109

Ser Glu Ala Thr Val Lys Gln Phe Gly Gly Asn Gly Ala Ala Val
1               5                   10                  15

Asp Gln Thr Ala Ser Asn
            20

```
<210> SEQ ID NO 110
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 110

Ser Ser Val Asn Val Thr Gln Val Gly Phe Gly Asn Asn Ala Thr Ala
1               5                   10                  15

Ala Gln Tyr

<210> SEQ ID NO 111
<211> LENGTH: 456
<212> TYPE: DNA
<213> ORGANISM: Artificial sequence
<220> FEATURE:
<223> OTHER INFORMATION: Synthetic polynucleotide

<400> SEQUENCE: 111
atgaaacttt taaaagtagc agcaattgca gcaatcgtat tctccggtag cgctctggca      60
ggtgttgttc ctcagtacgg cggcggcggt aaccacggtg gtggcggtaa taatagcggc     120
ccaaattctg agctgaacat ttaccagtac ggtggcggta actctgcact tgctctgcaa     180
actgatgccc gtaactctga cttgactatt acccagcatg gcggcggtaa tggtgcagat     240
gttggtcagg gctcagatga cagctcaatc gatctgaccc aacgtggctt cggtaacagc     300
gctactcttg atcagtggaa cggcaaaaat tctgaaatga cggttaaaca gttcggtggt     360
ggcaacggtg ctgcagttga ccagactgca tctaactcct ccgtcaacgt gactcaggtt     420
ggctttggta caacgcgac cgctcatcag tactaa                                456

<210> SEQ ID NO 112
<211> LENGTH: 26
<212> TYPE: DNA
<213> ORGANISM: Artificial sequence
<220> FEATURE:
<223> OTHER INFORMATION: Synthetic polynucleotide

<400> SEQUENCE: 112
ggcggcggta acgccggtgg tggcgg                                            26

<210> SEQ ID NO 113
<211> LENGTH: 26
<212> TYPE: DNA
<213> ORGANISM: Artificial sequence
<220> FEATURE:
<223> OTHER INFORMATION: Synthetic polynucleotide

<400> SEQUENCE: 113
ccgccaccac cggcgttacc gccgcc                                            26

<210> SEQ ID NO 114
<211> LENGTH: 36
<212> TYPE: DNA
<213> ORGANISM: Artificial sequence
<220> FEATURE:
<223> OTHER INFORMATION: Synthetic polynucleotide

<400> SEQUENCE: 114
gacttgacta ttacccaggc tggcggcggt aatggt                                 36

<210> SEQ ID NO 115
<211> LENGTH: 36
```

```
<212> TYPE: DNA
<213> ORGANISM: Artificial sequence
<220> FEATURE:
<223> OTHER INFORMATION: Synthetic polynucleotide

<400> SEQUENCE: 115
accattaccg ccgccagcct gggtaatagt caagtc                           36

<210> SEQ ID NO 116
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 116
cagcgctact cttgatcagg cgaacggcaa aaattctgaa                       40

<210> SEQ ID NO 117
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 117
ttcagaattt ttgccgttcg cctgatcaag agtagcgctg                       40

<210> SEQ ID NO 118
<211> LENGTH: 47
<212> TYPE: DNA
<213> ORGANISM: Artificial sequence
<220> FEATURE:
<223> OTHER INFORMATION: Synthetic polynucleotide

<400> SEQUENCE: 118
ttgatcagtg gaacggcaaa aattctgaag cgacggttaa acagttc               47

<210> SEQ ID NO 119
<211> LENGTH: 47
<212> TYPE: DNA
<213> ORGANISM: Artificial sequence
<220> FEATURE:
<223> OTHER INFORMATION: Synthetic polynucleotide

<400> SEQUENCE: 119
gaactgttta accgtcgctt cagaattttt gccgttccac tgatcaa               47

<210> SEQ ID NO 120
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 120
gacaatacgc gtttagtact gagcagcggt cgcgttgtta                       40

<210> SEQ ID NO 121
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 121
```

-continued

```
attttcacat gttctagggc ggcggatttg                                        30
```

<210> SEQ ID NO 122
<211> LENGTH: 456
<212> TYPE: DNA
<213> ORGANISM: E. coli

<400> SEQUENCE: 122

```
atgaaacttt aaaagtagc agcaattgca gcaatcgtat tctccggtag cgctctggca        60
ggtgttgttc ctcagtacgg cggcggcggt aaccacggtg gtggcggtaa taatagcggc      120
ccaaattctg agctgaacat ttaccagtac ggtggcggta actctgcact tgctctgcaa      180
actgatgccc gtaactctga cttgactatt acccagcatg gcggcggtaa tggtgcagat      240
gttggtcagg gctcagatga cagctcaatc gatctgaccc aacgtggctt cggtaacagc      300
gctactcttg atcagtggaa cggcaaaaat tctgaaatga cggttaaaca gttcggtggt      360
ggcaacggtg ctgcagttga ccagactgca tctaactcct ccgtcaacgt gactcaggtt      420
ggctttggta caacgcgac cgctcatcag tactaa                                 456
```

<210> SEQ ID NO 123
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 123

```
gttgttgcaa gaaccaccac cgtactgatg agcggtcgc                              39
```

<210> SEQ ID NO 124
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 124

```
Met Lys Asn Lys Leu Leu Phe Met Met Leu Thr Ile Leu Gly Ala Pro
1               5                   10                  15

Gly Ile Ala Ala Ala
            20
```

<210> SEQ ID NO 125
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 125

```
Ala Gly Tyr Asp Leu Ala Asn Ser Glu Tyr Asn Phe Ala Val Asn Glu
1               5                   10                  15

Leu Ser Lys Ser Ser Phe Asn
            20
```

<210> SEQ ID NO 126
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 126

```
Gln Ala Ala Ile Ile Gly Gln Ala Gly Thr Asn Asn Ser Ala Gln Leu
1               5                   10                  15

Arg Gln Gly Gly Ser Lys
            20

<210> SEQ ID NO 127
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 127

Leu Leu Ala Val Val Ala Gln Glu Gly Ser Ser Asn Arg Ala Lys Ile
1               5                   10                  15

Asp Gln Thr Gly Asp Tyr
            20

<210> SEQ ID NO 128
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 128

Asn Leu Ala Tyr Ile Asp Gln Ala Gly Ser Ala Asn Asp Ala Ser Ile
1               5                   10                  15

Ser Gln Gly Ala Tyr Gly
            20

<210> SEQ ID NO 129
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 129

Asn Thr Ala Met Ile Ile Gln Lys Gly Ser Gly Asn Lys Ala Asn Ile
1               5                   10                  15

Thr Gln Tyr Gly Thr Gln
            20

<210> SEQ ID NO 130
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 130

Lys Thr Ala Ile Val Val Gln Arg Gln Ser Gln Met Ala Ile Arg Val
1               5                   10                  15

Thr Gln Arg

<210> SEQ ID NO 131
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 131
```

```
Leu Arg Gln Gly Gly Ser Lys Leu Leu Ala Val Val Ala Gln Glu Gly
1               5                   10                  15

Ser Ser Asn Arg
            20

<210> SEQ ID NO 132
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 132

Gln Gly Gly Ser Lys Leu Leu Ala Val Val Ala Gln Glu Gly Ser Ser
1               5                   10                  15

Asn Arg Ala Lys
            20

<210> SEQ ID NO 133
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 133

Gly Thr Gln Lys Thr Ala Ile Val Val Gln Arg Gln Ser Gln Met Ala
1               5                   10                  15

Ile Arg Val Thr
            20
```